US011124839B2

(12) United States Patent
Gualberto et al.

(10) Patent No.: US 11,124,839 B2
(45) Date of Patent: Sep. 21, 2021

(54) METHODS OF TREATING CANCER PATIENTS WITH FARNESYLTRANSFERASE INHIBITORS

(71) Applicant: Kura Oncology, Inc., San Diego, CA (US)

(72) Inventors: Antonio Gualberto, Acton, MA (US); Catherine Rose Scholz, Woburn, MA (US)

(73) Assignee: KURA ONCOLOGY, INC., San Diego, CA (US)

( * ) Notice: Subject to any disclaimer, the term of this patent is extended or adjusted under 35 U.S.C. 154(b) by 0 days.

(21) Appl. No.: 15/802,233

(22) Filed: Nov. 2, 2017

(65) Prior Publication Data

US 2018/0187266 A1    Jul. 5, 2018

Related U.S. Application Data

(60) Provisional application No. 62/417,044, filed on Nov. 3, 2016.

(51) Int. Cl.
| | | |
|---|---|---|
| *A61K 31/4709* | (2006.01) | |
| *A61P 35/00* | (2006.01) | |
| *C12Q 1/6886* | (2018.01) | |
| *A61K 31/00* | (2006.01) | |
| *C12Q 1/68* | (2018.01) | |
| *A61P 35/04* | (2006.01) | |

(52) U.S. Cl.
CPC ............ *C12Q 1/6886* (2013.01); *A61K 31/00* (2013.01); *A61K 31/4709* (2013.01); *A61P 35/00* (2018.01); *A61P 35/04* (2018.01); *C12Q 1/68* (2013.01); *C12Q 2600/106* (2013.01); *C12Q 2600/156* (2013.01)

(58) Field of Classification Search
CPC ............................. A61K 31/4709; A61P 35/00
See application file for complete search history.

(56) References Cited

U.S. PATENT DOCUMENTS

| | | |
|---|---|---|
| 5,238,922 A | 8/1993 | Graham et al. |
| 5,420,245 A | 5/1995 | Brown et al. |
| 5,491,164 A | 2/1996 | De Solms et al. |
| 5,504,212 A | 4/1996 | De Solms et al. |
| 5,523,430 A | 6/1996 | Patel et al. |
| 5,532,359 A | 7/1996 | Marsters et al. |
| 5,534,537 A | 7/1996 | Ciccarone et al. |
| 5,578,629 A | 11/1996 | Ciccarone et al. |
| 5,585,359 A | 12/1996 | Breslin et al. |
| 5,602,098 A | 2/1997 | Sebti et al. |
| 5,661,161 A | 8/1997 | Anthony et al. |
| 5,700,806 A | 12/1997 | Doll et al. |
| 5,721,236 A | 2/1998 | Bishop et al. |
| 5,750,567 A | 5/1998 | Baudoin et al. |
| 5,756,528 A | 5/1998 | Anthony et al. |
| 5,767,274 A | 6/1998 | Kim |
| 5,773,455 A | 6/1998 | Dong et al. |
| 5,780,492 A | 7/1998 | Dinsmore et al. |
| 5,807,852 A | 9/1998 | Doll et al. |
| 5,843,941 A | 12/1998 | Marsters et al. |
| 5,852,010 A | 12/1998 | Graham et al. |
| 5,856,326 A | 1/1999 | Anthony et al. |
| 5,856,439 A | 1/1999 | Clerc |
| 5,859,015 A | 1/1999 | Graham et al. |
| 5,861,529 A | 1/1999 | Baudoin et al. |
| 5,869,682 A | 2/1999 | Desolms |
| 5,872,135 A | 2/1999 | Desolms |
| 5,874,442 A | 2/1999 | Doll et al. |
| 5,880,140 A | 3/1999 | Anthony |
| 5,889,053 A | 3/1999 | Baudoin et al. |
| 5,891,889 A | 4/1999 | Anthony et al. |
| 5,936,097 A | 8/1999 | Commercon et al. |
| 5,939,557 A | 8/1999 | Anthony et al. |
| 5,958,939 A | 9/1999 | Afonso et al. |
| 5,965,539 A | 10/1999 | Sebti et al. |
| 5,965,578 A | 10/1999 | Graham et al. |
| 5,968,952 A | 10/1999 | Venet et al. |
| 5,972,966 A | 10/1999 | Desolms et al. |
| 5,972,984 A | 10/1999 | Anthony et al. |
| 5,976,851 A | 11/1999 | Brown et al. |
| 5,986,965 A | 11/1999 | Lee et al. |
| 6,037,350 A | 3/2000 | Venet et al. |
| 6,169,096 B1 | 1/2001 | Venet et al. |
| 6,177,432 B1 | 1/2001 | Angibaud et al. |
| 6,187,786 B1 | 2/2001 | Venet et al. |
| 6,365,600 B1 | 4/2002 | End et al. |
| 6,420,387 B1 | 7/2002 | Venet et al. |
| 6,451,812 B1 | 9/2002 | End et al. |
| 6,458,800 B1 | 10/2002 | Angibaud et al. |
| 6,545,020 B1 | 4/2003 | Van Ginckel et al. |
| 6,734,194 B2 | 5/2004 | End et al. |
| 6,743,805 B2 | 6/2004 | End et al. |
| 6,838,467 B2 | 1/2005 | End |
| 6,844,439 B2 | 1/2005 | Fillers et al. |
| 6,914,066 B2 | 7/2005 | Angibaud et al. |
| 7,241,777 B2 | 7/2007 | Angibaud et al. |
| 7,253,183 B2 | 8/2007 | End et al. |
| 7,456,287 B2 | 11/2008 | Filliers et al. |
| 7,468,363 B2 | 12/2008 | Zeldis |
| 7,524,961 B2 | 4/2009 | Filliers et al. |
| 7,572,916 B2 | 8/2009 | Filliers et al. |
| 7,932,036 B1 | 4/2011 | Raponi et al. |
| 7,943,635 B2 | 5/2011 | Angibaud et al. |

(Continued)

FOREIGN PATENT DOCUMENTS

| | | |
|---|---|---|
| WO | WO 1994/010138 A1 | 5/1994 |
| WO | WO 1997/021701 A1 | 6/1997 |

(Continued)

OTHER PUBLICATIONS

Kim et al. (Treatment of Metastatic Head and Neck Cancer: Chemotherapy and Novel Agents, p. 295-314, 2003) (Year: 2003).*

(Continued)

*Primary Examiner* — Theodore R. Howell
(74) *Attorney, Agent, or Firm* — Jones Day

(57) ABSTRACT

The present invention relates to the field of molecular biology and cancer biology. Specifically, the present invention relates to methods of treating a subject with a farnesyltransferase inhibitor (FTI) that include determining whether the subject is likely to be responsive to the FTI treatment based on HRAS mutation status in the subject.

34 Claims, 3 Drawing Sheets

Specification includes a Sequence Listing.

(56) References Cited

U.S. PATENT DOCUMENTS

| | | | |
|---|---|---|---|
| 8,318,753 | B2 | 11/2012 | Venet et al. |
| 8,329,714 | B2 | 12/2012 | Venet et al. |
| 9,707,221 | B2 | 7/2017 | Gualberto et al. |
| 10,022,364 | B2 | 7/2018 | Gualberto et al. |
| 10,292,979 | B2 | 5/2019 | Gualberto et al. |
| 10,335,404 | B2 | 7/2019 | Gualberto et al. |
| 10,471,055 | B2 | 11/2019 | Gualberto et al. |
| 2002/0034725 | A1 | 3/2002 | McKenna et al. |
| 2003/0027839 | A1 | 2/2003 | Palmer et al. |
| 2003/0114471 | A1 | 6/2003 | Venet et al. |
| 2004/0044032 | A1 | 3/2004 | End et al. |
| 2004/0110769 | A1 | 6/2004 | End |
| 2004/0157773 | A1 | 8/2004 | End |
| 2004/0157882 | A1 | 8/2004 | End et al. |
| 2004/0192726 | A1 | 9/2004 | Palmer et al. |
| 2006/0111398 | A1 | 5/2006 | Fourie |
| 2007/0048782 | A1 | 3/2007 | Raponi |
| 2007/0093449 | A1 | 4/2007 | De Porre et al. |
| 2009/0018164 | A1 | 1/2009 | Palmer et al. |
| 2009/0023776 | A1 | 1/2009 | End |
| 2009/0042935 | A1 | 2/2009 | De Porre et al. |
| 2009/0311344 | A1 | 12/2009 | Yurkow et al. |
| 2011/0098318 | A1 | 4/2011 | Palmer et al. |
| 2011/0105557 | A1 | 5/2011 | End |
| 2011/0195419 | A1 | 8/2011 | Fourie |
| 2012/0108634 | A1 | 5/2012 | End |
| 2012/0196766 | A1 | 8/2012 | Fourie |
| 2013/0130999 | A1 | 5/2013 | Vener et al. |
| 2017/0051356 | A1 | 2/2017 | Gualberto et al. |
| 2017/0304291 | A1 | 10/2017 | Gualberto et al. |
| 2018/0092903 | A1 | 4/2018 | Gualberto et al. |
| 2018/0187266 | A1 | 7/2018 | Gualberto et al. |
| 2018/0280376 | A1 | 10/2018 | Gualberto et al. |

FOREIGN PATENT DOCUMENTS

| | | | | |
|---|---|---|---|---|
| WO | WO 1997/030992 | A1 | 8/1997 | |
| WO | WO 1998/028303 | A1 | 7/1998 | |
| WO | WO 1998/055124 | A1 | 12/1998 | |
| WO | WO 1999/045712 | A1 | 9/1999 | |
| WO | WO 1999/045912 | A1 | 9/1999 | |
| WO | WO 2000/001386 | A1 | 1/2000 | |
| WO | WO 2000/001691 | A1 | 1/2000 | |
| WO | WO 2000/012498 | A1 | 3/2000 | |
| WO | WO 2000/012499 | A1 | 3/2000 | |
| WO | WO 2000/039082 | A2 | 7/2000 | |
| WO | WO 2001/056552 | A2 | 8/2001 | |
| WO | WO 2001/062234 | A2 | 8/2001 | |
| WO | WO 2001/098302 | A1 | 12/2001 | |
| WO | WO 2002/043733 | A1 | 6/2002 | |
| WO | WO 2002/064142 | A1 | 8/2002 | |
| WO | WO 2002/072574 | A1 | 9/2002 | |
| WO | WO 2002/085364 | A1 | 10/2002 | |
| WO | WO 2003/080058 | A1 | 10/2003 | |
| WO | WO 2005/105782 | A1 | 11/2005 | |
| WO | WO 2005/105783 | A1 | 11/2005 | |
| WO | WO 2005/105784 | A1 | 11/2005 | |
| WO | WO 2006/052718 | A2 | 5/2006 | |
| WO | WO 2007/110709 | A2 | 10/2007 | |
| WO | WO 2009/148954 | A2 | 12/2009 | |
| WO | WO 2012/016021 | A2 | 2/2012 | |
| WO | WO 2014/160130 | A1 | 10/2014 | |
| WO | WO 2015/164862 | A1 | 10/2015 | |
| WO | WO-2015164862 | A1 * | 10/2015 | ........... C12Q 1/6886 |
| WO | WO 2017/031101 | A1 | 2/2017 | |
| WO | WO 2018/085518 | A2 | 5/2018 | |

OTHER PUBLICATIONS

Egloff et al. (Journal of Oncology, 2009, 1-12) (Year: 2009).*

Advani et al., "Treatment of refractory and relapsed acute myelogenous leukemia with combination chemotherapy plus the multidrug resistance modulator PSC 833 (valspodar)," Blood, 93(3):787-795 (1999).

Alsina et al., "Farnesyltransferase inhibitor tipifarnib is well tolerated, induces stabilization of disease, and inbibits farnesylation and oncogenic/tumor survival pathways in patients with advanced multiple myeloma," Blood, 103(9):3271-3277 (2004).

Anderson et al., "Prevalence of RAS oncogene mutation in head and neck carcinomas," J. Otolaryngol., 21:321-326 (1992).

Anderson et al., "H-ras oncogene mutation and human papillomavirus infection in oral carcinomas," Arch. Otolaryngol. Head Neck Surg., 120(7):755-760 (1994).

Anderson et al., "Risk of myeloid malignancies in patients with autoimmune conditions," Br. J Cancer, 100:822-828 (2009).

Anonymous, "History of Changes for Study NCT02383927 Phase II Study of Tipifarnib in Squamous Head and Neck Cancer with HRAS Mutations," U.S. National Library of Medicine, pp. 1-8, Sep. 12, 2016.

Apples et al., "Development of farnesyl transferase inhibitors: A review," Oncologist, 10:565-578 (2005).

Berndt et al., "Targeting protein prenylation for cancer therapy," Nat. Rev. Cancer, 11(11):775-791 (2011).

Brahmer et al., "Nivolumab in patients with advanced non-small-cell lung cancer," Asia Pac. J Clin. Oncol., 10:Abstract 299 (2014).

Braig et al., "Liquid biopsy monitoring uncovers acquired RAS-mediated resistance to cetuximab in a substantial proportion of patients with head and neck squamous cell carcinoma," Oncotarget., 7(28):42988-42995 (2016).

Cancer Genome Atlas Network, "Comprehensive genomic characterization of head and neck squamous cell carcinomas," Nature, 517(7536):576-582 (2015).

Cathcart-Rake et al., "Elderly Former Smoker with HRAS Mutant Non-Small-Cell Lung Cancer," J. Thorac. Oncol., 9(10):e75-e78 (2014).

Chen et al., "Transformation by HrasG12V is consistently associated with mutant allele copy grains and is reversed by farnesyl transferase inhibition," Oncogene, 33(47):5442-5449 (2013).

Cheng et al., "Memorial Sloan Kettering-Integrated Mutation Profiling of Actionable Cancer Targets (MSK-IMPACT): A Hybridization Capture-Based Next-Generation Sequencing Clinical Assay for Solid Tumor Molecular Oncology," J. Mol. Diagn., 17(3):251-264 (2015).

Cox et al., "Farnesyltransferase inhibitors and cancer treatment: targeting simply RAS?," Biochim. Biophys. Acta. 1333(1):F51-71 (1997).

Duez et al., "Towards the synthesis of bisubstrate inhibitors of protein farnesyltransferase: Synthesis and biological evaluation of new farnesylpyrophosphate analogues," Biorg. Med. Chem., 18:543-556 (2010).

Fenaux et al., "A multicenter phase 2 study of the farnesyltransferase inhibitor tipifarnib in intermediate- to high-rish myelodysplastic syndrome," Blood, 109(10): 4158-4163 (2007).

Gridelli et al., "An international, multicenter, randomized phase III study of first-line erlotinib followed by second-line cisplatin/gemcitabine versus first-line cisplatin/gemcitabine followed by second-line erlotinib in advanced non-small-cell lung cancer: treatment rationale and protocol dynamics of the TORCH trial," Clin. Lung Cancer, 9(4):235-238 (2008).

Hamada et al., "Liver metastasis models of colon cancer for evaluation of drug efficacy using NOD/Shi-scid IL2R gamma(null) (NOG) mice," Int. J Oncol., 32(1):153-159 (2008).

Hanrahan et al., "A phase II study of Lonafarnib (SCH66336) in patients with chemorefractory, advanced squamous cell carcinoma of the head and neck," Am. J. Clin. Oncol., 32(3):274-279 (2009).

Harousseau et al., "A randomized phase 3 study of tipifarnib compared with best supportive care, including hydroxyurea, in the treatment of newly diagnosed acute myeloid leukemia in patients 70 years or older," Blood, 114(6):1166-1173 (2009).

Herreros-Villanueva et al., "KRAS mutatations: Analytical considerations," Clinica Chimica Acta, 431:211-220 (2014).

Ho et al., "An open-label, phase II study of tipifarnib for the treatment of HRAS mutant solid tumors, including squamous cell carcinomas of the head and neck," J. Clin. Oncol., 35(15):Supp. Supplement 1 (2017).

Ibrahim et al., "PD-L1 Blockade for Cancer Treatment: MEDI4736," Seminars in Oncology, 42(3):474-483 (2015).

(56) References Cited

OTHER PUBLICATIONS

India Project Team of the International Cancer Genome Consortium, "Mutational landscape of gingivo-buccal oral squamous cell carcinoma reveals new recurrently-mutated genes and molecular subgroups," *Nat. Commun.*, 4:2873 (2013).
Kamasani et al., "mDia function is critical for the cell suicide program triggered by farnesyl transferase inhibition," *Cancer Biol. Ther.*, 6:1418-1423 (2007).
Karp et al., "Clinical and biologic activity of the farnesyltransferase inhibitor R115777 in adults with refractory and relapsed acute leukemias: a phase 1 clinical-laboratory correlative trial," *Blood*, 97:3361-3369 (2001).
Kim et al., "Novel therapeutics for head and neck cancer," *Curr. Opin. Oncol.*, 14:334-342 (2002).
Kirschbaum, "A phase 1 trial dose-escalation study of tipifarnib on a week-on, week-off schedule in relapsed, refractory or high-risk myeloid leukemia," *Leukemia*, 25(10):1543-47 (2011).
Klass et al., "Antitumor effects of combined bortezomib and tipifarnib in head and neck squamous cell carcinoma (HNSCC) cells," *J. Clin. Oncol.*, 24(18):5581 (2006).
Kohl et al., "Protein farnesyltransferase inhibitors block the growth of ras-dependent tumors in nude mice," *PNAS*, 91:9141-9145 (1994).
Kumar et al., "Receiver operating characteristics (ROC) curve for medical researchers," *Indian Pediatrics*, 48:277-287 (2011).
Kurzrock et al., "Farnesyltransferase inhibitor R115777 in myelodysplastic syndrome: Clinical and biologic activities in the phase 1 setting," *Blood*, 102(13): 4527- 4534 (2003).
Kurzrock et al., "Phase I study of alternate-week administration of tipifarnib in patients with myelodysplastic syndrome," *Clin. Cancer Res.*, 14(2):509-514 (2008).
Lancet et al., "A phase 2 study of the farnesyltransferase inhibitor tipifarnib in poor-risk and elderly patients with previously untreated acute myelogenous leukemia," *Blood*, 109:1387-1394 (2007).
Lancet et al., "Phase 2 trial of the Farnesyltransferase inhibitor tipifarnib in previously untreated older adults with AML and baseline presence of a specific 2-Gene expression signature ratio," *Blood*, 120: Abstract 1508 (2012).
Lara et al., "Intermittent dosing of the farnesyl transferase inhibitor tipifarnib (R115777) in advanced malignant solid tumors: a phase I California Cancer Consortium Trial," *Anticancer Drugs*, 16(3):317-321 (2005).
Lee et al., "Development of tripeptidyl farnesyltransferase inhibitors," *Bioorg. Med. Chem. Lett.*, 12:1599-1602 (2002).
Ley et al., "Genomic and epigenomic landscapes of adult de novo acute myeloid leukemia," *N. Engl. J. Med.*, 368(22):2059-2074 (2013).
Lubet et al., "Effects of the farnesyl transferase inhibitor R115777 (Zarnestra) on mammary carcinogenesis: prevention, therapy, and role of HaRas mutations," *Mol. Cancer. Ther.*, 5(4):1073-1078 (2006).
Ma et al., "A two-gene expression ratio predicts clinical outcome in breast cancer patients treated with tamoxifen," *Cancer Cell*, 5:607-16 (2004).
Martinelli et al., "Farnesyltransferase inhibition in hematologic malignancies: The clinical experience with tipifarnib," *Clin. Adv. Hematol. Oncol.*, 6(4):303-310 (2008).
Mesa et al., "Tipifarnib: farnesyl transferase inhibition at a crossroads," *Expert Rev. Anticancer Ther.*, 6(3):313-319 (2006).
Minic et al., "Ras gene mutations in patients with non-small cell lung carcinoma," *Arch. Oncol.*, 12(2):95-99 (2004).
Oh et al, "Identification of insulin-like growth factor binding protein-3 as a farnesyl transferase inhibitor SCH66336-induced negative regulator of angiogenesis in head and neck squamous cell carcinoma," *Clin. Cancer Res.*, 12(2):653-661 (2006).
Perez-Ruixo et al., "Exposure-toxicity relationships for tipifarnib in cancer patients," *Br. J. Clin. Pharmacol.*, 64(2):219-232 (2007).
Philips et al., "Therapeutics uses of anti-PD-1 and anti-PD-L1 antibodies," *International Immunol.*, 27(1):39-46 (2014).

Price et al., "Current Treatment Options for Metastatic Head and Neck Cancer," *Curr. Treat. Options Oncol.*, 13:35-46 (2012).
Rao et al., "Phase III double-blind placebo-controlled study of farnesyl transferase inhibitor R115777 in patients with refractory advanced colorectal cancer," *Clin. Oncol.*, 22:3950-3957 (2004).
Raponi et al., "Identification of molecular predictors of response in a study of tipifarnib treatment in relapsed and refractory acute myelogenous leukemia," *Clin. Cancer Res.*, 13(7):2254-2260 (2007).
Raponi et al., "A 2-gene classifier for predicting response to the farnesyltransferase inhibitor tipifarnib in acute myloid leukemia," *Blood*, 111(5):2589-2596 (2008).
RASH_HUMAN (P01112.1 http://www.ncbi.nlm.nih.gov/proetin/P01112.1, Nov. 30, 2016).
Rennel et al., "Regulation of endothelial cell differentiation and transformation by H-Ras," *Exp. Cell Res.*, 291(1):189-200 (2003).
Rolland et al., "Phase II trial and prediction of response of single agent tipifarnib in patients with relapsed/refractory mantle cell lymphoma: a Groupe d'Etude des Lymphomes de l'Adulte trial," *Cancer Chemother. Pharmacol.*, 65(4):781-790 (2009).
Saranth et al., "High frequency mutation in codons 12 and 61 of H-ras oncogene in chewing tobacco-related human oral carcinoma in India," *Br. J Cancer*, 63:573-578 (1991).
Sheffield et al., "Fatal congenital hypertrophic cardiomyopathy and a pancreatic nodule morphologically identical to focal lesion of congenital hyperinsulinism in an infant with costello syndrome: case report and review of the literature," *Pediatr. Dev. Pathol.*, 18:237-244 (2015).
Shen et al., "Farnesyltransferase and geranylgeranyltransferase: Structures, mechanism, inhibitors and molecular modeling," *Drug Discov. Today*, 20(2):267-276 (2015).
Shi et al., "Farnesyltransferase inhibitor effects on prostate tumor micro-environment and radiation survival," *Prostate*, 62(1):69-82 (2005).
Tannock et al., "Experimental Chemotherapy," in *The Basic Science of Oncology* (Tannock, Ed.), ch. 19: 338, 352-359, McGraw-Hill, New York (1992).
Thomas et al., "Tipifarnib in the treatment of acute myeloid leukemia," *Biologics*, 1(4):415-424 (2007).
United States Patent and Trademark Office, Office Action issued in U.S. Appl. No. 15/238,458, dated May 21, 2018.
United States Patent and Trademark Office, Office Action issued in U.S. Appl. No. 15/346,675, dated Jan. 18, 2017.
United States Patent and Trademark Office, Office Action issued in U.S. Appl. No. 15/346,675, dated May 22, 2017.
United States Patent and Trademark Office, Notice of Allowance issued in U.S. Appl. No. 15/346,675, dated Jun. 7, 2017.
United States Patent and Trademark Office, Office Action issued in U.S. Appl. No. 15/643,387, dated Sep. 8, 2017.
United States Patent and Trademark Office, Office Action issued in U.S. Appl. No. 15/643,387, dated Feb. 5, 2018.
United States Patent and Trademark Office, Notice of Allowance issued in U.S. Appl. No. 15/643,387, dated May 29, 2018.
United States Patent and Trademark Office, Office Action issued in U.S. Appl. No. 15/844,478, dated Jan. 12, 2018.
United States Patent and Trademark Office, Office Action issued in U.S. Appl. No. 15/844,478, dated Jun. 28, 2018.
United States Patent and Trademark Office, Office Action issued in U.S. Appl. No. 15/905,711, dated May 21, 2018.
Vachtenheim et al., "Mutations of K-ras oncogene and absence of H-ras mutations in squamous cell carcinomas of the lung," *Clin. Cancer Res.*, 1:359-365 (1995).
VELCADE® (bortezomib), "How VELCADE works," (http://www.velcade.com/understanding-velcade/about-velcade downloaded May 18, 2017).
Vigneswaran et al., "Silencing of cystatin M in metastatic oral cancer cell line MDA-686Ln by siRNA increases cysteine proteinases and legumain activities, cell proliferation and in vitro invasion," *Life Sciences*, 78:898-907 (2006).
Yao et al., "Efficacy of the farnesyltransferase inhibitor R115777 in a rat mammary tumor model: Rold or Ha-ras mutations and use of microarray analysis in identifying potential targets," *Carcinogenesis*, 27(7):1420-1431 (2006).

(56) References Cited

OTHER PUBLICATIONS

Yokota et al., "Are KRAS/BRAF Mutations Potent Prognostic and/or Predictive Biomarkers in Colorectal Cancers?" *Anticancer Agents Med. Chem.*, 12:163-171 (2012).
Zanaruddin et al., "Common Oncogenic Mutations Are Infrequent in Oral Squamous Cell Carcinoma of Asian Origin," *PLoS One*, 8(11):e80229 (2013).
Zujewski et al., "Phase I and pharmacokinetic study of farnesyl protein transferase inhibitor R115777 in advanced cancer," *J. Clin. Oncol.*, 18(4): 927-941 (2000).
Awada et al., "A phase I clinical and pharmacokinetic study of tipifarnib in combination with docetaxel in patients with advanced solid malignancies," *Curr. Med. Res. Opin.*, 23(5):991-1003 (2007).
Garrido-Laguna et al., "Patients with advanced head and neck cancers have similar progression-free survival on phase I trials and their last food and drug administration-approved treatment," *Clin. Cancer Res.*, 16(15):4031-4037 (2010).
Ho et al., "Preliminary Results from a Phase 2 Trial of Tipifarnib in HRAS mutant Head and Neck Squamous Cell Carcinomas," Abstract 217, 2018 Multidisciplinary Head and Neck Cancers Symposium.
Kura Oncology, "Preliminary Results from a Phase 2 Trial of Tipifarnib in HRAS mutant Head & Neck Squamous Cell Carcinomas (HNSCC)," Poster Presentation, 2018 Head and Neck Cancer Symposium.
Misso et al., "Pharmacological Inhibition of HSP90 and ras Activity as a New Strategy in the Treatment of HNSCC," *J. Cell. Physiol.*, 228(1):130-141 (2013).
Perri et al., "Radioresistance in head and neck squamous cell carcinoma: Biological bases and therapeutic implications," *Head Neck*, 37(5):763-770 (2015).
Saki et al., "Acquired resistance to cetuximab is associated with the overexpression of Ras family members and the loss of radiosensitization in head and neck cancer cells," *Radiother. Oncol.*, 108(3):473-478 (2013).
Scully et al., "Oral squamous cell carcinoma overview," *Oral. Oncol.*, 45(4-5):301-308 (2009).
United States Patent and Trademark Office, Office Action issued in U.S. Appl. No. 15/238,458, dated Nov. 13, 2018.
United States Patent and Trademark Office, Office Action issued in U.S. Appl. No. 15/844,478, dated Nov. 5, 2018.
United States Patent and Trademark Office, Notice of Allowance issued in U.S. Appl. No. 15/844,478, dated Mar. 4, 2019.
United States Patent and Trademark Office, Office Action issued in U.S. Appl. No. 15/905,711, dated Nov. 19, 2018.
United States Patent and Trademark Office, Notice of Allowance issued in U.S. Appl. No. 15/905,711, dated Mar. 5, 2019.
Bowen et al., "RAS mutation in acute myeloid leukemia is associated with distinct cytogenetic subgroups but does not influence outcome in patients younger than 60 years," *Blood*, 106(6):2113-2119 (2005).
Liang et al., "Biomarkers of HPV in Head and Neck Squamos Cell Carcinoma," *Cancer Res.*, 72(19):5004-5013 (2012).
O'Leary et al., "Molecular analysis of ras oncogenes in CIN III and in stage I and II invasive squamous cell carcinoma of the uterine cervix," *J. Clin. Pathol.*, 51:576-582 (1998).
United States Patent and Trademark Office, Notice of Allowance issued in U.S. Appl. No. 15/238,458, dated Aug. 28, 2019.
United States Patent and Trademark Office, Notice of Allowance issued in U.S. Appl. No. 15/844,478, dated Apr. 23, 2019.

United States Patent and Trademark Office, Office Action issued in U.S. Appl. No. 15/238,458, dated May 31, 2019.
Downward, "Targeting RAS signalling pathways in cancer therapy," *Nat. Rev. Cancer*, 3(1):11-22 (2003).
Oh et al., "A multiplicity of anti-invasice effects of farnesyl transferase inhibitor SCH66336 in human head and neck cancer," *Intl. J. Cancer*, 131(3):537-547 (2012).
Rhee et al., "Advances in Chemoprevention of Head and Neck Cancer," *Oncologist*, 9(3):302-311 (2004).
Stransky et al., "The mutational landscape of head and neck squamous cell carcinoma," *Science*, 333:1157-1160 (2011).
United States Patent and Trademark Office, Office Action issued in U.S. Appl. No. 16/007,931, dated Jun. 5, 2020.
U.S. Appl. No. 15/238,458, filed Aug. 16, 2016, US 2017-0051356, Feb. 23, 2017, Methods of Treating Cancer Patients With Farnesyltransferase Inhibitors.
U.S. Appl. No. 15/346,675, filed Nov. 8, 2016, US 2017-0071931, Mar. 16, 2017, Methods of Treating Cancer Patients With Farnesyltransferase Inhibitors, U.S. Pat. No. 9,707,221, Jul. 18, 2017.
U.S. Appl. No. 15/643,387, filed Jul. 6, 2017, US 2017-0304291, Oct. 26, 2017, Methods of Treating Cancer Patients With Farnesyltransferase Inhibitors, U.S. Pat. No. 10,022,364, Jul. 17, 2018.
U.S. Appl. No. 15/844,478, filed Dec. 15, 2017, US 2018/0092903, Apr. 5, 2018, Methods of Treating Cancer Patients With Farnesyltransferase Inhibitors.
U.S. Appl. No. 15/905,711, filed Feb. 26, 2018, US 2018-0193329, Jul. 12, 2018, Methods of Treating Cancer Patients With Farnesyltransferase Inhibitors.
U.S. Appl. No. 16/007,931, filed Jun. 13, 2018, US 2018-0280376, Oct. 4, 2018, Methods of Treating Cancer Patients With Farnesyltransferase Inhibitors.
Wei et al., "Research Progress in Individualized Treatment of Lung Squamous Cell Carcinoma," Chinese Journal of Clinical Oncology and Rehabilitation. vol. 21, No. 1, pp. 117-119, Jan. 2014. (Chinese document with English abstract).
Bell et al.," Design and Biological Activity of (S)-4-(5-{ [1-(3-Chlorobenzyl)-2-oxopyrrolidin-3-C03 ylamino ]methyl }imidazol-1-ylmethyl)benzonitrile, a 3-Aminopyrrolidinone Farnesyltransferase Inhibitor with Excellent Cell Potency," J Med. Chem. 44(18): 2933-2949 (2001).
Egloff et al., "Improving Response Rated to EGFR-Targeted Therapies for Head and Neck CO3 Squamous Cell Carcinoma: Candidate Predictive Biomarkers and Combination Treatment with Src Inhibitors," J. Oncol., 896407:1-12 (2009).
Hida, T., "Targeted therapies for the treatment oflung cancer," Jpn J Cancer Clin., 49(10): 1107-1117 (2003) (Japanese document with English abstract).
Kim et al., "Treatment of Metastatic Head and Neck Cancer: Chemotherapy and Novel Agents," CO4 Head and Neck Cancer, Brockstein et al. eds., Kluwer Academic Publishers, New York, pp. 295-314 (2003).
Liu et al., "Targeting the protein prenyltransferases efficiently reduces tumor development in mice withK-RAS-induced lung cancer," PNAS, 107(14):6471-6476 (2010).
Prior et al., "A comprehensive survey of Ras mutations in cancer," Cancer Res. 72(10): 2457-2467 CO2 (2012).
Saito et al., "MicroRNAs in Hepatobiliary and Pancreatic Cancers," Front Genet. 2(66): 1-5 (2011).

\* cited by examiner

A
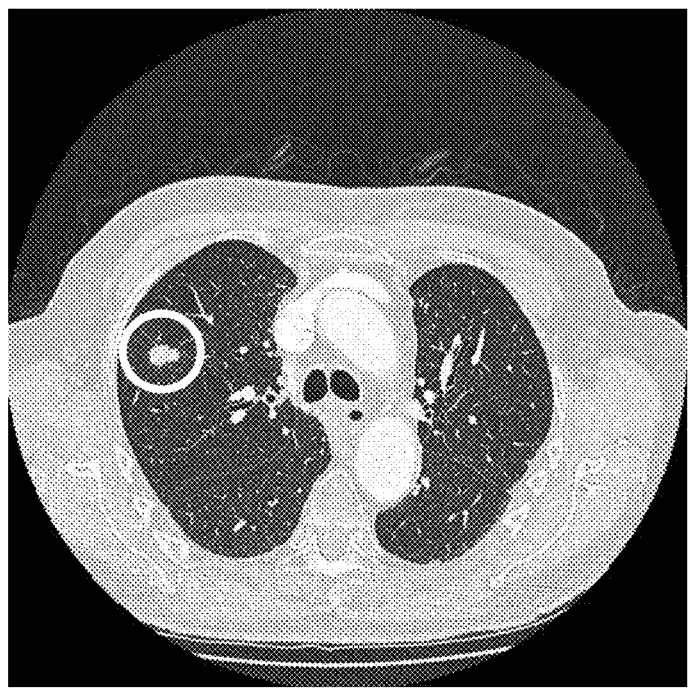
B
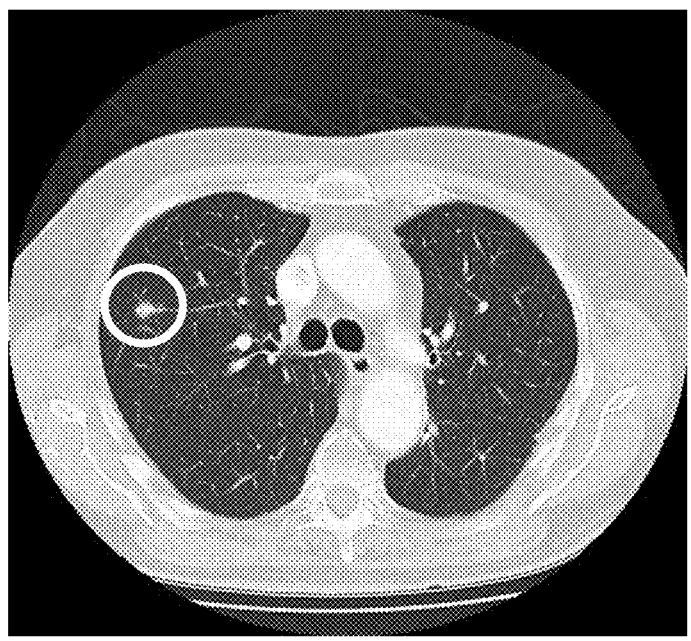
FIG. 1A-B

SEQUENCE LISTING

<160> NUMBER OF SEQ ID NOS: 2

<210> SEQ ID NO 1
<211> LENGTH: 189
<212> TYPE: PRT
<213> ORGANISM: Homo sapiens
<220> FEATURE:
<223> OTHER INFORMATION: human HRAS

<400> SEQUENCE: 1

```
Met Thr Glu Tyr Lys Leu Val Val Val Gly Ala Gly Gly Val Gly Lys
1               5                   10                  15

Ser Ala Leu Thr Ile Gln Leu Ile Gln Asn His Phe Val Asp Glu Tyr
            20                  25                  30

Asp Pro Thr Ile Glu Asp Ser Tyr Arg Lys Gln Val Val Ile Asp Gly
        35                  40                  45

Glu Thr Cys Leu Leu Asp Ile Leu Asp Thr Ala Gly Gln Glu Glu Tyr
    50                  55                  60

Ser Ala Met Arg Asp Gln Tyr Met Arg Thr Gly Glu Gly Phe Leu Cys
65                  70                  75                  80

Val Phe Ala Ile Asn Asn Thr Lys Ser Phe Glu Asp Ile His Gln Tyr
                85                  90                  95

Arg Glu Gln Ile Lys Arg Val Lys Asp Ser Asp Asp Val Pro Met Val
            100                 105                 110

Leu Val Gly Asn Lys Cys Asp Leu Ala Ala Arg Thr Val Glu Ser Arg
        115                 120                 125

Gln Ala Gln Asp Leu Ala Arg Ser Tyr Gly Ile Pro Tyr Ile Glu Thr
    130                 135                 140

Ser Ala Lys Thr Arg Gln Gly Val Glu Asp Ala Phe Tyr Thr Leu Val
145                 150                 155                 160

Arg Glu Ile Arg Gln His Lys Leu Arg Lys Leu Asn Pro Pro Asp Glu
                165                 170                 175

Ser Gly Pro Gly Cys Met Ser Cys Lys Cys Val Leu Ser
            180                 185
```

<210> SEQ ID NO 2
<211> LENGTH: 570
<212> TYPE: DNA
<213> ORGANISM: Homo sapiens
<220> FEATURE:
<223> OTHER INFORMATION: human HRAS

```
<400> SEQUENCE: 2
atgacggaat ataagctggt ggtggtgggc gccggcggtg tgggcaagag tgcgctgacc        60
atccagctga tccagaacca ctttgtggac gaatacgacc ccactataga ggattcctac       120
cggaagcagg tggtcattga tggggagacg tgcctgttgg acatcctgga taccgccggc       180
caggaggagt acagcgccat gcgggaccag tacatgcgca ccggggaggg cttcctgtgt       240
gtgtttgcca tcaacaacac caagtctttt gaggacatcc accagtacag ggagcagatc       300
aaacgggtga aggactcgga tgacgtgccc atggtgctgg tggggaacaa gtgtgacctg       360
gctgcacgca ctgtggaatc tcggcaggct caggacctcg cccgaagcta cggcatcccc       420
tacatcgaga cctcggccaa gacccggcag ggagtggagg atgccttcta cacgttggtg       480
cgtgagatcc ggcagcacaa gctgcggaag ctgaaccctc ctgatgagag tggccccggc       540
tgcatgagct gcaagtgtgt gctctcctga                                        570
```

METHODS OF TREATING CANCER PATIENTS WITH FARNESYLTRANSFERASE INHIBITORS

This application claims the benefit of U.S. Provisional Patent Application No. 62/417,044, filed on Nov. 3, 2016, which is incorporated by reference herein in its entirety.

FIELD

The present invention relates to the field of molecular biology and cancer biology. Provided herein are methods of using HRAS mutations biomarkers for predicting clinical sensitivity and therapeutic response to treatment with a farnesyltransferase inhibitor in a subject having a squamous cell head and neck cancer or squamous cell lung cancer that has not yet been treated with an EGFR inhibitor or that is refractory to treatment with an EGFR inhibitor. Further provided herein are kits for carrying out these methods.

BACKGROUND

Stratification of patient populations to improve therapeutic response rate is increasingly valuable in the clinical management of cancer patients. Farnesyltransferase inhibitors (FTI) are therapeutic agents that have utility in the treatment of cancers, such as leukemia, lymphoma and certain solid tumors. However, different patients may respond differently to an FTI treatment. Therefore, methods to predict the responsiveness of a cancer patient to an FTI treatment, or methods to select patients for an FTI treatment represent unmet needs. The methods and compositions of the present invention meet these needs and provide other related advantages.

SUMMARY OF THE INVENTION

Provided herein are methods for population selection of head and neck cancer patients for treatment with an FTI. The methods provided herein are based, in part, on the discovery that the mutant status of HRAS and/or resistance of said cancer to EGFR inhibitors can be used to predict responsiveness of a head and neck cancer patient to an FTI treatment.

Provided herein are methods of treating EGFR inhibitor-refractory squamous cell carcinoma of the head and neck (SCCHN), wherein the SCCHN has an HRAS mutation, comprising administering to the subject a farnesyltransferase inhibitor (FTI). In certain embodiments, said HRAS mutation comprises an amino acid substitution at a codon selected from a group consisting of G12, G13, Q61, Q22, K117, A146 and any combination thereof. In certain embodiments, said SCCHN does not have K-Ras mutation or N-Ras mutation. In certain embodiments, said SCCHN has an amplified HRAS gene or overexpresses the HRAS mRNA and/or protein. In certain embodiments, said SCCHN has wild type K-Ras and wild type N-Ras. In certain embodiments, said SCCHN is HPV negative. In certain embodiments, said SCCHN is HPV positive. In certain embodiments, said SCCHN is at an advanced stage or metastatic. In certain embodiments, said SCCHN is relapsed SCCHN. In specific embodiments, the SCCHN is SCCHN of the trachea. In specific embodiments, the SCCHN is SCCHN of the maxilla. In specific embodiments, the SCCHN is SCCHN of the oral cavity. In certain embodiments, the EGFR inhibitor is cetuximab. In certain embodiments, the FTI is tipifarnib.

Provided herein are methods of treating a squamous cell carcinoma of the head and neck (SCCHN or HNSCC) in a subject, wherein the SCCHN is refractory to an EGFR inhibitor, comprising (a) determining the presence or absence of a HRAS mutation in a sample from said subject, and subsequently (b) administering a therapeutically effective amount of a farnesyltransferase inhibitor (FTI) to said subject if said sample is determined to have a HRAS mutation. Also provided herein are methods of treating a squamous cell carcinoma of the head and neck (SCCHN) in a subject, wherein the subject has never been treated with an EGFR inhibitor, comprising (a) determining the presence or absence of a HRAS mutation in a sample from said subject, and subsequently (b) administering a therapeutically effective amount of a farnesyltransferase inhibitor (FTI) to said subject if said sample is determined to have a HRAS mutation and not administering an EGFR inhibitor. In certain embodiments, said HRAS mutation comprises an amino acid substitution at a codon selected from a group consisting of G12, G13, Q61, Q22, K117, A146, and any combination thereof. In certain embodiments, said FTI is administered in combination with chemotherapy. In certain embodiments, said chemotherapy comprises a platinum-based therapy, a taxane, or a combination thereof.

In certain embodiments, the methods further comprise determining the presence or absence of a K-Ras mutation or a N-Ras mutation, wherein said sample does not have K-Ras mutation or N-Ras mutation. In certain embodiments, said sample has wild type K-Ras and wild type N-Ras. In specific embodiments, the sample is a tissue biopsy. In specific embodiments, the sample is a tumor biopsy. In specific embodiments, wherein determining the presence or absence of a Ras mutation comprising analyzing nucleic acids obtained from said sample.

In certain embodiments, Ras mutation is determined by sequencing, Polymerase Chain Reaction (PCR), DNA microarray, Mass Spectrometry (MS), Single Nucleotide Polymorphism (SNP) assay, denaturing high-performance liquid chromatography (DHPLC), or Restriction Fragment Length Polymorphism (RFLP) assay. In specific embodiments, Ras mutation is determined by PCR. In specific embodiments, Ras mutation is determined by sequencing. In specific embodiments, determining the presence or absence of a Ras mutation comprising analyzing proteins obtained from said sample.

In certain embodiments, said SCCHN is HPV negative. In certain embodiments, said SCCHN is HPV positive. In certain embodiments, said SCCHN is at an advanced stage or metastatic. In certain embodiments, said SCCHN is relapsed SCCHN. In certain embodiments, the SCCHN is SCCHN of the trachea. In certain embodiments, the SCCHN is SCCHN of the maxilla. In certain embodiments, the SCCHN is SCCHN of the oral cavity.

In certain embodiments, the EGFR inhibitor is cetuximab. In certain embodiments, the EGFR inhibitor is erlotinib. In certain embodiments, the EGFR inhibitor is gefitinib. In certain embodiments, the EGFR inhibitor is panitumumab. In certain embodiments, the farnesyltransferase inhibitor (FTI) is tipifarnib.

In some embodiments, provided herein is a method of treating a SCCHN in a subject based on the presence of an HRAS mutation. In some embodiments, the SCCHN can be HPV negative SCCHN. In some embodiments, the SCCHN can be HPV positive SCCHN. In some embodiments, the SCCHN can be relapsed/recurrent SCCHN. In some embodiments, the SCCHN can be metastatic SCCHN. The methods provided herein include (a) determining the presence or absence of a HRAS mutation in a sample from the subject having SCCHN, and subsequently (b) administering a therapeutically effective amount of tipifarnib to the subject if the sample is determined to have a HRAS mutation. In certain embodiments, said tipifarnib is administered in combination with chemotherapy. In certain embodiments, said chemotherapy comprises a platinum-based therapy, a taxane, or a combination thereof.

Provided herein are methods of treating EGFR inhibitor-refractory lung squamous cell carcinoma (lung SCC), wherein the lung SCC has an HRAS mutation, comprising administering to the subject a farnesyltransferase inhibitor (FTI). In certain embodiments, said HRAS mutation comprises an amino acid substitution at a codon selected from a group consisting of G12, G13, Q61, Q22, K117, A146 and any combination thereof. In certain embodiments, said lung SCC does not have K-Ras mutation or N-Ras mutation. In certain embodiments, said lung SCC has an amplified HRAS gene or overexpresses the HRAS mRNA and/or protein. In certain embodiments, said lung SCC has wild type K-Ras and wild type N-Ras. In certain embodiments, said lung SCC is HPV negative. In certain embodiments, said lung SCC is HPV positive. In certain embodiments, said lung SCC is at an advanced stage or metastatic. In certain embodiments, said lung SCC is relapsed lung SCC. In certain embodiments, the EGFR inhibitor is cetuximab. In certain embodiments, the FTI is tipifarnib.

Provided herein are methods of treating a lung squamous cell carcinoma (lung SCC) in a subject, wherein the lung SCC is refractory to an EGFR inhibitor, comprising (a) determining the presence or absence of a HRAS mutation in a sample from said subject, and subsequently (b) administering a therapeutically effective amount of a farnesyltransferase inhibitor (FTI) to said subject if said sample is determined to have a HRAS mutation. Also provided herein are methods of treating a lung SCC in a subject, wherein the subject has never been treated with an EGFR inhibitor, comprising (a) determining the presence or absence of a HRAS mutation in a sample from said subject, and subsequently (b) administering a therapeutically effective amount of a farnesyltransferase inhibitor (FTI) to said subject if said sample is determined to have a HRAS mutation and not administering an EGFR inhibitor. In certain embodiments, said HRAS mutation comprises an amino acid substitution at a codon selected from a group consisting of G12, G13, Q61, Q22, K117, A146, and any combination thereof. In certain embodiments, said FTI is administered in combination with chemotherapy. In certain embodiments, said chemotherapy comprises a platinum-based therapy, a taxane, or a combination thereof.

In certain embodiments, the methods further comprise determining the presence or absence of a K-Ras mutation or a N-Ras mutation, wherein said sample does not have K-Ras mutation or N-Ras mutation. In certain embodiments, said sample has wild type K-Ras and wild type N-Ras. In specific embodiments, the sample is a tissue biopsy. In specific embodiments, the sample is a tumor biopsy. In specific embodiments, wherein determining the presence or absence of a Ras mutation comprising analyzing nucleic acids obtained from said sample.

In certain embodiments, Ras mutation is determined by sequencing, Polymerase Chain Reaction (PCR), DNA microarray, Mass Spectrometry (MS), Single Nucleotide Polymorphism (SNP) assay, denaturing high-performance liquid chromatography (DHPLC), or Restriction Fragment Length Polymorphism (RFLP) assay. In specific embodiments, Ras mutation is determined by PCR. In specific embodiments, Ras mutation is determined by sequencing. In specific embodiments, determining the presence or absence of a Ras mutation comprising analyzing proteins obtained from said sample.

In certain embodiments, said lung SCC is HPV negative. In certain embodiments, said lung SCC is HPV positive. In certain embodiments, said lung SCC is at an advanced stage or metastatic. In certain embodiments, said lung SCC is relapsed lung SCC.

In certain embodiments, the EGFR inhibitor is cetuximab. In certain embodiments, the EGFR inhibitor is erlotinib. In certain embodiments, the EGFR inhibitor is gefitinib. In certain embodiments, the EGFR inhibitor is panitumumab. In certain embodiments, the farnesyltransferase inhibitor (FTI) is tipifarnib.

In some embodiments, provided herein is a method of treating a lung SCC in a subject based on the presence of an HRAS mutation. In some embodiments, the lung SCC can be HPV negative lung SCC. In some embodiments, the lung SCC can be HPV positive lung SCC. In some embodiments, the lung SCC can be relapsed/recurrent lung SCC. In some embodiments, the lung SCC can be metastatic lung SCC. The methods provided herein include (a) determining the presence or absence of a HRAS mutation in a sample from the subject having lung SCC, and subsequently (b) administering a therapeutically effective amount of tipifarnib to the subject if the sample is determined to have a HRAS mutation. In certain embodiments, said tipifarnib is administered in combination with chemotherapy. In certain embodiments, said chemotherapy comprises a platinum-based therapy, a taxane, or a combination thereof.

In some embodiments, the FTI is selected from the group consisting of tipifarnib, lonafarnib (SCH-66336), CP-609, 754, BMS-214662, L778123, L744823, L739749, R208176, AZD3409 and FTI-277. In some embodiments, the FTI is administered at a dose of 1-1000 mg/kg body weight. In one embodiment, the FTI is tipifarnib. In some embodiments, tipifarnib is administered at a dose of 200-1200 mg twice a day ("b.i.d."). In some embodiments, tipifarnib is administered at a dose of 600 mg daily orally. In some embodiments, tipifarnib is administered at a dose of 300 mg b.i.d. orally for 3 of out of 4 weeks in repeated 4 week cycles. In some embodiments, tipifarnib is administered at a dose of 600 mg b.i.d. orally for 3 of out of 4 weeks in repeated 4 week cycles. In some embodiments, tipifarnib is administered at a dose of 900 mg b.i.d. orally in alternate weeks (one week on, one week off) in repeated 4 week cycles (days 1-7 and 15-21 of repeated 28-day cycles). In some embodiments, tipifarnib is administered at a dose of 1200 mg b.i.d. orally in alternate weeks (days 1-7 and 15-21 of repeated 28-day cycles). In some embodiments, tipifarnib is administered at a dose of 600 mg b.i.d. orally in alternate weeks (days 1-7 and 15-21 of repeated 28-day cycles). In some embodiments, tipifarnib is administered at a dose of 400 mg b.i.d. orally in alternate weeks (days 1-7 and 15-21 of repeated 28-day cycles). In some embodiments, tipifarnib is administered at a dose of 300 mg b.i.d. orally in alternate weeks (days 1-7 and 15-21 of repeated 28-day cycles). In some embodiments, tipifarnib is administered at a dose of 200 mg b.i.d. orally in alternate weeks (days 1-7 and 15-21 of repeated 28-day cycles). In some embodiments, tipifarnib is administered at a dose of 1200 mg b.i.d. orally for days 1-5 and 15-19 out of repeated 28-day cycles. In some embodiments, patients receive at least three cycles of treatment. In some embodiments, patients receive at least six cycles of treatment.

BRIEF DESCRIPTION OF THE DRAWINGS

FIG. 1A-B. CT scan of tumor of subject 1 at (A) baseline and (B) cycle 4, day 22. Tumor indicated in circle.

DETAILED DESCRIPTION

1. Definitions

Figure 2:
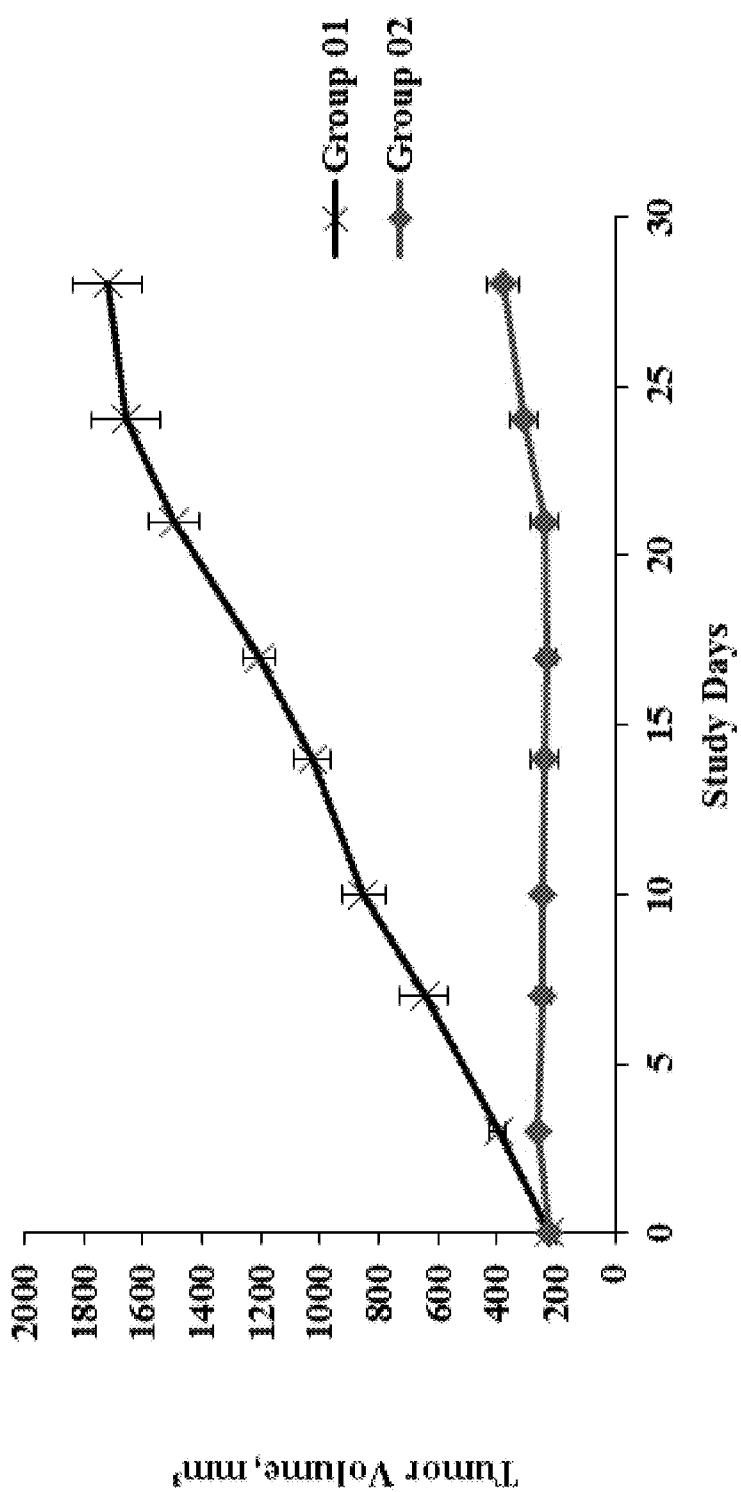
FIG. 2. Tumor volumes of mice in different groups during tipifarnib treatment in HUPRIME® head and neck cancer xenograft model HN1420, wherein group 01 is the vehicle group and group 02 is the tipifarnib group.

As used herein, the articles "a," "an," and "the" refer to one or to more than one of the grammatical object of the article. By way of example, a biomarker refers to one biomarker or more than one biomarkers.

As used herein, the term "subject" refers to a mammal. A subject can be a human or a non-human mammal such as a dog, cat, bovid, equine, mouse, rat, rabbit, or transgenic species thereof. The subject can be a patient, or a cancer patient.

As used herein, the term "cancer" or "cancerous" refers to the physiological condition in mammals that is typically characterized by unregulated cell growth. Examples of cancer include, but are not limited to, hematological cancers (e.g., multiple myeloma, lymphoma and leukemia), and solid tumors. As used herein, the term "premalignant condition" refers to a condition associated with an increased risk of cancer, which, if left untreated, can lead to cancer. A premalignant condition can also refer to non-invasive cancer that have not progressed into aggressive, invasive stage.

As used herein, the term "treat," "treating," and "treatment," when used in reference to a cancer patient, refer to an action that reduces the severity of the cancer, or retards or slows the progression of the cancer, including (a) inhibiting the cancer growth, or arresting development of the cancer, and (b) causing regression of the cancer, or delaying or minimizing one or more symptoms associated with the presence of the cancer.

As used herein, the term "determining" refers to using any form of measurement to assess the presence of a substance, either quantitatively or qualitatively. Measurement can be relative or absolute. Measuring the presence of a substance can include determining whether the substance is present or absent, or the amount of the substance.

As used herein, the term "administer," "administering," or "administration" refers to the act of delivering, or causing to be delivered, a compound or a pharmaceutical composition to the body of a subject by a method described herein or otherwise known in the art. Administering a compound or a pharmaceutical composition includes prescribing a compound or a pharmaceutical composition to be delivered into the body of a patient. Exemplary forms of administration include oral dosage forms, such as tablets, capsules, syrups, suspensions; injectable dosage forms, such as intravenous (IV), intramuscular (IM), or intraperitoneal (IP); transdermal dosage forms, including creams, jellies, powders, or patches; buccal dosage forms; inhalation powders, sprays, suspensions, and rectal suppositories.

As used herein, the term "therapeutically effective amount" of a compound when used in connection with a disease or disorder refers to an amount sufficient to provide a therapeutic benefit in the treatment or management of the disease or disorder or to delay or minimize one or more symptoms associated with the disease or disorder. A therapeutically effective amount of a compound means an amount of the compound, alone or in combination with other therapies, that provides a therapeutic benefit in the treatment or management of the disease or disorder. The term encompasses an amount that improves overall therapy, reduces or avoids symptoms, or enhances the therapeutic efficacy of another therapeutic agent. The term also refers to the amount of a compound that sufficiently elicits the biological or medical response of a biological molecule (e.g., a protein, enzyme, RNA, or DNA), cell, tissue, system, animal, or human, which is being sought by a researcher, veterinarian, medical doctor, or clinician.

As used herein, the term "sample" refers to a material or mixture of materials containing one or more components of interest. A sample from a subject refers to a sample obtained from the subject, including samples of biological tissue or fluid origin, obtained, reached, or collected in vivo or in situ. A sample can be obtained from a region of a subject containing precancerous or cancer cells or tissues. Such samples can be, but are not limited to, organs, tissues, fractions and cells isolated from a mammal. Exemplary samples include bone marrow, whole blood, partially purified blood, peripheral blood mononuclear cells ("PBMC"), and tissue biopsies. Exemplary samples also include cell lysate, a cell culture, a cell line, a tissue, oral tissue, gastrointestinal tissue, an organ, an organelle, a biological fluid, a blood sample, a urine sample, a skin sample, and the like.

As used herein, the term "biomarker" refers to a gene that can be either present or absent in individual subjects, or can be present but differentially expressed in individual subjects. The presence a biomarker, including the expression level of the biomarker, in a sample from a subject can indicate the responsiveness of the subject to a particular treatment, such as an FTI treatment.

As used herein, the term "express" or "expression" when used in connection with a gene refers to the process by which the information carried by the gene becomes manifest as the phenotype, including transcription of the gene to a messenger RNA (mRNA), the subsequent translation of the mRNA molecule to a polypeptide chain and its assembly into the ultimate protein.

As used herein, the term "RNA product of the biomarker" refers to a RNA transcript transcribed from a biomarker, and the term "protein product of the biomarker" refers to a protein or polypeptide translated from a RNA product of a biomarker.

As used herein, the term "expression level" of a biomarker refers to the amount or accumulation of the expression product of a biomarker, such as, for example, the amount of a RNA product of the biomarker (the RNA level of the biomarker) or the amount of a protein product of the biomarker (the protein level of the biomarker). If the biomarker is a gene with more than one alleles, the expression level of a biomarker refers to the total amount of accumulation of the expression product of all existing alleles for this gene, unless otherwise specified.

As used herein, the term "reference expression level" refers to a predetermined expression level of a biomarker that one can use to determine the significance of the expression level of the biomarker in a sample from a subject. A reference expression level of a biomarker can be the expression level of the biomarker in a sample from a healthy individual. A reference expression level of a biomarker can also be a cut-off value determined by a person of ordinary skill in the art through statistic analysis of the expression levels of the biomarker in a sample population and the responsiveness to a treatment of the individuals in the sample population.

As used herein, the term "responsiveness" or "responsive" when used in connection with a treatment refers to the effectiveness of the treatment in lessening or decreasing the symptoms of the disease being treated. For example, a cancer patient is responsive to an FTI treatment if the FTI treatment effectively inhibits the cancer growth, or arrests development of the cancer, causes regression of the cancer, or delays or minimizes one or more symptoms associated with the presence of the cancer in this patient.

The responsiveness to a particular treatment of a cancer patient can be characterized as a complete or partial response. "Complete response," or "CR" refers to an absence of clinically detectable disease with normalization of previously abnormal radiographic studies, bone marrow, and cerebrospinal fluid (CSF) or abnormal monoclonal protein measurements. "Partial response," or "PR," refers to at least about a 10%, 20%, 30%, 40%, 50%, 60%, 70%, 80%, or 90% decrease in all measurable tumor burden (i.e., the number of malignant cells present in the subject, or the measured bulk of tumor masses or the quantity of abnormal monoclonal protein) in the absence of new lesions.

A person of ordinary skill in the art would understand that clinical standards used to define CR, PR, or other level of patient responsiveness to treatments can vary for different types of cancer. For example, for hematopoietic cancers, patient being "responsive" to a particular treatment can be defined as patients who have a complete response (CR), a partial response (PR), or hematological improvement (HI) (Lancet et al., Blood 2:2 (2006)). For solid tumors, a patient being "responsive" to a particular treatment can be defined by RECIST criteria (see Therasse et al., "New guidelines to evaluate the response to treatment in solid tumors," JNCI 92(3):205-216 (2000)). HI can be defined as any bone marrow blast count less than 5% or a reduction in bone marrow blasts by at least half. On the other hand, patient being "not responsive" to a particular treatment can be defined as patients who have either progressive disease (PD) or stable disease (SD). Progressive disease (PD) can be defined as either >50% increase in bone marrow or circulating blast % from baseline, or new appearance of circulating blasts (on at least 2 consecutive occasions). Stable disease (SD) can be defined as any response not meeting CR, PR, HI, or PD criteria.

As used herein, the term "likelihood" refers to the probability of an event. A subject is "likely" to be responsive to a particular treatment when a condition is met means that the probability of the subject to be responsive to a particular treatment is higher when the condition is met than when the condition is not met. The probability to be responsive to a particular treatment can be higher by, for example, 5%, 10%, 25%, 50%, 100%, 200%, or more in a subject who meets a particular condition compared to a subject who does not meet the condition. For example, a cancer patient is "likely" to be responsive to an FTI treatment when the subject is a carrier of an HRAS mutation means that the probability of a subject to be responsive to FTI treatment is 5%, 10%, 25%, 50%, 100%, 200%, or more higher in a subject who is a carrier of an HRAS mutation compared to a subject who is not a carrier of an HRAS mutation.

Ras proteins are GTPases that regulate proliferation and by transducing biological information from extracellular signals to the nucleus. Mammalian cells express three ras genes that encode four Ras proteins, which are HRAS, N-Ras, $K_A$-Ras and $K_B$-Ras. $K_A$-Ras and $K_B$-Ras are also generally referred to as K-Ras. Ras proteins exist in either an active, GTP-bound or an inactive, GDP-bound, state. Mutant RAS proteins accumulate in the GTP-bound conformation due to defective intrinsic GTPase activity and/or resistance to inactivation by GTPase activating proteins (GAPs). Constitutive RAS signaling is mediated by mutations that prevent GTP hydrolysis, locking RAS in a permanently active state. In addition, RAS GTPases require lipid post-translational modification in the form of farnesylation or geranylgeranylation for their malignant transforming activity. Of the three RAS species (HRAS, KRAS, NRAS), HRAS is unique in the fact that it can be farnesylated but not geranylgeranylated. Consequently, farnesyl transferase inhibitors (FTIs) have been shown to inhibit the farnesylation of HRAS, prevent its association with the plasma membrane, inhibit downstream signal transduction pathways and inhibit tumor growth (Reviewed by Berndt et al. Nature Reviews Cancer 11:775-91). The Q22K HRAS mutation has been observed in Costello syndrome (Sheffield et al. Ped Dev Pathology 18, 237-244, 2015), a developmental and tumor predisposition disorder caused by germline HRAS mutation, and while its ability to drive neoplastic transformation has not been established, this mutation is in a highly conserved region across RAS proteins and Q22K KRAS has been established as a driver mutation (Tsukuda et al. Biochem Biophys Res Commun 2000; 278:653-58).

An exemplary amino acid sequence and a corresponding encoding nucleic acid sequence of human HRAS (GENBANK: CR536579.1 GI:49168641) are provided below:

```
                                              (SEQ ID NO: 1)
MTEYKLVVVG AGGVGKSALT IQLIQNHFVD EYDPTIEDSY

RKQVVIDGET CLLDILDTAG QEEYSAMRDQ YMRTGEGFLC

VFAINNTKSF EDIHQYREQI KRVKDSDDVP MVLVGNKCDL

AARTVESRQA QDLARSYGIP YIETSAKTRQ GVEDAFYTLV

REIRQHKLRK LNPPDESGPG CMSCKCVLS (SEQ ID NO: 2)
ATGACGGAAT ATAAGCTGGT GGTGGTGGGC GCCGGCGGTG

TGGGCAAGAG TGCGCTGACC ATCCAGCTGA TCCAGAACCA

CTTTGTGGAC GAATACGACC CCACTATAGA GGATTCCTAC

CGGAAGCAGG TGGTCATTGA TGGGGAGACG TGCCTGTTGG

ACATCCTGGA TACCGCCGGC CAGGAGGAGT ACAGCGCCAT

GCGGGACCAG TACATGCGCA CCGGGGAGGG CTTCCTGTGT

GTGTTTGCCA TCAACAACAC CAAGTCTTTT GAGGACATCC

ACCAGTACAG GGAGCAGATC AAACGGGTGA AGGACTCGGA

TGACGTGCCC ATGGTGCTGG TGGGGAACAA GTGTGACCTG

GCTGCACGCA CTGTGGAATC TCGGCAGGCT CAGGACCTCG

CCCGAAGCTA CGGCATCCCC TACATCGAGA CCTCGGCCAA

GACCCGGCAG GGAGTGGAGG ATGCCTTCTA CACGTTGGTG

CGTGAGATCC GGCAGCACAA GCTGCGGAAG CTGAACCCTC

CTGATGAGAG TGGCCCCGGC TGCATGAGCT GCAAGTGTGT

GCTCTCCTGA.
```

Ras isoforms are farnesylated. Farnesyltransferase (FTase) have crucial roles in the post-translational modifications of Ras proteins. A way of interfering with Ras function is the inhibition of FTase, the enzyme coupling a 15-carbon isoprenyl group to Ras proteins, by Farnesyltransferase Inhibitors ("FTI"). FTIs are a class of biologically active anticancer drugs that inhibit farnesylation of a wide range of target proteins, including Ras. The FTIs block Ras activation through inhibition of FTase, ultimately resulting in cell growth arrest. Thus, it was predicted that FTIs would be effective therapeutic agents in the treatment of cancer.

Thirty percent of all human cancers express oncogenically activated Ras. The high prevalence of mutated Ras, found in 30% of all human cancers, makes this pathway an attractive target for anticancer drug development. Initially, it was predicted that the Ras mutation(s) that led to constitutively active RAS pathway can serve as a biomarker for patient response to FTIs, which was based on the preclinical evidence that FTIs could block RAS-transformed cells. (Raponi et al., Blood 111:2589-96 (2008)).

As used herein, the term "HRAS mutation" refers to an activation mutation in an HRAS gene or HRAS protein. An HRAS mutation can refer to either a genetic alternation in the DNA sequence of the HRAS gene that results in activation of the corresponding HRAS protein, or the alteration in the amino acid sequence of an HRAS protein that results in its activation. Thus, the term "HRAS mutation" as used herein does not include an alternation in a HRAS gene that does not result in the activation of the HRAS protein, or an alternation of a HRAS protein sequence that does not lead to its activation. Accordingly, a sample or a subject that does not have any "HRAS mutation" as used herein can still have a mutation in the HRAS gene that does not affect the activity of the HRAS protein or a mutation that impairs the activity of the HRAS protein, or have a mutation in an HRAS protein that does not affect its activity or a mutation that impairs its activity. A sample or a subject can have multiple copies of the HRAS gene. A sample or a subject can also have both wild type and mutant HRAS proteins. As used herein, a sample or a subject having an HRAS mutation can also have a copy of wild type HRAS gene and/or the wild type HRAS protein. A sample or a subject that is determined to "have wild type HRAS," as used herein, refers to the sample or subject that only has the wild type HRAS gene and the wild type HRAS protein, and no HRAS mutation.

In some embodiments, the HRAS mutation can include at least one mutation at a codon selected from the group consisting of G12, G13, Q61, Q22, K117, and A146.

2. Farnesyltransferase Inhibitors for Cancer Treatment 2.1. Farnesyltransferase Inhibitors Provided herein are methods to treat squamous cell carcinoma of the head and neck with an FTI in a selected cancer patient or a selected population of cancer patients. The representative FTIs roughly belong to two classes (Shen et al., Drug Disc. Today 20:2 (2015)). The FTIs in the first class have the basic framework of farnesyldiphosphate (FPP). For instance, FPP analogs with a malonic acid group (Ta) were reported to be FTIs that compete with FPP (Duez, S. et al. Bioorg. Med. Chem. 18:543-556(2010)). In addition, imidazole-containing derivatives linked by an acidic substituent and a peptidyl chain were also synthesized as bisubstrate FTIs, and the designed bisubstrate inhibitors have better affinities than FPP. The FTIs in the second class are peptidomimetic molecules, which can be divided into two groups, namely thiol and non-thiol FTIs. Regarding the thiol FTIs, for instance L-739749, a selective peptidomimetic FTI shows potent antitumor activity in nude mice without system toxicity (Kohl, N. E. et al. PNAS 91:9141-9145(1994)). Additionally, a variety of thiol inhibitors were also developed, such as tripeptidyl FTIs (Lee, H-Y. et al. Bioorg. Med. Chem. Lett. 12:1599-1602(2002)).

For non-thiol FTIs, the heterocycles were therefore widely used to substitute the thiol group to contact with the zinc ion in the binding site. According to the structures of pharmacophoric groups, the nonthiol FTIs can be divided into three classes. The first class is featured by different monocyclic rings, such as L-778123, an FTI in Phase I clinical trials for solid tumors and lymphoma. L-778123 binds into the CAAX peptide site and competes with the CAAX substrate of farnesyltransferase. The second class is represented by tipifarnib in Phase III trials and BMS-214662 in Phase III trials, which are composed of diverse monocyclic rings and bicyclic rings (Harousseau et al. Blood 114: 1166-1173 (2009)). The representative inhibitor of the third class is lonafarnib, which is active in Ras-dependent and -independent malignant tumors, and has entered Phase III clinical trials for combating carcinoma, leukemia, and myelodysplastic syndrome. Lonafarnib is an FTI with a tricycle core, which contains a central seven-membered ring fused with two six-membered aromatic rings.

Thus, FTIs as described herein can take on a multitude of forms but share the essential inhibitory function of interfering with or lessening the farnesylation of proteins implicated in cancer and proliferative diseases.

Numerous FTIs are within the scope of this disclosure and include those described in U.S. Pat. Nos. 5,976,851; 5,972, 984; 5,972,966; 5,968,965; 5,968,952; 6,187,786; 6,169, 096; 6,037,350; 6,177,432; 5,965,578; 5,965,539; 5,958, 939; 5,939,557; 5,936,097; 5,891,889; 5,889,053; 5,880, 140; 5,872,135; 5,869,682; 5,861,529; 5,859,015; 5,856, 439; 5,856,326; 5,852,010; 5,843,941; 5,807,852; 5,780, 492; 5,773,455; 5,767,274; 5,756,528; 5,750,567; 5,721, 236; 5,700,806; 5,661,161; 5,602,098; 5,585,359; 5,578, 629; 5,534,537; 5,532,359; 5,523,430; 5,504,212; 5,491, 164; 5,420,245; and 5,238,922, the disclosures of which are hereby incorporated by reference in their entireties.

FTIs within the scope of this disclosure also include those described in Thomas et al., Biologics 1: 415-424 (2007); Shen et al., Drug Disc. Today 20:2 (2015); Appels et al., The Oncologist 10:565-578(2005), the disclosures of which are hereby incorporated by reference in their entireties.

In some embodiments, the FTIs include Arglabin (i.e. 1(R)-10-epoxy-5(S),7(S)-guaia-3(4),11(13)-dien-6,12-olide described in WO-98/28303 (NuOncology Labs); perrilyl alcohol described in WO-99/45912 (Wisconsin Genetics); SCH-66336 (lonafarnib), i.e. (+)-(R)-4-[2-[4-(3,10-dibromo-8-chloro-5,6-dihydro-11H-benzo [5,6]cyclohepta[1, 2-b]pyridin-11-yl)piperidin-1-yl]-2-oxoethyl]piperidine-1-carboxamide, described in U.S. Pat. No. 5,874,442 (Schering); L778123, i.e. 1-(3-chlorophenyl)-4-[1-(4-cyanobenzyl)-5-imidazolylmethyl]-2-piperazinone, described in WO-00/01691 (Merck); L739749, i.e. compound 2(S)-[2 (S)-[2(R)-amino-3-mercapto]propylamino-3(S)-methyl]-pentyloxy-3-phenylpropionyl-methionine sulfone described in WO-94/10138 (Merck); FTI-277, i.e., methyl {N-[2-phenyl-4-N [2(R)-amino-3-mecaptopropylamino]benzoyl] }-methionate (Calbiochem); L744832, i.e, 2S)-2-[[(2S)-2-[(2S,3S)-2-[(2R)-2-amino-3-mercaptopropyl]amino]-3-methylpentyl]oxy]-1-oxo-3-phenylpropyl]amino]-4-(methyl sulfonyl)-butanoic acid 1-methylethyl ester (Biomol International L.P.); CP-609,754 (Pfizer), i.e., (R)-6-[(4-chlorophenyl)-hydroxyl-(1-methyl-1-H-imidazol-5-yl)-methyl]-4-(3-ethynylphenyl)-1-methyl-2-(1H)-quinonlinone and (R)-6-[(4-chlorophenyl)-hydroxyl-(3-methyl-3-H-imidazol-4-yl)-methyl]-4-(3-ethynylphenyl)-1-methyl-2-(1H)-quinolinone; R208176 (Johnson & Johnson), i.e., JNJ-17305457, or (R)-1-(4-chlorophenyl)-1-[5-(3-chlorophenyl)tetrazolo[1,5-a]quinazolin-7-yl]-1-(1-methyl-1H-imidazol-5-yl)methanamine; AZD3409 (AstraZeneca), i.e. (S)-isopropyl 2-(2-(4-fluorophenethyl)-5-((((2S,4S)-4-(nicotinoylthio) pyrrolidin-2-yl)methyl)amino)benzamido)-4-(methylthio) butanoate; BMS 214662 (Bristol-Myers Squibb), i.e. (R)-2, 3,4,5-tetrahydro-1-(1H-imidazol-4-ylmethyl)-3-(phenylmethyl)-4-(2-thienylsulphonyl)-1H-1,4-benzodiazapine-7-carbonitrile, described in WO 97/30992 (Bristol Myers Squibb) and Pfizer compounds (A) and (B) described in WO-00/12498 and WO-00/12499.

In some embodiments, the FTI are the non-peptidal, so-called "small molecule" therapeutics, such as are quinolines or quinoline derivatives including:

7-(3-chlorophenyl)-9-[(4-chlorophenyl)-1H-imidazol-1-yl-methyl]-2,3-dihydro-o-1H,5H-benzo[ij]quinolizin-5-one,
7-(3-chlorophenyl)-9-[(4-chlorophenyl)-1H-imidazol-1-yl-methyl]-1,2-dihydro-o-4H-pyrrolo[3,2,1-ij]quinoline-4-one,
8-[amino(4-chlorophenyl)(1-methyl-1H-imidazol-5-yl), methyl]-6-(3-chloroph-enyl)-1,2-dihydro-4H-pyrrolo[3,2,1-ij]quinolin-4-one, and
8-[amino(4-chlorophenyl)(1-methyl-1H-imidazol-5-yl) methyl]-6-(3-chlorophe-nyl)-2,3-dihydro-1H, 5H-benzo[ij]quinolizin-5-one.

Tipifarnib is a nonpeptidomimetic FTI (Thomas et al., Biologics 1: 415-424 (2007)). It is a 4,6-disubstituted-1-methylquinolin-2-one derivative ((B)-6-[amino(4-chlorophenyl)(1-methyl-1H-imidazol-5-yl)methyl]-4-(3-chlorophenyl)-1-methyl-2(1H)-quinolinone)) that was obtained by optimization of a quinolone lead identified from compound library screening. Tipifarnib competitively inhibits the CAAX peptide binding site of FTase and is an extremely potent and highly selective inhibitor of farnesylation. Tipifarnib has manageable safety profile as single agent therapy and is reasonably well tolerated in man.

Tipifarnib is synthesized by the condensation of the anion of 1-methylimidazole with a 6-(4-chlorobenzoyl) quinolone derivative, followed by dehydration. The quinolone intermediate was prepared in four steps by cyclization of N-phenyl-3-(3-chlorophenyl)-2-propenamide, acylation, oxidation and N-methylation. Tipifarnib is a potent inhibitor of FTase in vitro and is orally active in a variety of animal models.

In some embodiments, provided herein is a method of treating cancer in a subject with an FTI or a pharmaceutical composition having FTI, or selecting a cancer patient for an FTI treatment. The pharmaceutical compositions provided herein contain therapeutically effective amounts of an FTI and a pharmaceutically acceptable carrier, diluent or excipient. In some embodiments, the FTI is tipifarnib; arglabin; perrilyl alcohol; lonafarnib (SCH-66336); L778123; L739749; FTI-277; L744832; R208176; BMS 214662; AZD3409; or CP-609,754. In some embodiments, the FTI is tipifarnib.

2.2. Formulations

The FTI can be formulated into suitable pharmaceutical preparations such as solutions, suspensions, tablets, dispersible tablets, pills, capsules, powders, sustained release formulations or elixirs, for oral administration or in sterile solutions or suspensions for ophthalmic or parenteral administration, as well as transdermal patch preparation and dry powder inhalers. Typically the FTI is formulated into pharmaceutical compositions using techniques and procedures well known in the art (see, e.g., Ansel Introduction to Pharmaceutical Dosage Forms, Seventh Edition 1999).

In the compositions, effective concentrations of the FTI and pharmaceutically acceptable salts is (are) mixed with a suitable pharmaceutical carrier or vehicle. In certain embodiments, the concentrations of the FTI in the compositions are effective for delivery of an amount, upon administration, that treats, prevents, or ameliorates one or more of the symptoms and/or progression of cancer, including haematological cancers and solid tumors.

The compositions can be formulated for single dosage administration. To formulate a composition, the weight fraction of the FTI is dissolved, suspended, dispersed or otherwise mixed in a selected vehicle at an effective concentration such that the treated condition is relieved or ameliorated. Pharmaceutical carriers or vehicles suitable for administration of the FTI provided herein include any such carriers known to those skilled in the art to be suitable for the particular mode of administration.

In addition, the FTI can be formulated as the sole pharmaceutically active ingredient in the composition or may be combined with other active ingredients. Liposomal suspensions, including tissue-targeted liposomes, such as tumor-targeted liposomes, may also be suitable as pharmaceutically acceptable carriers. These may be prepared according to methods known to those skilled in the art. For example, liposome formulations may be prepared as known in the art. Briefly, liposomes such as multilamellar vesicles (MLV's) may be formed by drying down egg phosphatidyl choline and brain phosphatidyl serine (7:3 molar ratio) on the inside of a flask. A solution of an FTI provided herein in phosphate buffered saline lacking divalent cations (PBS) is added and the flask shaken until the lipid film is dispersed. The resulting vesicles are washed to remove unencapsulated compound, pelleted by centrifugation, and then resuspended in PBS.

The FTI is included in the pharmaceutically acceptable carrier in an amount sufficient to exert a therapeutically useful effect in the absence of undesirable side effects on the patient treated. The therapeutically effective concentration may be determined empirically by testing the compounds in in vitro and in vivo systems described herein and then extrapolated therefrom for dosages for humans.

The concentration of FTI in the pharmaceutical composition will depend on absorption, tissue distribution, inactivation and excretion rates of the FTI, the physicochemical characteristics of the FTI, the dosage schedule, and amount administered as well as other factors known to those of skill in the art. For example, the amount that is delivered is sufficient to ameliorate one or more of the symptoms of cancer, including hematopoietic cancers and solid tumors.

In certain embodiments, a therapeutically effective dosage should produce a serum concentration of active ingredient from about 0.1 ng/ml to about 50-100 µg/ml. In one embodiment, the pharmaceutical compositions provide a dosage of from about 0.001 mg to about 2000 mg of compound per kilogram of body weight per day. Pharmaceutical dosage unit forms are prepared to provide from about 1 mg to about 1000 mg and in certain embodiments, from about 10 to about 500 mg of the essential active ingredient or a combination of essential ingredients per dosage unit form.

The FTI may be administered at once, or may be divided into a number of smaller doses to be administered at intervals of time. It is understood that the precise dosage and duration of treatment is a function of the disease being treated and may be determined empirically using known testing protocols or by extrapolation from in vivo or in vitro test data. It is to be noted that concentrations and dosage values may also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed compositions.

Thus, effective concentrations or amounts of one or more of the compounds described herein or pharmaceutically acceptable salts thereof are mixed with a suitable pharmaceutical carrier or vehicle for systemic, topical or local administration to form pharmaceutical compositions. Compounds are included in an amount effective for ameliorating one or more symptoms of, or for treating, retarding progression, or preventing. The concentration of active compound in the composition will depend on absorption, tissue distribution, inactivation, excretion rates of the active compound, the dosage schedule, amount administered, particular formulation as well as other factors known to those of skill in the art.

The compositions are intended to be administered by a suitable route, including but not limited to orally, parenterally, rectally, topically and locally. For oral administration, capsules, tablets, suspensions, and solutions can be formulated. The compositions are in liquid, semi-liquid or solid form and are formulated in a manner suitable for each route of administration.

Solutions or suspensions used for parenteral, intradermal, subcutaneous, or topical application can include any of the following components: a sterile diluent, such as water for injection, saline solution, fixed oil, polyethylene glycol, glycerine, propylene glycol, dimethyl acetamide or other synthetic solvent; antimicrobial agents, such as benzyl alcohol and methyl parabens; antioxidants, such as ascorbic acid and sodium bisulfite; chelating agents, such as ethylenediaminetetraacetic acid (EDTA); buffers, such as acetates, citrates and phosphates; and agents for the adjustment of tonicity such as sodium chloride or dextrose. Parenteral preparations can be enclosed in ampules, pens, disposable syringes or single or multiple dose vials made of glass, plastic or other suitable material.

In instances in which the FTI exhibits insufficient solubility, methods for solubilizing compounds can be used. Such methods are known to those of skill in this art, and include, but are not limited to, using cosolvents, such as dimethylsulfoxide (DMSO), using surfactants, such as TWEEN®, or dissolution in aqueous sodium bicarbonate.

Upon mixing or addition of the compound(s), the resulting mixture may be a solution, suspension, emulsion or the like. The form of the resulting mixture depends upon a number of factors, including the intended mode of administration and the solubility of the compound in the selected carrier or vehicle. The effective concentration is sufficient for ameliorating the symptoms of the disease, disorder or condition treated and may be empirically determined.

The pharmaceutical compositions are provided for administration to humans and animals in unit dosage forms, such as tablets, capsules, pills, powders, granules, sterile parenteral solutions or suspensions, and oral solutions or suspensions, and oil water emulsions containing suitable quantities of the compounds or pharmaceutically acceptable salts thereof. The pharmaceutically therapeutically active compounds and salts thereof are formulated and administered in unit dosage forms or multiple dosage forms. Unit dose forms as used herein refer to physically discrete units suitable for human and animal subjects and packaged individually as is known in the art. Each unit dose contains a predetermined quantity of the therapeutically active compound sufficient to produce the desired therapeutic effect, in association with the required pharmaceutical carrier, vehicle or diluent. Examples of unit dose forms include ampules and syringes and individually packaged tablets or capsules. Unit dose forms may be administered in fractions or multiples thereof. A multiple dose form is a plurality of identical unit dosage forms packaged in a single container to be administered in segregated unit dose form. Examples of multiple dose forms include vials, bottles of tablets or capsules or bottles of pints or gallons. Hence, multiple dose form is a multiple of unit doses which are not segregated in packaging.

Sustained-release preparations can also be prepared. Suitable examples of sustained-release preparations include semipermeable matrices of solid hydrophobic polymers containing the compound provided herein, which matrices are in the form of shaped articles, e.g., films, or microcapsule. Examples of sustained-release matrices include iontophoresis patches, polyesters, hydrogels (for example, poly(2-hydroxyethyl-methacrylate), or poly(vinylalcohol)), polylactides, copolymers of L-glutamic acid and ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods. When encapsulated compound remain in the body for a long time, they may denature or aggregate as a result of exposure to moisture at 37° C., resulting in a loss of biological activity and possible changes in their structure. Rational strategies can be devised for stabilization depending on the mechanism of action involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

Dosage forms or compositions containing active ingredient in the range of 0.005% to 100% with the balance made up from non toxic carrier may be prepared. For oral administration, a pharmaceutically acceptable non toxic composition is formed by the incorporation of any of the normally employed excipients, such as, for example pharmaceutical grades of mannitol, lactose, starch, magnesium stearate, talcum, cellulose derivatives, sodium crosscarmellose, glucose, sucrose, magnesium carbonate or sodium saccharin. Such compositions include solutions, suspensions, tablets, capsules, powders and sustained release formulations, such as, but not limited to, implants and microencapsulated delivery systems, and biodegradable, biocompatible polymers, such as collagen, ethylene vinyl acetate, polyanhydrides, polyglycolic acid, polyorthoesters, polylactic acid and others. Methods for preparation of these compositions are known to those skilled in the art. The contemplated compositions may contain about 0.001% 100% active ingredient, in certain embodiments, about 0.1-85% or about 75-95%.

The FTI or pharmaceutically acceptable salts can be prepared with carriers that protect the compound against rapid elimination from the body, such as time release formulations or coatings.

The compositions can include other active compounds to obtain desired combinations of properties. The compounds provided herein, or pharmaceutically acceptable salts thereof as described herein, can also be administered together with another pharmacological agent known in the general art to be of value in treating one or more of the diseases or medical conditions referred to hereinabove, such as diseases related to oxidative stress.

Lactose-free compositions provided herein can contain excipients that are well known in the art and are listed, for example, in the U.S. Pharmocopia (USP) SP (XXI)/NF (XVI). In general, lactose-free compositions contain an active ingredient, a binder/filler, and a lubricant in pharmaceutically compatible and pharmaceutically acceptable amounts. Exemplary lactose-free dosage forms contain an active ingredient, microcrystalline cellulose, pre-gelatinized starch and magnesium stearate.

Further encompassed are anhydrous pharmaceutical compositions and dosage forms containing a compound provided herein. For example, the addition of water (e.g., 5%) is widely accepted in the pharmaceutical arts as a means of simulating long-term storage in order to determine characteristics such as shelf-life or the stability of formulations over time. See, e.g., Jens T. Carstensen, Drug Stability: Principles & Practice, 2d. Ed., Marcel Dekker, NY, N.Y., 1995, pp. 379-80. In effect, water and heat accelerate the decomposition of some compounds. Thus, the effect of water on a formulation can be of great significance since moisture and/or humidity are commonly encountered during manufacture, handling, packaging, storage, shipment and use of formulations.

Anhydrous pharmaceutical compositions and dosage forms provided herein can be prepared using anhydrous or low moisture containing ingredients and low moisture or low humidity conditions. Pharmaceutical compositions and dosage forms that comprise lactose and at least one active ingredient that comprises a primary or secondary amine are anhydrous if substantial contact with moisture and/or humidity during manufacturing, packaging, and/or storage is expected.

An anhydrous pharmaceutical composition should be prepared and stored such that its anhydrous nature is maintained. Accordingly, anhydrous compositions are packaged using materials known to prevent exposure to water such that they can be included in suitable formulary kits. Examples of suitable packaging include, but are not limited to, hermetically sealed foils, plastics, unit dose containers (e.g., vials), blister packs and strip packs.

Oral pharmaceutical dosage forms are either solid, gel or liquid. The solid dosage forms are tablets, capsules, granules, and bulk powders. Types of oral tablets include compressed, chewable lozenges and tablets which may be enteric coated, sugar coated or film coated. Capsules may be hard or soft gelatin capsules, while granules and powders may be provided in non effervescent or effervescent form with the combination of other ingredients known to those skilled in the art.

In certain embodiments, the formulations are solid dosage forms, such as capsules or tablets. The tablets, pills, capsules, troches and the like can contain any of the following ingredients, or compounds of a similar nature: a binder; a diluent; a disintegrating agent; a lubricant; a glidant; a sweetening agent; and a flavoring agent.

Examples of binders include microcrystalline cellulose, gum tragacanth, glucose solution, acacia mucilage, gelatin solution, sucrose and starch paste. Lubricants include talc, starch, magnesium or calcium stearate, lycopodium and stearic acid. Diluents include, for example, lactose, sucrose, starch, kaolin, salt, mannitol and dicalcium phosphate. Glidants include, but are not limited to, colloidal silicon dioxide. Disintegrating agents include crosscarmellose sodium, sodium starch glycolate, alginic acid, corn starch, potato starch, bentonite, methylcellulose, agar and carboxymethylcellulose. Coloring agents include, for example, any of the approved certified water soluble FD and C dyes, mixtures thereof; and water insoluble FD and C dyes suspended on alumina hydrate. Sweetening agents include sucrose, lactose, mannitol and artificial sweetening agents such as saccharin, and any number of spray dried flavors. Flavoring agents include natural flavors extracted from plants such as fruits and synthetic blends of compounds which produce a pleasant sensation, such as, but not limited to peppermint and methyl salicylate. Wetting agents include propylene glycol monostearate, sorbitan monooleate, diethylene glycol monolaurate and polyoxyethylene laural ether. Emetic coatings include fatty acids, fats, waxes, shellac, ammoniated shellac and cellulose acetate phthalates. Film coatings include hydroxyethylcellulose, sodium carboxymethylcellulose, polyethylene glycol 4000 and cellulose acetate phthalate.

When the dosage unit form is a capsule, it can contain, in addition to material of the above type, a liquid carrier such as a fatty oil. In addition, dosage unit forms can contain various other materials which modify the physical form of the dosage unit, for example, coatings of sugar and other enteric agents. The compounds can also be administered as a component of an elixir, suspension, syrup, wafer, sprinkle, chewing gum or the like. A syrup may contain, in addition to the active compounds, sucrose as a sweetening agent and certain preservatives, dyes and colorings and flavors.

Pharmaceutically acceptable carriers included in tablets are binders, lubricants, diluents, disintegrating agents, coloring agents, flavoring agents, and wetting agents. Enteric coated tablets, because of the enteric coating, resist the action of stomach acid and dissolve or disintegrate in the neutral or alkaline intestines. Sugar coated tablets are compressed tablets to which different layers of pharmaceutically acceptable substances are applied. Film coated tablets are compressed tablets which have been coated with a polymer or other suitable coating. Multiple compressed tablets are compressed tablets made by more than one compression cycle utilizing the pharmaceutically acceptable substances previously mentioned. Coloring agents may also be used in the above dosage forms. Flavoring and sweetening agents are used in compressed tablets, sugar coated, multiple compressed and chewable tablets. Flavoring and sweetening agents are especially useful in the formation of chewable tablets and lozenges.

Liquid oral dosage forms include aqueous solutions, emulsions, suspensions, solutions and/or suspensions reconstituted from non effervescent granules and effervescent preparations reconstituted from effervescent granules. Aqueous solutions include, for example, elixirs and syrups. Emulsions are either oil in-water or water in oil.

Elixirs are clear, sweetened, hydroalcoholic preparations. Pharmaceutically acceptable carriers used in elixirs include solvents. Syrups are concentrated aqueous solutions of a sugar, for example, sucrose, and may contain a preservative. An emulsion is a two phase system in which one liquid is dispersed in the form of small globules throughout another liquid. Pharmaceutically acceptable carriers used in emulsions are non aqueous liquids, emulsifying agents and preservatives. Suspensions use pharmaceutically acceptable suspending agents and preservatives. Pharmaceutically acceptable substances used in non effervescent granules, to be reconstituted into a liquid oral dosage form, include diluents, sweeteners and wetting agents. Pharmaceutically acceptable substances used in effervescent granules, to be reconstituted into a liquid oral dosage form, include organic acids and a source of carbon dioxide. Coloring and flavoring agents are used in all of the above dosage forms.

Solvents include glycerin, sorbitol, ethyl alcohol and syrup. Examples of preservatives include glycerin, methyl and propylparaben, benzoic add, sodium benzoate and alcohol. Examples of non aqueous liquids utilized in emulsions include mineral oil and cottonseed oil. Examples of emulsifying agents include gelatin, acacia, tragacanth, bentonite, and surfactants such as polyoxyethylene sorbitan monooleate. Suspending agents include sodium carboxymethylcellulose, pectin, tragacanth, Veegum and acacia. Diluents include lactose and sucrose. Sweetening agents include sucrose, syrups, glycerin and artificial sweetening agents such as saccharin. Wetting agents include propylene glycol monostearate, sorbitan monooleate, diethylene glycol monolaurate and polyoxyethylene lauryl ether. Organic adds include citric and tartaric acid. Sources of carbon dioxide include sodium bicarbonate and sodium carbonate. Coloring agents include any of the approved certified water soluble FD and C dyes, and mixtures thereof. Flavoring agents include natural flavors extracted from plants such fruits, and synthetic blends of compounds which produce a pleasant taste sensation.

For a solid dosage form, the solution or suspension, in for example propylene carbonate, vegetable oils or triglycerides, is encapsulated in a gelatin capsule. Such solutions, and the preparation and encapsulation thereof, are disclosed in U.S. Pat. Nos. 4,328,245; 4,409,239; and 4,410,545. For a liquid dosage form, the solution, e.g., for example, in a polyethylene glycol, may be diluted with a sufficient quantity of a pharmaceutically acceptable liquid carrier, e.g., water, to be easily measured for administration.

Alternatively, liquid or semi solid oral formulations may be prepared by dissolving or dispersing the active compound or salt in vegetable oils, glycols, triglycerides, propylene glycol esters (e.g., propylene carbonate) and other such carriers, and encapsulating these solutions or suspensions in hard or soft gelatin capsule shells. Other useful formulations include, but are not limited to, those containing a compound provided herein, a dialkylated mono- or poly-alkylene glycol, including, but not limited to, 1,2-dimethoxymethane, diglyme, triglyme, tetraglyme, polyethylene glycol-350-dimethyl ether, polyethylene glycol-550-dimethyl ether, polyethylene glycol-750-dimethyl ether wherein 350, 550 and 750 refer to the approximate average molecular weight of the polyethylene glycol, and one or more antioxidants, such as butylated hydroxytoluene (BHT), butylated hydroxyanisole (BHA), propyl gallate, vitamin E, hydroquinone, hydroxycoumarins, ethanolamine, lecithin, cephalin, ascorbic acid, malic acid, sorbitol, phosphoric acid, thiodipropionic acid and its esters, and dithiocarbamates.

Other formulations include, but are not limited to, aqueous alcoholic solutions including a pharmaceutically acceptable acetal. Alcohols used in these formulations are any pharmaceutically acceptable water-miscible solvents having one or more hydroxyl groups, including, but not limited to, propylene glycol and ethanol. Acetals include, but are not limited to, di(lower alkyl) acetals of lower alkyl aldehydes such as acetaldehyde diethyl acetal.

In all embodiments, tablets and capsules formulations may be coated as known by those of skill in the art in order to modify or sustain dissolution of the active ingredient. Thus, for example, they may be coated with a conventional enterically digestible coating, such as phenylsalicylate, waxes and cellulose acetate phthalate.

Parenteral administration, generally characterized by injection, either subcutaneously, intramuscularly or intravenously is also provided herein. Injectables can be prepared in conventional forms, either as liquid solutions or suspensions, solid forms suitable for solution or suspension in liquid prior to injection, or as emulsions. Suitable excipients are, for example, water, saline, dextrose, glycerol or ethanol. In addition, if desired, the pharmaceutical compositions to be administered may also contain minor amounts of non toxic auxiliary substances such as wetting or emulsifying agents, pH buffering agents, stabilizers, solubility enhancers, and other such agents, such as for example, sodium acetate, sorbitan monolaurate, triethanolamine oleate and cyclodextrins. Implantation of a slow release or sustained release system, such that a constant level of dosage is maintained is also contemplated herein. Briefly, a compound provided herein is dispersed in a solid inner matrix, e.g., polymethylmethacrylate, polybutylmethacrylate, plasticized or unplasticized polyvinylchloride, plasticized nylon, plasticized polyethyleneterephthalate, natural rubber, polyisoprene, polyisobutylene, polybutadiene, polyethylene, ethylene-vinylacetate copolymers, silicone rubbers, polydimethylsiloxanes, silicone carbonate copolymers, hydrophilic polymers such as hydrogels of esters of acrylic and methacrylic acid, collagen, cross-linked polyvinylalcohol and cross-linked partially hydrolyzed polyvinyl acetate, that is surrounded by an outer polymeric membrane, e.g., polyethylene, polypropylene, ethylene/propylene copolymers, ethylene/ethyl acrylate copolymers, ethylene/vinylacetate copolymers, silicone rubbers, polydimethyl siloxanes, neoprene rubber, chlorinated polyethylene, polyvinylchloride, vinylchloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer, that is insoluble in body fluids. The compound diffuses through the outer polymeric membrane in a release rate controlling step. The percentage of active compound contained in such parenteral compositions is highly dependent on the specific nature thereof, as well as the activity of the compound and the needs of the subject.

Parenteral administration of the compositions includes intravenous, subcutaneous and intramuscular administrations. Preparations for parenteral administration include sterile solutions ready for injection, sterile dry soluble products, such as lyophilized powders, ready to be combined with a solvent just prior to use, including hypodermic tablets, sterile suspensions ready for injection, sterile dry insoluble products ready to be combined with a vehicle just prior to use and sterile emulsions. The solutions may be either aqueous or nonaqueous.

If administered intravenously, suitable carriers include physiological saline or phosphate buffered saline (PBS), and solutions containing thickening and solubilizing agents, such as glucose, polyethylene glycol, and polypropylene glycol and mixtures thereof.

Pharmaceutically acceptable carriers used in parenteral preparations include aqueous vehicles, nonaqueous vehicles, antimicrobial agents, isotonic agents, buffers, antioxidants, local anesthetics, suspending and dispersing agents, emulsifying agents, sequestering or chelating agents and other pharmaceutically acceptable substances.

Examples of aqueous vehicles include Sodium Chloride Injection, Ringers Injection, Isotonic Dextrose Injection, Sterile Water Injection, Dextrose and Lactated Ringers Injection. Nonaqueous parenteral vehicles include fixed oils of vegetable origin, cottonseed oil, corn oil, sesame oil and peanut oil. Antimicrobial agents in bacteriostatic or fungistatic concentrations must be added to parenteral preparations packaged in multiple dose containers which include phenols or cresols, mercurials, benzyl alcohol, chlorobutanol, methyl and propyl p hydroxybenzoic acid esters, thimerosal, benzalkonium chloride and benzethonium chloride. Isotonic agents include sodium chloride and dextrose. Buffers include phosphate and citrate. Antioxidants include sodium bisulfate. Local anesthetics include procaine hydrochloride. Suspending and dispersing agents include sodium carboxymethylceluose, hydroxypropyl methylcellulose and polyvinylpyrrolidone. Emulsifying agents include Polysorbate 80 (TWEEN® 80). A sequestering or chelating agent of metal ions include EDTA. Pharmaceutical carriers also include ethyl alcohol, polyethylene glycol and propylene glycol for water miscible vehicles and sodium hydroxide, hydrochloric acid, citric acid or lactic acid for pH adjustment.

The concentration of the FTI is adjusted so that an injection provides an effective amount to produce the desired pharmacological effect. The exact dose depends on the age, weight and condition of the patient or animal as is known in the art. The unit dose parenteral preparations are packaged in an ampule, a vial or a syringe with a needle. All preparations for parenteral administration must be sterile, as is known and practiced in the art.

Illustratively, intravenous or intraarterial infusion of a sterile aqueous solution containing an FTI is an effective mode of administration. Another embodiment is a sterile aqueous or oily solution or suspension containing an active material injected as necessary to produce the desired pharmacological effect.

Injectables are designed for local and systemic administration. Typically a therapeutically effective dosage is formulated to contain a concentration of at least about 0.1% w/w up to about 90% w/w or more, such as more than 1% w/w of the active compound to the treated tissue(s). The active ingredient may be administered at once, or may be divided into a number of smaller doses to be administered at intervals of time. It is understood that the precise dosage and duration of treatment is a function of the tissue being treated and may be determined empirically using known testing protocols or by extrapolation from in vivo or in vitro test data. It is to be noted that concentrations and dosage values may also vary with the age of the individual treated. It is to be further understood that for any particular subject, specific dosage regimens should be adjusted over time according to the individual need and the professional judgment of the person administering or supervising the administration of the formulations, and that the concentration ranges set forth herein are exemplary only and are not intended to limit the scope or practice of the claimed formulations.

The FTI can be suspended in micronized or other suitable form or may be derivatized to produce a more soluble active product or to produce a prodrug. The form of the resulting mixture depends upon a number of factors, including the intended mode of administration and the solubility of the compound in the selected carrier or vehicle. The effective concentration is sufficient for ameliorating the symptoms of the condition and may be empirically determined.

Of interest herein are also lyophilized powders, which can be reconstituted for administration as solutions, emulsions and other mixtures. They can also be reconstituted and formulated as solids or gels.

The sterile, lyophilized powder is prepared by dissolving an FTI provided herein, or a pharmaceutically acceptable salt thereof, in a suitable solvent. The solvent may contain an excipient which improves the stability or other pharmacological component of the powder or reconstituted solution, prepared from the powder. Excipients that may be used include, but are not limited to, dextrose, sorbital, fructose, corn syrup, xylitol, glycerin, glucose, sucrose or other suitable agent. The solvent may also contain a buffer, such as citrate, sodium or potassium phosphate or other such buffer known to those of skill in the art at, in one embodiment, about neutral pH. Subsequent sterile filtration of the solution followed by lyophilization under standard conditions known to those of skill in the art provides the desired formulation. Generally, the resulting solution will be apportioned into vials for lyophilization. Each vial will contain a single dosage (including but not limited to 10-1000 mg or 100-500 mg) or multiple dosages of the compound. The lyophilized powder can be stored under appropriate conditions, such as at about 4° C. to room temperature.

Reconstitution of this lyophilized powder with water for injection provides a formulation for use in parenteral administration. For reconstitution, about 1-50 mg, about 5-35 mg, or about 9-30 mg of lyophilized powder, is added per mL of sterile water or other suitable carrier. The precise amount depends upon the selected compound. Such amount can be empirically determined.

Topical mixtures are prepared as described for the local and systemic administration. The resulting mixture may be a solution, suspension, emulsion or the like and are formulated as creams, gels, ointments, emulsions, solutions, elixirs, lotions, suspensions, tinctures, pastes, foams, aerosols, irrigations, sprays, suppositories, bandages, dermal patches or any other formulations suitable for topical administration.

The FTI or pharmaceutical composition having an FTI can be formulated as aerosols for topical application, such as by inhalation (see, e.g., U.S. Pat. Nos. 4,044,126, 4,414,209, and 4,364,923, which describe aerosols for delivery of a steroid useful for treatment of inflammatory diseases, particularly asthma). These formulations for administration to the respiratory tract can be in the form of an aerosol or solution for a nebulizer, or as a microfine powder for insufflation, alone or in combination with an inert carrier such as lactose. In such a case, the particles of the formulation will have diameters of less than 50 microns or less than 10 microns.

The FTI or pharmaceutical composition having an FTI can be formulated for local or topical application, such as for topical application to the skin and mucous membranes, such as in the eye, in the form of gels, creams, and lotions and for application to the eye or for intracisternal or intraspinal application. Topical administration is contemplated for transdermal delivery and also for administration to the eyes or mucosa, or for inhalation therapies. Nasal solutions of the active compound alone or in combination with other pharmaceutically acceptable excipients can also be administered. These solutions, particularly those intended for ophthalmic use, may be formulated as 0.01%-10% isotonic solutions, pH about 5-7, with appropriate salts.

Other routes of administration, such as transdermal patches, and rectal administration are also contemplated herein. For example, pharmaceutical dosage forms for rectal administration are rectal suppositories, capsules and tablets for systemic effect. Rectal suppositories are used herein mean solid bodies for insertion into the rectum which melt or soften at body temperature releasing one or more pharmacologically or therapeutically active ingredients. Pharmaceutically acceptable substances utilized in rectal suppositories are bases or vehicles and agents to raise the melting point. Examples of bases include cocoa butter (theobroma oil), glycerin gelatin, carbowax (polyoxyethylene glycol) and appropriate mixtures of mono, di and triglycerides of fatty acids. Combinations of the various bases may be used. Agents to raise the melting point of suppositories include spermaceti and wax. Rectal suppositories may be prepared either by the compressed method or by molding. An exemplary weight of a rectal suppository is about 2 to 3 grams. Tablets and capsules for rectal administration are manufactured using the same pharmaceutically acceptable substance and by the same methods as for formulations for oral administration.

The FTI or pharmaceutical composition having an FTI provided herein can be administered by controlled release means or by delivery devices that are well known to those of ordinary skill in the art. Examples include, but are not limited to, those described in U.S. Pat. Nos. 3,845,770; 3,916,899; 3,536,809; 3,598,123; and 4,008,719, 5,674,533, 5,059,595, 5,591,767, 5,120,548, 5,073,543, 5,639,476, 5,354,556, 5,639,480, 5,733,566, 5,739,108, 5,891,474, 5,922,356, 5,972,891, 5,980,945, 5,993,855, 6,045,830, 6,087,324, 6,113,943, 6,197,350, 6,248,363, 6,264,970, 6,267,981, 6,376,461, 6,419,961, 6,589,548, 6,613,358, 6,699,500 and 6,740,634, each of which is incorporated herein by reference. Such dosage forms can be used to provide slow or controlled-release of FTI using, for example, hydropropylmethyl cellulose, other polymer matrices, gels, permeable membranes, osmotic systems, multilayer coatings, microparticles, liposomes, microspheres, or a combination thereof to provide the desired release profile in varying proportions. Suitable controlled-release formulations known to those of ordinary skill in the art, including those described herein, can be readily selected for use with the active ingredients provided herein.

All controlled-release pharmaceutical products have a common goal of improving drug therapy over that achieved by their non-controlled counterparts. In one embodiment, the use of an optimally designed controlled-release preparation in medical treatment is characterized by a minimum of drug substance being employed to cure or control the condition in a minimum amount of time. In certain embodiments, advantages of controlled-release formulations include extended activity of the drug, reduced dosage frequency, and increased patient compliance. In addition, controlled-release formulations can be used to affect the time of onset of action or other characteristics, such as blood levels of the drug, and can thus affect the occurrence of side (e.g., adverse) effects.

Most controlled-release formulations are designed to initially release an amount of drug (active ingredient) that promptly produces the desired therapeutic effect, and gradually and continually release of other amounts of drug to maintain this level of therapeutic effect over an extended period of time. In order to maintain this constant level of drug in the body, the drug must be released from the dosage form at a rate that will replace the amount of drug being metabolized and excreted from the body. Controlled-release of an active ingredient can be stimulated by various conditions including, but not limited to, pH, temperature, enzymes, water, or other physiological conditions or compounds.

In certain embodiments, the FTI can be administered using intravenous infusion, an implantable osmotic pump, a transdermal patch, liposomes, or other modes of administration. In one embodiment, a pump may be used (see, Sefton, CRC Crit. Ref. Biomed. Eng. 14:201 (1987); Buchwald et al., Surgery 88:507 (1980); Saudek et al., N. Engl. J. Med. 321:574 (1989). In another embodiment, polymeric materials can be used. In yet another embodiment, a controlled release system can be placed in proximity of the therapeutic target, i.e., thus requiring only a fraction of the systemic dose (see, e.g., Goodson, Medical Applications of Controlled Release, vol. 2, pp. 115-138 (1984).

In some embodiments, a controlled release device is introduced into a subject in proximity of the site of inappropriate immune activation or a tumor. Other controlled release systems are discussed in the review by Langer (Science 249:1527-1533 (1990). The F can be dispersed in a solid inner matrix, e.g., polymethylmethacrylate, polybutylmethacrylate, plasticized or unplasticized polyvinylchloride, plasticized nylon, plasticized polyethyleneterephthalate, natural rubber, polyisoprene, polyisobutylene, polybutadiene, polyethylene, ethylene-vinylacetate copolymers, silicone rubbers, polydimethylsiloxanes, silicone carbonate copolymers, hydrophilic polymers such as hydrogels of esters of acrylic and methacrylic acid, collagen, cross-linked polyvinylalcohol and cross-linked partially hydrolyzed polyvinyl acetate, that is surrounded by an outer polymeric membrane, e.g., polyethylene, polypropylene, ethylene/propylene copolymers, ethylene/ethyl acrylate copolymers, ethylene/vinylacetate copolymers, silicone rubbers, polydimethyl siloxanes, neoprene rubber, chlorinated polyethylene, polyvinylchloride, vinylchloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer, that is insoluble in body fluids. The active ingredient then diffuses through the outer polymeric membrane in a release rate controlling step. The percentage of active ingredient contained in such parenteral compositions is highly dependent on the specific nature thereof, as well as the needs of the subject.

The FTI or pharmaceutical composition of FTI can be packaged as articles of manufacture containing packaging material, a compound or pharmaceutically acceptable salt thereof provided herein, which is used for treatment, prevention or amelioration of one or more symptoms or progression of cancer, including hematological cancers and solid tumors, and a label that indicates that the compound or pharmaceutically acceptable salt thereof is used for treatment, prevention or amelioration of one or more symptoms or progression of cancer, including hematological cancers and solid tumors.

The articles of manufacture provided herein contain packaging materials. Packaging materials for use in packaging pharmaceutical products are well known to those of skill in the art. See, e.g., U.S. Pat. Nos. 5,323,907, 5,052,558 and 5,033,252. Examples of pharmaceutical packaging materials include, but are not limited to, blister packs, bottles, tubes, inhalers, pumps, bags, vials, containers, syringes, pens, bottles, and any packaging material suitable for a selected formulation and intended mode of administration and treatment. A wide array of formulations of the compounds and compositions provided herein are contemplated.

2.3. Dosages

In some embodiments, a therapeutically effective amount of the pharmaceutical composition having an FTI is administered orally or parenterally. In some embodiments, the pharmaceutical composition having tipifarnib as the active ingredient and is administered orally in an amount of from 1 up to 1500 mg/kg daily, either as a single dose or subdivided into more than one dose, or more particularly in an amount of from 10 to 1200 mg/kg daily. In some embodiments, the pharmaceutical composition having tipifarnib as the active ingredient and is administered orally in an amount of 100 mg/kg daily, 200 mg/kg daily, 300 mg/kg daily, 400 mg/kg daily, 500 mg/kg daily, 600 mg/kg daily, 700 mg/kg daily, 800 mg/kg daily, 900 mg/kg daily, 1000 mg/kg daily, 1100 mg/kg daily, or 1200 mg/kg daily. In some embodiments, the FTI is tipifarnib.

In some embodiments, the FTI is administered at a dose of 200-1500 mg daily. In some embodiments, the FTI is administered at a dose of 200-1200 mg daily. In some embodiments, the FTI is administered at a dose of 200 mg daily. In some embodiments, the FTI is administered at a dose of 300 mg daily. In some embodiments, the FTI is administered at a dose of 400 mg daily. In some embodiments, the FTI is administered at a dose of 500 mg daily. In some embodiments, the FTI is administered at a dose of 600 mg daily. In some embodiments, the FTI is administered at a dose of 700 mg daily. In some embodiments, the FTI is administered at a dose of 800 mg daily. In some embodiments, the FTI is administered at a dose of 900 mg daily. In some embodiments, the FTI is administered at a dose of 1000 mg daily. In some embodiments, the FTI is administered at a dose of 1100 mg daily. In some embodiments, the FTI is administered at a dose of 1200 mg daily. In some embodiments, the FTI is administered at a dose of 1300 mg daily. In some embodiments, the FTI is administered at a dose of 1400 mg daily. In some embodiments, the FTI is tipifarnib.

In some embodiments, the FTI is administered at a dose of 200-1400 mg b.i.d. (i.e., twice a day). In some embodiments, the FTI is administered at a dose of 300-1200 mg b.i.d. In some embodiments, the FTI is administered at a dose of 300-900 mg b.i.d. In some embodiments, the FTI is administered at a dose of 600 mg b.i.d. In some embodiments, the FTI is administered at a dose of 700 mg b.i.d. In some embodiments, the FTI is administered at a dose of 800 mg b.i.d. In some embodiments, the FTI is administered at a dose of 900 mg b.i.d. In some embodiments, the FTI is administered at a dose of 1000 mg b.i.d. In some embodiments, the FTI is administered at a dose of 1100 mg b.i.d. In some embodiments, the FTI is administered at a dose of 1200 mg b.i.d. In some embodiments, the FTI is tipifarnib.

As a person of ordinary skill in the art would understand, the dosage varies depending on the dosage form employed, condition and sensitivity of the patient, the route of administration, and other factors. The exact dosage will be determined by the practitioner, in light of factors related to the subject that requires treatment. Dosage and administration are adjusted to provide sufficient levels of the active ingredient or to maintain the desired effect. Factors which can be taken into account include the severity of the disease state, general health of the subject, age, weight, and gender of the subject, diet, time and frequency of administration, drug combination(s), reaction sensitivities, and tolerance/response to therapy. During a treatment cycle, the daily dose could be varied. In some embodiments, a starting dosage can be titrated down within a treatment cycle. In some embodiments, a starting dosage can be titrated up within a treatment cycle. The final dosage can depend on the occurrence of dose limiting toxicity and other factors. In some embodiments, the FTI is administered at a starting dose of 300 mg daily and escalated to a maximum dose of 400 mg, 500 mg, 600 mg, 700 mg, 800 mg, 900 mg, 1000 mg, 1100 mg, or 1200 mg daily. In some embodiments, the FTI is administered at a starting dose of 400 mg daily and escalated to a maximum dose of 500 mg, 600 mg, 700 mg, 800 mg, 900 mg, 1000 mg, 1100 mg, or 1200 mg daily. In some embodiments, the FTI is administered at a starting dose of 500 mg daily and escalated to a maximum dose of 600 mg, 700 mg, 800 mg, 900 mg, 1000 mg, 1100 mg, or 1200 mg daily. In some embodiments, the FTI is administered at a starting dose of 600 mg daily and escalated to a maximum dose of 700 mg, 800 mg, 900 mg, 1000 mg, 1100 mg, or 1200 mg daily. In some embodiments, the FTI is administered at a starting dose of 700 mg daily and escalated to a maximum dose of 800 mg, 900 mg, 1000 mg, 1100 mg, or 1200 mg daily. In some embodiments, the FTI is administered at a starting dose of 800 mg daily and escalated to a maximum dose of 900 mg, 1000 mg, 1100 mg, or 1200 mg daily. In some embodiments, the FTI is administered at a starting dose of 900 mg daily and escalated to a maximum dose of 1000 mg, 1100 mg, or 1200 mg daily. The dose escalation can be done at once, or step wise. For example, a starting dose at 600 mg daily can be escalated to a final dose of 1000 mg daily by increasing by 100 mg per day over the course of 4 days, or by increasing by 200 mg per day over the course of 2 days, or by increasing by 400 mg at once. In some embodiments, the FTI is tipifarnib.

In some embodiments, the FTI is administered at a relatively high starting dose and titrated down to a lower dose depending on the patient response and other factors. In some embodiments, the FTI is administered at a starting dose of 1200 mg daily and reduced to a final dose of 1100 mg, 1000 mg, 900 mg, 800 mg, 700 mg, 600 mg, 500 mg, 400 mg, or 300 mg daily. In some embodiments, the FTI is administered at a starting dose of 1100 mg daily and reduced to a final dose of 1000 mg, 900 mg, 800 mg, 700 mg, 600 mg, 500 mg, 400 mg, or 300 mg daily. In some embodiments, the FTI is administered at a starting dose of 1000 mg daily and reduced to a final dose of 900 mg, 800 mg, 700 mg, 600 mg, 500 mg, 400 mg, or 300 mg daily. In some embodiments, the FTI is administered at a starting dose of 900 mg daily and reduced to a final dose of 800 mg, 700 mg, 600 mg, 500 mg, 400 mg, or 300 mg daily. In some embodiments, the FTI is administered at a starting dose of 800 mg daily and reduced to a final dose of 700 mg, 600 mg, 500 mg, 400 mg, or 300 mg daily. In some embodiments, the FTI is administered at a starting dose of 600 mg daily and reduced to a final dose of 500 mg, 400 mg, or 300 mg daily. The dose reduction can be done at once, or step wise. In some embodiments, the FTI is tipifarnib. For example, a starting dose at 900 mg daily can be reduced to a final dose of 600 mg daily by decreasing by 100 mg per day over the course of 3 days, or by decreasing by 300 mg at once.

A treatment cycle can have different length. In some embodiments, a treatment cycle can be one week, 2 weeks, 3 weeks, 4 weeks, 5 weeks, 6 weeks, 7 weeks, 8 weeks, 3 months, 4 months, 5 months, 6 months, 7 months, 8 months, 9 months, 10 months, 11 months, or 12 months. In some embodiments, a treatment cycle is 4 weeks. A treatment cycle can have intermittent schedule. In some embodiments, a 2-week treatment cycle can have 5-day dosing followed by 9-day rest. In some embodiments, a 2-week treatment cycle can have 6-day dosing followed by 8-day rest. In some embodiments, a 2-week treatment cycle can have 7-day dosing followed by 7-day rest. In some embodiments, a 2-week treatment cycle can have 8-day dosing followed by 6-day rest. In some embodiments, a 2-week treatment cycle can have 9-day dosing followed by 5-day rest.

In some embodiments, the FTI is administered daily for 3 of out of 4 weeks in repeated 4 week cycles. In some embodiments, the FTI is administered daily in alternate weeks (one week on, one week off) in repeated 4 week cycles. In some embodiments, the FTI is administered at a dose of 300 mg b.i.d. orally for 3 of out of 4 weeks in repeated 4 week cycles. In some embodiments, the FTI is administered at a dose of 600 mg b.i.d. orally for 3 of out of 4 weeks in repeated 4 week cycles. In some embodiments, the FTI is administered at a dose of 900 mg b.i.d. orally in alternate weeks (one week on, one week off) in repeated 4 week cycles. In some embodiments, the FTI is administered at a dose of 1200 mg b.i.d. orally in alternate weeks (days 1-7 and 15-21 of repeated 28-day cycles). In some embodiments, the FTI is administered at a dose of 1200 mg b.i.d. orally for days 1-5 and 15-19 out of repeated 28-day cycles.

In some embodiments, a 900 mg b.i.d. tipifarnib alternate week regimen can be used adopted. Under the regimen, patients receive a starting dose of 900 mg, po, b.i.d. on days 1-7 and 15-21 of 28-day treatment cycles. In some embodiments, patients receive two treatment cycles. In some embodiments, patients receive three treatment cycles. In some embodiments, patients receive four treatment cycles. In some embodiments, patients receive five treatment cycles. In some embodiments, patients receive six treatment cycles. In some embodiments, patients receive seven treatment cycles. In some embodiments, patients receive eight treatment cycles. In some embodiments, patients receive nine treatment cycles. In some embodiments, patients receive ten treatment cycles. In some embodiments, patients receive eleven treatment cycles. In some embodiments, patients receive twelve treatment cycles. In some embodiments, patients receive more than twelve treatment cycles.

In the absence of unmanageable toxicities, subjects can continue to receive the tipifarnib treatment for up to 12 months or longer. The dose can also be increased to 1200 mg b.i.d. if the subject is tolerating the treatment well. Stepwise 300 mg dose reductions to control treatment-related, treatment-emergent toxicities can also be included.

In some other embodiments, tipifarnib is given orally at a dose of 300 mg b.i.d. daily for 21 days, followed by 1 week of rest, in 28-day treatment cycles (21-day schedule; Cheng D T, et al., *J Mol Diagn.* (2015) 17(3):251-64). In some embodiments, a 5-day dosing ranging from 25 to 1300 mg b.i.d. followed by 9-day rest is adopted (5-day schedule; Zujewski J., *J Clin Oncol.*, (2000) February; 18(4):927-41). In some embodiments, a 7-day b.i.d. dosing followed by 7-day rest is adopted (7-day schedule; Lara P N Jr., *Anticancer Drugs.*, (2005) 16(3):317-21; Kirschbaum M H, *Leukemia.*, (2011) October; 25(10):1543-7; Kurzrock, *Clin Cancer Res* (2008), 14(2):509). In the 7-day schedule, the patients can receive a starting dose of 300 mg b.i.d. with 300 mg dose escalations to a maximum planned dose of 1800 mg b.i.d. In the 7-day schedule study, patients can also receive tipifarnib b.i.d. on days 1-7 and days 15-21 of 28-day cycles at doses up to 1600 mg b.i.d.

FTI can inhibit the growth of mammalian tumors when administered as a twice daily dosing schedule. Administration of an FTI in a single dose daily for one to five days can produce a marked suppression of tumor growth lasting out to at least 21 days. In some embodiments, FTI is administered at a dosage range of 50-400 mg/kg. In some embodiments, FTI is administered at 200 mg/kg. Dosing regimen for specific FTIs are also well known in the art (e.g., U.S. Pat. No. 6,838,467, which is incorporated herein by reference in its entirety). For example, suitable dosages for the compounds Arglabin (WO98/28303), perrilyl alcohol (WO 99/45712), SCH-66336 (U.S. Pat. No. 5,874,442), L778123 (WO 00/01691), 2(S)-[2(S)-[2(R)-amino-3-mercapto]propylamino-3 (S)-methyl]-pentyloxy-3-phenylpropionyl-methionine sulfone (WO94/10138), BMS 214662 (WO 97/30992), AZD3409; Pfizer compounds A and B (WO 00/12499 and WO 00/12498) are given in the aforementioned patent specifications which are incorporated herein by reference or are known to or can be readily determined by a person skilled in the art.

In relation to perrilyl alcohol, the medicament may be administered 1-4 g per day per 150 lb human patient. Preferably, 1-2 g per day per 150 lb human patient. SCH-66336 typically can be administered in a unit dose of about 0.1 mg to 100 mg, more preferably from about 1 mg to 300 mg according to the particular application. Compounds L778123 and 1-(3-chlorophenyl)-4-[1-(4-cyanobenzyl)-5-imidazolylmethyl]-2-piperazinone may be administered to a human patient in an amount between about 0.1 mg/kg of body weight to about 20 mg/kg of body weight per day, preferably between 0.5 mg/kg of bodyweight to about 10 mg/kg of body weight per day.

Pfizer compounds A and B may be administered in dosages ranging from about 1.0 mg up to about 500 mg per day, preferably from about 1 to about 100 mg per day in single or divided (i.e. multiple) doses. Therapeutic compounds will ordinarily be administered in daily dosages ranging from about 0.01 to about 10 mg per kg body weight per day, in single or divided doses. BMS 214662 may be administered in a dosage range of about 0.05 to 200 mg/kg/day, preferably less than 100 mg/kg/day in a single dose or in 2 to 4 divided doses.

2.4. Combination Therapies

In some embodiments, the FTI treatment is administered in combination with radiotherapy, or radiation therapy. Radiotherapy includes using γ-rays, X-rays, and/or the directed delivery of radioisotopes to tumor cells. Other forms of DNA damaging factors are also contemplated, such as microwaves, proton beam irradiation (U.S. Pat. Nos. 5,760,395 and 4,870,287; all of which are hereby incorporated by references in their entireties), and UV-irradiation. It is most likely that all of these factors affect a broad range of damage on DNA, on the precursors of DNA, on the replication and repair of DNA, and on the assembly and maintenance of chromosomes.

In some embodiments, a therapeutically effective amount of the pharmaceutical composition having an FTI is administered that effectively sensitizes a tumor in a host to irradiation. (U.S. Pat. No. 6,545,020, which is hereby incorporated by reference in its entirety). Irradiation can be ionizing radiation and in particular gamma radiation. In some embodiments, the gamma radiation is emitted by linear accelerators or by radionuclides. The irradiation of the tumor by radionuclides can be external or internal.

Irradiation can also be X-ray radiation. Dosage ranges for X-rays range from daily doses of 50 to 200 roentgens for prolonged periods of time (3 to 4 wk), to single doses of 2000 to 6000 roentgens. Dosage ranges for radioisotopes vary widely, and depend on the half-life of the isotope, the strength and type of radiation emitted, and the uptake by the neoplastic cells.

In some embodiments, the administration of the pharmaceutical composition commences up to one month, in particular up to 10 days or a week, before the irradiation of the tumor. Additionally, irradiation of the tumor is fractionated the administration of the pharmaceutical composition is maintained in the interval between the first and the last irradiation session.

The amount of FTI, the dose of irradiation and the intermittence of the irradiation doses will depend on a series of parameters such as the type of tumor, its location, the patients' reaction to chemo- or radiotherapy and ultimately is for the physician and radiologists to determine in each individual case.

In some embodiments, the methods provided herein further include administering a therapeutically effective amount of a second active agent or a support care therapy. The second active agent can be a chemotherapeutic agent. A chemotherapeutic agent or drug can be categorized by its mode of activity within a cell, for example, whether and at what stage they affect the cell cycle. Alternatively, an agent can be characterized based on its ability to directly cross-link DNA, to intercalate into DNA, or to induce chromosomal and mitotic aberrations by affecting nucleic acid synthesis.

Examples of chemotherapeutic agents include alkylating agents, such as thiotepa and cyclosphosphamide; alkyl sulfonates, such as busulfan, improsulfan, and piposulfan; aziridines, such as benzodopa, carboquone, meturedopa, and uredopa; ethylenimines and methylamelamines, including altretamine, triethylenemelamine, trietylenephosphoramide, triethiylenethiophosphoramide, and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB 1-TM1); eleutherobin; pancratistatin; a sarcodictyin; spongistatin; nitrogen mustards, such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, and uracil mustard; nitrosureas, such as carmustine, chlorozotocin, fotemustine, lomustine, nimustine, and ranimnustine; antibiotics, such as the enediyne antibiotics (e.g., calicheamicin, especially calicheamicin gammaII and calicheamicin omegaI1); dynemicin, including dynemicin A; bisphosphonates, such as clodronate; an esperamicin; as well as neocarzinostatin chromophore and related chromoprotein enediyne antiobiotic chromophores, aclacinomysins, actinomycin, authrarnycin, azaserine, bleomycins, cactinomycin, carabicin, carminomycin, carzinophilin, chromomycinis, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins, such as mitomycin C, mycophenolic acid, nogalarnycin, olivomycins, peplomycin, potfiromycin, puromycin, quelamycin, rodorubicin, streptonigrin, streptozocin, tubercidin, ubenimex, zinostatin, and zorubicin; anti-metabolites, such as methotrexate and 5-fluorouracil (5-FU); folic acid analogues, such as denopterin, pteropterin, and trimetrexate; purine analogs, such as fludarabine, 6-mercaptopurine, thiamiprine, and thioguanine; pyrimidine analogs, such as ancitabine, azacitidine, 6-azauridine, carmofur, cytarabine, dideoxyuridine, doxifluridine, enocitabine, and floxuridine; androgens, such as calusterone, dromostanolone propionate, epitiostanol, mepitiostane, and testolactone; anti-adrenals, such as mitotane and trilostane; folic acid replenisher, such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids, such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSKpolysaccharide complex; razoxane; rhizoxin; sizofiran; spirogermanium; tenuazonic acid; triaziquone; 2,2',2''-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; taxoids, e.g., paclitaxel and docetaxel gemcitabine; 6-thioguanine; mercaptopurine; platinum coordination complexes, such as cisplatin, oxaliplatin, and carboplatin; vinblastine; platinum; etoposide (VP-16); ifosfamide; mitoxantrone; vincristine; vinorelbine; novantrone; teniposide; edatrexate; daunomycin; aminopterin; xeloda; ibandronate; irinotecan (e.g., CPT-11); topoisomerase inhibitor RFS 2000; difluorometlhylornithine (DMFO); retinoids, such as retinoic acid; capecitabine; carboplatin, procarbazine, plicomycin, gemcitabine, navelbine, transplatinum, and pharmaceutically acceptable salts, acids, or derivatives of any of the above.

The second active agents can be large molecules (e.g., proteins) or small molecules (e.g., synthetic inorganic, organometallic, or organic molecules). In some embodiments, the second active agent is a DNA-hypomethylating agent, a therapeutic antibody that specifically binds to a cancer antigen, a hematopoietic growth factor, cytokine, anti-cancer agent, antibiotic, cox-2 inhibitor, immunomodulatory agent, anti-thymocyte globulin, immunosuppressive agent, corticosteroid or a pharmacologically active mutant or derivative thereof.

In some embodiments, the second active agent is a DNA hypomethylating agent, such as a cytidine analog (e.g., azacitidine) or a 5-azadeoxycytidine (e.g. decitabine). In some embodiments, the second active agent is a cytoreductive agent, including but not limited to Induction, Topotecan, Hydrea, PO Etoposide, Lenalidomide, LDAC, and Thioguanine. In some embodiments, the second active agent is Mitoxantrone, Etoposide, Cytarabine, or Valspodar. In some embodiment, the second active agent is Mitoxantrone plus Valspodar, Etoposide plus Valspodar, or Cytarabine plus Valspodar. In some embodiment, the second active agent is idarubicin, fludarabine, topotecan, or ara-C. In some other embodiments, the second active agent is idarubicin plus ara-C, fludarabine plus ara-C, mitoxantrone plus ara-C, or topotecan plus ara-C. In some embodiments, the second active agent is a quinine. Other combinations of the agents specified above can be used, and the dosages can be determined by the physician.

In some embodiments, the second active agent is an immunotherapy agent. In some embodiments, the second active agent is anti-PD1 antibody or anti-PDL1 antibody.

In some embodiments, it is contemplated that the second active agent or second therapy used in combination with an FTI can be administered before, at the same time, or after the FTI treatment. In some embodiments, the second active agent or second therapy used in combination with an FTI can be administered before the FTI treatment. In some embodiments, the second active agent or second therapy used in combination with an FTI can be administered at the same time as FTI treatment. In some embodiments, the second active agent or second therapy used in combination with an FTI can be administered after the FTI treatment.

The FTI treatment can also be administered in combination with a bone marrow transplant. In some embodiments, the FTI is administered before the bone marrow transplant. In other embodiments, the FTI is administered after the bone marrow transplant.

3. Biomarkers for FTI Treatment

Provided herein are methods of selection of squamous cell carcinoma of the head and neck (SCCHN) and lung squamous cell carcinoma (lung SCC) patients for treatment with a farnesyltransferase inhibitor (FTI). Farnesyltransferase (FTase) have crucial roles in the post-translational modifications of Ras proteins. FTIs are a class of biologically active anticancer drugs that inhibit farnesylation of a wide range of target proteins, including Ras. The Ras proteins play a pivotal role in the transduction of cell growth-stimulating signals, and mutation of the ras gene leads to constant activation of the protein, ultimately resulting in uncontrolled cell proliferation. The high prevalence of mutated ras genes, found in 30% of all human cancers, makes this pathway an attractive target for anticancer drug development. A way of interfering with Ras function is the inhibition of FTase, the enzyme coupling a 15-carbon isoprenyl group to Ras proteins, by FTIs. The FTIs block Ras activation through inhibition of FTase, ultimately resulting in cell growth arrest. Thus, it was predicted that FTIs would be effective therapeutic agents in the treatment of cancer.

However, no correlation between ras mutations and response to FTIs was demonstrated in past clinical studies (Karp et al. Blood 97:3361-3369 (2001); and US. Patent Pub. 20070048782)). While several early clinical studies focused on cancers that exhibited high frequencies of ras mutations, the response rate was disappointingly low in those trials. (Mesa Lancet Oncol 6:279-286 (2006); Rao et al. J Clin Oncol 22:3950-3957 (2004))

Early studies of tipifarnib, an FTI, were conducted in poor risk and previously untreated AML patients (CTEP-20 phase II), and AML patients with relapsed/refractory AML (INT-17 Phase II). A phase III study of tipifarnib versus best supportive care (BSC) failed to demonstrate improvement in overall survival. Multiple gene/proteins have been associated in the literature with the activity of FTI (AKAP13, mDIA, etc.) (Raponi et al. Clin Cancer Res. 13:2254-60 (2007); Kamasani et al. Cancer Biology & Therapy, 6:1418-1423 (2007)), and analyses of gene expression profiling in bone marrow samples from 2 AML studies (CTEP-20, INT-17) identified the ratio of the expression of 2 genes: RASGRP1 (T cell signal transducer) and APTX (DNA repair protein) as a potential biomarker of tipifarnib's activity in AML (Raponi et al. Blood. 111:2589-96(2008)). However, a subsequent prospective study using the 2-gene ratio in bone marrow blasts as inclusion criterion failed to demonstrate significant clinical benefit of tipifarnib in AML (Lancet et al. Blood (ASH) 120: Abstract 1508(2012)).

The present invention identifies HRAS mutations as biomarkers associated with better prognosis for an FTI treatment, and novel methods are provided herein for patient selection for an FTI treatment. The HRAS mutations identified in the instant application are specifically associated with the clinical benefit of an FTI treatment, but not with the clinical benefit of agents of other standard chemotherapies.

As disclosed herein, the methods can also be used in connection with other patient stratification approaches to further increase the response rate of a patient population to an FTI treatment. For example, in some embodiments, the methods provided herein further include determining the mutation status of the HRAS gene and selecting a patient for an FTI treatment, as described in greater detail below. In some embodiments, the methods provided herein further include determining the mutation status of the ras genes and selecting a patient for an FTI treatment when the patient has an HRAS mutation with wild type K-ras and wild type N-ras. In other embodiments, the methods provided herein can further include using the 2 gene ratio between RASGRP1 and APTX as additional patient selection criterion for an FTI treatment (U.S. Pat. No. 7,932,036, which is hereby incorporated by reference in its entirety). Methods described herein or otherwise known in the art can be used to determine the mutation status of the ras gene, such as the HRAS gene. In some embodiments, the mutation status of a ras gene, such as HRAS, can be determined by NGS.

In some embodiments, the methods provided herein include determining the expression level of a biomarker. In some embodiments, the expression level of a biomarker can be the protein level of the biomarker. In some embodiments, the expression level of a biomarker can be the RNA level of the biomarker. Any method as described herein or otherwise known in the art to determine the protein level or RNA level of a gene can be used for determining the expression level of a biomarker in present invention.

Exemplary methods of detecting or quantitating mRNA levels include but are not limited to PCR-based methods, northern blots, ribonuclease protection assays, and the like. The mRNA sequence (e.g., the mRNA of a biomarker, such as CRBN or a CAP, or a fragment thereof) can be used to prepare a probe that is at least partially complementary. The probe can then be used to detect the mRNA sequence in a sample, using any suitable assay, such as PCR-based methods, Northern blotting, a dipstick assay, and the like.

The commonly used methods known in the art for the quantification of mRNA expression in a sample include northern blotting and in situ hybridization (Parker &Barnes, Methods in Molecular Biology 106:247-283 (1999)); RNAse protection assays (Hod, Biotechniques 13:852-854 (1992)); and polymerase chain reaction (PCR) (Weis et ah, Trends in Genetics 8:263-264 (1992)). Alternatively, antibodies may be employed that can recognize specific duplexes, including DNA duplexes, RNA duplexes, and DNA-RNA hybrid duplexes or DNA-protein duplexes. Representative methods for sequencing-based gene expression analysis include Serial Analysis of Gene Expression (SAGE), and gene expression analysis by massively parallel signature sequencing (MPSS).

A sensitive and flexible quantitative method is PCR. Examples of PCR methods can be found in the literature. Examples of PCR assays can be found in U.S. Pat. No. 6,927,024, which is incorporated by reference herein in its entirety. Examples of RT-PCR methods can be found in U.S. Pat. No. 7,122,799, which is incorporated by reference herein in its entirety. A method of fluorescent in situ PCR is described in U.S. Pat. No. 7,186,507, which is incorporated by reference herein in its entirety.

It is noted, however, that other nucleic acid amplification protocols (i.e., other than PCR) may also be used in the nucleic acid analytical methods described herein. For example, suitable amplification methods include ligase chain reaction (see, e.g., Wu & Wallace, Genomics 4:560-569, 1988); strand displacement assay (see, e.g., Walker et al., Proc. Natl. Acad. Sci. USA 89:392-396, 1992; U.S. Pat. No. 5,455,166); and several transcription-based amplification systems, including the methods described in U.S. Pat.

Nos. 5,437,990; 5,409,818; and 5,399,491; the transcription amplification system (TAS) (Kwoh et al., Proc. Natl. Acad. Sci. USA 86: 1173-1177, 1989); and self-sustained sequence replication (3 SR) (Guatelli et al., Proc. Natl. Acad. Sci. USA 87: 1874-1878, 1990; WO 92/08800). Alternatively, methods that amplify the probe to detectable levels can be used, such as Q-replicase amplification (Kramer & Lizardi, Nature 339:401-402, 1989; Lomeli et al., Clin. Chem. 35: 1826-1831, 1989). A review of known amplification methods is provided, for example, by Abramson and Myers in Current Opinion in Biotechnology 4:41-47 (1993).

mRNA may be isolated from the starting tissue sample. General methods for mRNA extraction are well known in the art and are disclosed in standard textbooks of molecular biology, including Ausubel et al., Current Protocols of Molecular Biology, John Wiley and Sons (1997). In particular, RNA isolation can be performed using purification kit, buffer set and protease from commercial manufacturers, such as Qiagen, according to the manufacturer's instructions. For example, total RNA from cells in culture can be isolated using Qiagen RNeasy mini-columns. Other commercially available RNA isolation kits include MASTER-PURE® Complete DNA and RNA Purification Kit (EPI-CENTRE®, Madison, Wis.), and Paraffin Block RNA Isolation Kit (Ambion, Inc.). Total RNA from tissue samples can be isolated using RNA Stat-60 (Tel-Test). RNA prepared from tumor can be isolated, for example, by cesium chloride density gradient centrifugation.

In some embodiments, the first step in gene expression profiling by PCR is the reverse transcription of the RNA template into cDNA, followed by its exponential amplification in a PCR reaction. In other embodiments, a combined reverse-transcription-polymerase chain reaction (RT-PCR) reaction may be used, e.g., as described in U.S. Pat. Nos. 5,310,652; 5,322,770; 5,561,058; 5,641,864; and 5,693,517. The two commonly used reverse transcriptases are avilo myeloblastosis virus reverse transcriptase (AMV-RT) and Moloney murine leukemia virus reverse transcriptase (MMLV-RT). The reverse transcription step is typically primed using specific primers, random hexamers, or oligo-dT primers, depending on the circumstances and the goal of expression profiling. For example, extracted RNA can be reverse-transcribed using a GENEAMP™ RNA PCR kit (Perkin Elmer, Calif, USA), following the manufacturer's instructions. The derived cDNA can then be used as a template in the subsequent PCR reaction.

In some embodiments, Real-Time Reverse Transcription-PCR (qRT-PCR) can be used for both the detection and quantification of RNA targets (Bustin, et al., 2005, *Clin. Sci.*, 109:365-379). Examples of qRT-PCR-based methods can be found, for example, in U.S. Pat. No. 7,101,663, which is incorporated by reference herein in its entirety. Instruments for real-time PCR, such as the Applied Biosystems 7500, are available commercially, as are the reagents, such as TaqMan Sequence Detection chemistry.

For example, TaqMan® Gene Expression Assays can be used, following the manufacturer's instructions. These kits are pre-formulated gene expression assays for rapid, reliable detection and quantification of human, mouse and rat mRNA transcripts. TaqMan® or 5'-nuclease assay, as described in U.S. Pat. Nos. 5,210,015; 5,487,972; and 5,804,375; and Holland et al., 1988, Proc. Natl. Acad. Sci. USA 88:7276-7280, can be used. TAQMAN® PCR typically utilizes the 5'-nuclease activity of Taq or Tth polymerase to hydrolyze a hybridization probe bound to its target amplicon, but any enzyme with equivalent 5' nuclease activity can be used. Two oligonucleotide primers are used to generate an amplicon typical of a PCR reaction. A third oligonucleotide, or probe, is designed to detect nucleotide sequence located between the two PCR primers. The probe is non-extendible by Taq DNA polymerase enzyme, and is labeled with a reporter fluorescent dye and a quencher fluorescent dye. Any laser-induced emission from the reporter dye is quenched by the quenching dye when the two dyes are located close together as they are on the probe. During the amplification reaction, the Taq DNA polymerase enzyme cleaves the probe in a template-dependent manner. The resultant probe fragments disassociate in solution, and signal from the released reporter dye is free from the quenching effect of the second fluorophore. One molecule of reporter dye is liberated for each new molecule synthesized, and detection of the unquenched reporter dye provides the basis for quantitative interpretation of the data.

Any method suitable for detecting degradation product can be used in a 5' nuclease assay. Often, the detection probe is labeled with two fluorescent dyes, one of which is capable of quenching the fluorescence of the other dye. The dyes are attached to the probe, preferably one attached to the 5' terminus and the other is attached to an internal site, such that quenching occurs when the probe is in an unhybridized state and such that cleavage of the probe by the 5' to 3' exonuclease activity of the DNA polymerase occurs in between the two dyes.

Amplification results in cleavage of the probe between the dyes with a concomitant elimination of quenching and an increase in the fluorescence observable from the initially quenched dye. The accumulation of degradation product is monitored by measuring the increase in reaction fluorescence. U.S. Pat. Nos. 5,491,063 and 5,571,673, both incorporated herein by reference, describe alternative methods for detecting the degradation of probe which occurs concomitant with amplification. 5'-Nuclease assay data may be initially expressed as Ct, or the threshold cycle. As discussed above, fluorescence values are recorded during every cycle and represent the amount of product amplified to that point in the amplification reaction. The point when the fluorescent signal is first recorded as statistically significant is the threshold cycle (Ct).

To minimize errors and the effect of sample-to-sample variation, PCR is usually performed using an internal standard. The ideal internal standard is expressed at a constant level among different tissues, and is unaffected by the experimental treatment. RNAs most frequently used to normalize patterns of gene expression are mRNAs for the housekeeping genes glyceraldehyde-3-phosphate-dehydrogenase (GAPDH) and P-actin.

PCR primers and probes are designed based upon intron sequences present in the gene to be amplified. In this embodiment, the first step in the primer/probe design is the delineation of intron sequences within the genes. This can be done by publicly available software, such as the DNA BLAT software developed by Kent, W., Genome Res. 12(4):656-64 (2002), or by the BLAST software including its variations. Subsequent steps follow well established methods of PCR primer and probe design.

In order to avoid non-specific signals, it can be important to mask repetitive sequences within the introns when designing the primers and probes. This can be easily accomplished by using the Repeat Masker program available on-line through the Baylor College of Medicine, which screens DNA sequences against a library of repetitive elements and returns a query sequence in which the repetitive elements are masked. The masked intron sequences can then be used to design primer and probe sequences using any commercially or otherwise publicly available primer/probe design packages, such as Primer Express (Applied Biosystems); MGB assay-by-design (Applied Biosystems); Primer3 (Rozen and Skaletsky (2000) Primer3 on the WWW for general users and for biologist programmers. In: Krawetz S, Misener S (eds) Bioinformatics Methods and Protocols: Methods in Molecular Biology. Humana Press, Totowa, N.J., pp 365-386).

Factors considered in PCR primer design include primer length, melting temperature (Tm), and G/C content, specificity, complementary primer sequences, and 3'-end sequence. In general, optimal PCR primers are generally 17-30 bases in length, and contain about 20-80%, such as, for example, about 50-60% G+C bases. Tm's between 50 and 80° C., e.g. about 50 to 70° C. are typically preferred. For further guidelines for PCR primer and probe design see, e.g. Dieffenbach et ah, "General Concepts for PCR Primer Design" in: PCR Primer, A Laboratory Manual, Cold Spring Harbor Laboratory Press, New York, 1995, pp. 133-155; Innis and Gelfand, "Optimization of PCRs" in: PCR Protocols, A Guide to Methods and Applications, CRC Press, London, 1994, pp. 5-11; and Plasterer, T. N. Primerselect: Primer and probe design. Methods Mol. Biol. 70:520-527 (1997), the entire disclosures of which are hereby expressly incorporated by reference.

An exemplary PCR program, for example, is 50° C. for 2 minutes, 95° C. for 10 minutes, 40 cycles of 95° C. for 15 seconds, then 60° C. for 1 minute. To determine the cycle number at which the fluorescence signal associated with a particular amplicon accumulation crosses the threshold (referred to as the CT), the data can be analyzed, for example, using a 7500 Real-Time PCR System Sequence Detection software v1.3 using the comparative CT relative quantification calculation method. Using this method, the output is expressed as a fold-change of expression levels. In some embodiments, the threshold level can be selected to be automatically determined by the software. In some embodiments, the threshold level is set to be above the baseline but sufficiently low to be within the exponential growth region of an amplification curve.

RNA-Seq, also called Whole Transcriptome Shotgun Sequencing (WTSS) refers to the use of high-throughput sequencing technologies to sequence cDNA in order to get information about a sample's RNA content. Publications describing RNA-Seq include: Wang et al., Nature Reviews Genetics 10 (1): 57-63 (January 2009); Ryan et al. BioTechniques 45 (1): 81-94 (2008); and Maher et al., Nature 458 (7234): 97-101 (January 2009); which are hereby incorporated in their entirety.

Differential gene expression can also be identified, or confirmed using the microarray technique. In this method, polynucleotide sequences of interest (including cDNAs and oligonucleotides) are plated, or arrayed, on a microchip substrate. The arrayed sequences are then hybridized with specific DNA probes from cells or tissues of interest.

In an embodiment of the microarray technique, PCR amplified inserts of cDNA clones are applied to a substrate in a dense array. Preferably at least 10,000 nucleotide sequences are applied to the substrate. The microarrayed genes, immobilized on the microchip at 10,000 elements each, are suitable for hybridization under stringent conditions. Fluorescently labeled cDNA probes may be generated through incorporation of fluorescent nucleotides by reverse transcription of RNA extracted from tissues of interest. Labeled cDNA probes applied to the chip hybridize with specificity to each spot of DNA on the array. After stringent washing to remove non-specifically bound probes, the chip is scanned by confocal laser microscopy or by another detection method, such as a CCD camera. Quantitation of hybridization of each arrayed element allows for assessment of corresponding mRNA abundance. With dual color fluorescence, separately labeled cDNA probes generated from two sources of RNA are hybridized pairwise to the array. The relative abundance of the transcripts from the two sources corresponding to each specified gene is thus determined simultaneously. The miniaturized scale of the hybridization affords a convenient and rapid evaluation of the expression pattern for large numbers of genes. Such methods have been shown to have the sensitivity required to detect rare transcripts, which are expressed at a few copies per cell, and to reproducibly detect at least approximately two-fold differences in the expression levels (Schena et al., Proc. Natl. Acad. Sci. USA 93(2): 106-149 (1996)). Microarray analysis can be performed by commercially available equipment, following manufacturer's protocols, such as by using the Affymetrix GENCHIP™ technology, or Incyte's microarray technology.

Serial analysis of gene expression (SAGE) is a method that allows the simultaneous and quantitative analysis of a large number of gene transcripts, without the need of providing an individual hybridization probe for each transcript. First, a short sequence tag (about 10-14 bp) is generated that contains sufficient information to uniquely identify a transcript, provided that the tag is obtained from a unique position within each transcript. Then, many transcripts are linked together to form long serial molecules, that can be sequenced, revealing the identity of the multiple tags simultaneously. The expression pattern of any population of transcripts can be quantitatively evaluated by determining the abundance of individual tags, and identifying the gene corresponding to each tag. For more details see, e.g. Velculescu et ah, Science 270:484-487 (1995); and Velculescu et al, Cell 88:243-51 (1997).

The MassARRAY (Sequenom, San Diego, Calif.) technology is an automated, high-throughput method of gene expression analysis using mass spectrometry (MS) for detection. According to this method, following the isolation of RNA, reverse transcription and PCR amplification, the cDNAs are subjected to primer extension. The cDNA-derived primer extension products are purified, and dispensed on a chip array that is pre-loaded with the components needed for MALTI-TOF MS sample preparation. The various cDNAs present in the reaction are quantitated by analyzing the peak areas in the mass spectrum obtained.

mRNA level can also be measured by an assay based on hybridization. A typical mRNA assay method can contain the steps of 1) obtaining surface-bound subject probes; 2) hybridization of a population of mRNAs to the surface-bound probes under conditions sufficient to provide for specific binding (3) post-hybridization washes to remove nucleic acids not bound in the hybridization; and (4) detection of the hybridized mRNAs. The reagents used in each of these steps and their conditions for use may vary depending on the particular application.

Any suitable assay platform can be used to determine the mRNA level in a sample. For example, an assay can be in the form of a dipstick, a membrane, a chip, a disk, a test strip, a filter, a microsphere, a slide, a multiwell plate, or an optical fiber. An assay system can have a solid support on which a nucleic acid corresponding to the mRNA is attached. The solid support can have, for example, a plastic, silicon, a metal, a resin, glass, a membrane, a particle, a precipitate, a gel, a polymer, a sheet, a sphere, a polysaccharide, a capillary, a film a plate, or a slide. The assay components can be prepared and packaged together as a kit for detecting an mRNA.

The nucleic acid can be labeled, if desired, to make a population of labeled mRNAs. In general, a sample can be labeled using methods that are well known in the art (e.g., using DNA ligase, terminal transferase, or by labeling the RNA backbone, etc.; see, e.g., Ausubel, et al., *Short Protocols in Molecular Biology*, 3rd ed., Wiley & Sons 1995 and Sambrook et al., *Molecular Cloning: A Laboratory Manual*, Third Edition, 2001 Cold Spring Harbor, N.Y.). In some embodiments, the sample is labeled with fluorescent label. Exemplary fluorescent dyes include but are not limited to xanthene dyes, fluorescein dyes, rhodamine dyes, fluorescein isothiocyanate (FITC), 6 carboxyfluorescein (FAM), 6 carboxy-2',4',7',4,7-hexachlorofluorescein (HEX), 6 carboxy 4', 5' dichloro 2', 7' dimethoxyfluorescein (JOE or J), N,N,N',N' tetramethyl 6 carboxyrhodamine (TAMRA or T), 6 carboxy X rhodamine (ROX or R), 5 carboxyrhodamine 6G (R6G5 or G5), 6 carboxyrhodamine 6G (R6G6 or G6), and rhodamine 110; cyanine dyes, e.g. Cy3, Cy5 and Cy7 dyes; Alexa dyes, e.g. Alexa-fluor-555; coumarin, Diethylaminocoumarin, umbelliferone; benzimide dyes, e.g. Hoechst 33258; phenanthridine dyes, e.g. Texas Red; ethidium dyes; acridine dyes; carbazole dyes; phenoxazine dyes; porphyrin dyes; polymethine dyes, BODIPY dyes, quinoline dyes, Pyrene, Fluorescein Chlorotriazinyl, R110, Eosin, JOE, R6G, Tetramethylrhodamine, Lissamine, ROX, Napthofluorescein, and the like.

Hybridization can be carried out under suitable hybridization conditions, which may vary in stringency as desired. Typical conditions are sufficient to produce probe/target complexes on a solid surface between complementary binding members, i.e., between surface-bound subject probes and complementary mRNAs in a sample. In certain embodiments, stringent hybridization conditions can be employed.

Hybridization is typically performed under stringent hybridization conditions. Standard hybridization techniques (e.g. under conditions sufficient to provide for specific binding of target mRNAs in the sample to the probes) are described in Kallioniemi et al., *Science* 258:818-821 (1992) and WO 93/18186. Several guides to general techniques are available, e.g., Tijssen, *Hybridization with Nucleic Acid Probes*, Parts I and II (Elsevier, Amsterdam 1993). For descriptions of techniques suitable for in situ hybridizations, see Gall et al. *Meth. Enzymol.*, 21:470-480 (1981); and Angerer et al. in *Genetic Engineering: Principles and Methods* (Setlow and Hollaender, Eds.) Vol 7, pgs 43-65 (Plenum Press, New York 1985). Selection of appropriate conditions, including temperature, salt concentration, polynucleotide concentration, hybridization time, stringency of washing conditions, and the like will depend on experimental design, including source of sample, identity of capture agents, degree of complementarity expected, etc., and may be determined as a matter of routine experimentation for those of ordinary skill in the art. Those of ordinary skill will readily recognize that alternative but comparable hybridization and wash conditions can be utilized to provide conditions of similar stringency.

After the mRNA hybridization procedure, the surface bound polynucleotides are typically washed to remove unbound nucleic acids. Washing may be performed using any convenient washing protocol, where the washing conditions are typically stringent, as described above. The hybridization of the target mRNAs to the probes is then detected using standard techniques.

IHC staining of tissue sections has been shown to be a reliable method of assessing or detecting presence of proteins in a sample. Immunohistochemistry techniques utilize an antibody to probe and visualize cellular antigens in situ, generally by chromogenic or fluorescent methods. Thus, antibodies or antisera, preferably polyclonal antisera, and most preferably monoclonal antibodies specific for each marker are used to detect expression. As discussed in greater detail below, the antibodies can be detected by direct labeling of the antibodies themselves, for example, with radioactive labels, fluorescent labels, hapten labels such as, biotin, or an enzyme such as horse radish peroxidase or alkaline phosphatase. Alternatively, unlabeled primary antibody is used in conjunction with a labeled secondary antibody, comprising antisera, polyclonal antisera or a monoclonal antibody specific for the primary antibody. Immunohistochemistry protocols and kits are well known in the art and are commercially available. Automated systems for slide preparation and IHC processing are available commercially. The Ventana® BenchMark XT system is an example of such an automated system.

Standard immunological and immunoassay procedures can be found in *Basic and Clinical Immunology* (Stites & Terr eds., 7th ed. 1991). Moreover, the immunoassays can be performed in any of several configurations, which are reviewed extensively in Enzyme Immunoassay (Maggio, ed., 1980); and Harlow & Lane, supra. For a review of the general immunoassays, see also *Methods in Cell Biology: Antibodies in Cell Biology*, volume 37 (Asai, ed. 1993); *Basic and Clinical Immunology* (Stites & Ten, eds., 7th ed. 1991).

Commonly used assays to detect protein level of a biomarker include noncompetitive assays, e.g., sandwich assays, and competitive assays. Typically, an assay such as an ELISA assay can be used. ELISA assays are known in the art, e.g., for assaying a wide variety of tissues and samples, including blood, plasma, serum or bone marrow.

A wide range of immunoassay techniques using such an assay format are available, see, e.g., U.S. Pat. Nos. 4,016,043, 4,424,279, and 4,018,653, which are hereby incorporated by reference in their entireties. These include both single-site and two-site or "sandwich" assays of the non-competitive types, as well as in the traditional competitive binding assays. These assays also include direct binding of a labeled antibody to a target biomarker. Sandwich assays are commonly used assays. A number of variations of the sandwich assay technique exist. For example, in a typical forward assay, an unlabelled antibody is immobilized on a solid substrate, and the sample to be tested brought into contact with the bound molecule. After a suitable period of incubation, for a period of time sufficient to allow formation of an antibody-antigen complex, a second antibody specific to the antigen, labeled with a reporter molecule capable of producing a detectable signal is then added and incubated, allowing time sufficient for the formation of another complex of antibody-antigen-labeled antibody. Any unreacted material is washed away, and the presence of the antigen is determined by observation of a signal produced by the reporter molecule. The results may either be qualitative, by simple observation of the visible signal, or may be quantitated by comparing with a control sample containing known amounts of biomarker.

Variations on the forward assay include a simultaneous assay, in which both sample and labeled antibody are added simultaneously to the bound antibody. These techniques are well known to those skilled in the art, including any minor variations as will be readily apparent. In a typical forward sandwich assay, a first antibody having specificity for the biomarker is either covalently or passively bound to a solid surface. The solid surface may be glass or a polymer, the most commonly used polymers being cellulose, polyacrylamide, nylon, polystyrene, polyvinyl chloride, or polypropylene. The solid supports may be in the form of tubes, beads, discs of microplates, or any other surface suitable for conducting an immunoassay. The binding processes are well-known in the art and generally consist of cross-linking covalently binding or physically adsorbing, the polymer-antibody complex is washed in preparation for the test sample. An aliquot of the sample to be tested is then added to the solid phase complex and incubated for a period of time sufficient (e.g. 2-40 minutes or overnight if more convenient) and under suitable conditions (e.g., from room temperature to 40° C. such as between 25° C. and 32° C. inclusive) to allow binding of any subunit present in the antibody. Following the incubation period, the antibody subunit solid phase is washed and dried and incubated with a second antibody specific for a portion of the biomarker. The second antibody is linked to a reporter molecule which is used to indicate the binding of the second antibody to the molecular marker.

In some embodiments, flow cytometry (FACS) can be used to detect the protein level of a biomarker. Surface proteins can be detected using antibodies against specific biomarkers. The flow cytometer detects and reports the intensity of the fluorichrome-tagged antibody, which indicates the expression level of the biomarker. Non-fluorescent cytoplasmic proteins can also be observed by staining permeablized cells. The stain can either be a fluorescence compound able to bind to certain molecules, or a fluorichrome-tagged antibody to bind the molecule of choice.

An alternative method involves immobilizing the target biomarkers in the sample and then exposing the immobilized target to specific antibody, which may or may not be labeled with a reporter molecule. Depending on the amount of target and the strength of the reporter molecule signal, a bound target may be detectable by direct labeling with the antibody. Alternatively, a second labeled antibody, specific to the first antibody is exposed to the target-first antibody complex to form a target-first antibody-second antibody tertiary complex. The complex is detected by the signal emitted by a labeled reporter molecule.

In the case of an enzyme immunoassay, an enzyme is conjugated to the second antibody, generally by means of glutaraldehyde or periodate. As will be readily recognized, however, a wide variety of different conjugation techniques exist, which are readily available to the skilled artisan. Commonly used enzymes include horseradish peroxidase, glucose oxidase, beta-galactosidase, and alkaline phosphatase, and other are discussed herein. The substrates to be used with the specific enzymes are generally chosen for the production, upon hydrolysis by the corresponding enzyme, of a detectable color change. Examples of suitable enzymes include alkaline phosphatase and peroxidase. It is also possible to employ fluorogenic substrates, which yield a fluorescent product rather than the chromogenic substrates noted above. In all cases, the enzyme-labeled antibody is added to the first antibody-molecular marker complex, allowed to bind, and then the excess reagent is washed away. A solution containing the appropriate substrate is then added to the complex of antibody-antigen-antibody. The substrate will react with the enzyme linked to the second antibody, giving a qualitative visual signal, which may be further quantitated, usually spectrophotometrically, to give an indication of the amount of biomarker which was present in the sample. Alternately, fluorescent compounds, such as fluorescein and rhodamine, can be chemically coupled to antibodies without altering their binding capacity. When activated by illumination with light of a particular wavelength, the fluorochrome-labeled antibody adsorbs the light energy, inducing a state to excitability in the molecule, followed by emission of the light at a characteristic color visually detectable with a light microscope. As in the EIA, the fluorescent labeled antibody is allowed to bind to the first antibody-molecular marker complex. After washing off the unbound reagent, the remaining tertiary complex is then exposed to the light of the appropriate wavelength, the fluorescence observed indicates the presence of the molecular marker of interest. Immunofluorescence and EIA techniques are both very well established in the art and are discussed herein.

In some embodiments, the methods provided herein include determining the protein levels of two or more of these biomarkers. In some embodiments, the methods include determining the protein levels of three or more of these biomarkers. In some embodiments, the methods include determining the protein levels of four or more of these biomarkers. In some embodiments, the methods include determining the protein levels of five of these biomarkers.

3.4. Reference Levels and Reference Ratios

In some embodiments, the reference expression level of a biomarker or the reference ratio between expression levels of two biomarkers can be determined based on statistical analysis of data from previous clinical trials, including outcome of a group of patients, namely, the patients' responsiveness to an FTI treatment, as well as the expression levels of the biomarker or ratio of expression levels between biomarkers of the group of patients. A number of statistical methods are well known in the art to determine the reference level (or referred to as the "cut-off value") of one or more biomarkers when used to predict the responsiveness of a patient to a particular treatment, or to stratify patients for a particular treatment.

One method of the invention includes analyzing gene expression profiles for biomarkers identified herein that distinguish responder from non-responder to determine the reference expression level for one or more biomarkers. Comparisons between responders and non-responders can be performed using the Mann-Whitney U-test, Chi-square test, or Fisher's Exact test. Analysis of descriptive statistics and comparisons can be performed using SigmaStat Software (Systat Software, Inc., San Jose, Calif., USA).

In some embodiments, a classification and regression tree (CART) analysis can be adopted to determine the reference level. CART analysis is based on a binary recursive partitioning algorithm and allows for the discovery of complex predictor variable interactions that may not be apparent with more traditional methods, such as multiple linear regression. Binary recursive partitioning refers to the analysis that is: 1) binary, meaning there were two possible outcome variables, namely "responders" and "non-responders," with the effect of splitting patients into 2 groups; 2) recursive, meaning the analysis can be performed multiple times; and 3) partitioned, meaning the entire data set can be split into sections. This analysis also has the ability to eliminate predictor variables with poor performance. The classification tree can be built using Salford Predictive Modeler v6.6 (Salford Systems, San Diego, Calif., USA).

Articles of this invention are representations of the gene expression profiles useful for predicting the responsiveness of a cancer patient to an FTI treatment that are reduced to a medium that can be automatically read such as computer readable media (magnetic, optical, and the like). The articles can also include instructions for assessing the gene expression profiles in such media. For example, the articles may comprise a CD-ROM having computer instructions for comparing gene expression profiles of biomarkers described above. The articles may also have gene expression profiles digitally recorded therein so that they may be compared with gene expression data from patient samples. Alternatively, the profiles can be recorded in different representational format. Clustering algorithms such as those incorporated in "OMNIVIZ" and "TREE VIEW" computer programs mentioned above can best assist in the visualization of such data.

Receiver Operator Characteristic (ROC) analysis can be utilized to determine the reference expression level, or reference expression ratio, or test the overall predictive value of individual genes and/or multigene classifiers. A review of the ROC analysis can be found in Soreide, J Clin Pathol 10.1136 (2008), which is hereby incorporated by reference in its entirety.

The reference level can be determined from the ROC curve of the training set to ensure both high sensitivity and high specificity. To determine how many biomarkers are needed to be included in the predictor, leave-one-out cross validation (LOOCV) can be used. The response scores for the 'left-out' samples based on different numbers of genes are recorded. The performances of the predictors with different numbers of genes can be assessed based on misclassification error rate, sensitivity, specificity, p values measuring the separation of Kaplan-Meier curves of the two predicted groups.

The Top Scoring Pair (TSP) algorithm first introduced by Geman et al. (2004) can be used. In essence, the algorithm ranks all the gene pairs (genes i and j) based on the absolute difference (Dij) in the frequency of event where gene i has higher expression value than gene j in samples among class C1 to C2. In the cases of there are multiple top scoring pairs (all sharing the same Dij), the top pair by a secondary rank score that measures the magnitude to which inversions of gene expression levels occur from one class to the other within a pair of genes is selected. The top pair with highest frequency of absolute Dij >2 fold in all samples will be selected as candidate pair. The candidate pair can then be assessed in an independent testing data set. Leave-one-out cross validation (LOOCV) can be carried out in the training data set to evaluate how the algorithm perform. The performances of the predictors can be assessed based on maximum misclassification error rate. All the statistical analyses can be done using R (R Development Core Team, 2006).

A review of the methods and statistic tools useful for determining a reference level can be found in James Westgard, Ph.D., Basic Methods Validation, 3d edition (2008), which is hereby incorporated by reference in its entirety. Specific references are made to Chapter 9 ("How is reportable range of a method determined") and Chapter 15 ("How is a reference interval verified").

Clinically reportable range (CRR) is the range of analyte values that a method can measure, allowing for specimen dilution, concentration, or other pretreatment used to extend the direct analytical measurement range. As provided in the Basic Methods Validation by Dr. Westgard, the experiment to be performed is often called a "linearity experiment," though there technically is no requirement that a method provide a linear response unless two-point calibration is being used. This range can also be referred as the "linear range," "analytical range," or "working range" for a method.

The reportable range is assessed by inspection of the linearity graph. That inspection can involve manually drawing the best straight line through the linear portion of the points, drawing a point-to-point line through all the points then comparing with the best straight line, or fitting a regression line through the points in the linear range. There are more complicated statistical calculations that are recommended in some guidelines, such as Clinical Laboratory Standards Institute (CLSI)'s EP-6 protocol for evaluating the linearity of analytical methods. But it is commonly accepted that the reportable range can be adequately determined from a "visual" assessment, i.e., by manually drawing the best straight line that fits the lowest points in the series. The Clinical Laboratory Standards Institute (CLSI) recommends a minimum of at least 4-preferably 5-different levels of concentrations. More than 5 can be used, particularly if the upper limit of reportable range needs to be maximized, but 5 levels are convenient and almost always sufficient.

A reference interval is typically established by assaying specimens that are obtained from individuals that meet carefully defined criteria (reference sample group). Protocols such as those of the International Federation of Clinical Chemistry (IFCC) Expert Panel on Theory of Reference Values and the CLSI delineate comprehensive systematic processes that use carefully selected reference sample groups to establish reference intervals. These protocols typically need a minimum of 120 reference individuals for each group (or subgroup) that needs to be characterized.

The CLSI Approved Guideline C28-A2 describes different ways for a laboratory to validate the transference of established reference intervals to the individual laboratory that includes 1. Divine judgment, wherein the laboratory simply reviews the information submitted and subjectively verifies that the reference intervals are applicable to the adopting laboratory's patient population and test methods; 2. Verification with 20 samples, wherein experimental validation is performed by collecting and analyzing specimens from 20 individuals who represent the reference sample population; 3. Estimation with 60 samples, wherein an experimental validation is performed by collecting and analyzing specimens from 60 individuals who represent the reference sample population, and the actual reference interval is estimated and compared to the claimed or reported interval using a statistical formula comparing the means and standard deviations of the two populations; and 4. Calculation from comparative method, wherein one can adjust or correct the claimed or reported reference intervals on the basis of the observed methodological bias and the mathematical relationship demonstrated between the analytical methods being used.

A person of ordinary skill in the art would understand that the reference expression level of the biomarkers disclosed herein as well as the reference ratios between two biomarkers can be determined by one or more methods as provided herein or other methods known in the art.

5. Mutant HRAS as a Biomarker for FTI Treatment 5.1. HRAS Mutation Status

The HRAS protein is involved in regulating cell division in response to growth factor stimulation. Growth factors act by binding cell surface receptors that span the cell's plasma membrane. Once activated, receptors stimulate signal transduction events in the cytoplasm, a process by which proteins and second messengers relay signals from outside the cell to the cell nucleus and instruct the cell to grow or divide. HRAS is localized in the plasma membrane, and is an early player in many signal transduction pathways. HRAS acts as a molecular on/off switch—once it is turned on it recruits and activates proteins necessary for the propagation of the receptor's signal. In certain tumors, mutations in HRAS or its upstream effectors cause it to be permanently on, resulting in persistent activation of downstream growth and proliferation signals that drive tumor cell growth. FTIs work to prevent the aberrant growth and proliferation of cells that are dependent on these signaling pathways by inhibiting protein farnesylation and subsequent membrane localization of HRAS, thereby switching HRAS off.

FTIs such as tipifarnib prevent protein farnesylation, a type of protein modification known as prenylation, which along with other protein modifications, allows membrane localization of HRAS where it can receive and transmit extracellular signals implicated in cancer initiation and development. FTIs such as tipifarnib can block HRAS farnesylation and subsequent membrane localization, and inhibit oncogenic, HRAS-driven cellular transformation in vitro and in vivo. While K-ras and N-ras similarly utilize protein farnesylation, they can also utilize a related prenylation pathway that also leads to membrane localization. Meanwhile, HRAS membrane localization is solely dependent on protein farnesylation.

The head and neck cancers and the lung cancers to be treated by methods provided herein have HRAS mutations. Methods provided herein or otherwise known in the art can be used to determine the mutation status of an HRAS gene. In some embodiments, the mutation status of an HRAS gene can be determined an NGS-based assay. In some embodiments, the mutation status of an HRAS gene can be determined by a qualitative PCR-based assay. A qualitative PCR based assay can be technically similar to the PCR-based assays already developed and approved by the FDA for K-ras. In some embodiments, mutation status of an HRAS gene can be determined in the form of a companion diagnostic to the FTI treatment, such as the tipifarnib treatment. The companion diagnostic can be performed at the clinic site where the patient receives the tipifarnib treatment, or at a separate site.

Provided herein are methods of treating EGFR inhibitor-refractory squamous cell carcinoma of the head and neck (SCCHN), wherein the SCCHN has an HRAS mutation, comprising administering to the subject a farnesyltransferase inhibitor (FTI). In certain embodiments, said HRAS mutation comprises an amino acid substitution at a codon selected from a group consisting of G12, G13, Q61, Q22, K117, A146 and any combination thereof. In certain embodiments, said SCCHN does not have K-Ras mutation or N-Ras mutation. In certain embodiments, said SCCHN has wild type K-Ras and wild type N-Ras. In certain embodiments, said SCCHN is HPV negative. In certain embodiments, said SCCHN is HPV positive. In certain embodiments, said SCCHN is at an advanced stage or metastatic. In certain embodiments, said SCCHN is relapsed SCCHN. In specific embodiments, the SCCHN is SCCHN of the trachea. In specific embodiments, the SCCHN is SCCHN of the maxilla. In specific embodiments, the SCCHN is SCCHN of the oral cavity. In certain embodiments, the EGFR inhibitor is cetuximab. In certain embodiments, the EGFR inhibitor is erlotinib. In certain embodiments, the EGFR inhibitor is gefitinib. In certain embodiments, the EGFR inhibitor is panitumumab. In certain embodiments, the FTI is tipifarnib. In certain embodiments, said FTI is administered in combination with chemotherapy. In certain embodiments, said chemotherapy comprises a platinum-based therapy, a taxane, or a combination thereof.

Provided herein are methods to treat SCCHN in a subject with an FTI or selecting SCCHN patients for an FTI treatment based on the presence of a HRAS mutation, wherein the SCCHN is refractory to treatment with an EGFR inhibitor. In some embodiments, the SCCHN is HPV negative. In some embodiments, said SCCHN is HPV positive. In some embodiments, the methods include (a) determining the SCCHN to be refractory to treatment with an EGFR inhibitor, (b) determining the SCCHN patient to have a HRAS mutation, and subsequently (c) administering a therapeutically effective amount of tipifarnib to the patient. In some embodiments, provided herein are methods of treating an EGFR-inhibitor-resistant squamous cell carcinoma of the head and neck in a subject with an FTI. In some embodiments, the EGFR inhibitor is cetuximab. In certain embodiments, the EGFR inhibitor is erlotinib. In certain embodiments, the EGFR inhibitor is gefitinib. In certain embodiments, the EGFR inhibitor is panitumumab. In some embodiments, the EGFR inhibitor is panitumumab. In certain embodiments, said tipifarnib is administered in combination with chemotherapy. In certain embodiments, said chemotherapy comprises a platinum-based therapy, a taxane, or a combination thereof.

In some embodiments, provided herein are methods to treat SCCHN in a subject with an FTI or selecting SCCHN patients for an FTI treatment based on the presence of a HRAS mutation, wherein the patient has never been treated with an EGFR inhibitor. In some embodiments, the SCCHN is HPV negative. In some embodiments, said SCCHN is HPV positive. In some embodiments, the methods include (a) determining that the patient has never been treated with an EGFR inhibitor, (b) determining the SCCHN patient to have a HRAS mutation, and subsequently (c) administering a therapeutically effective amount of tipifarnib to the patient and not administering an EGFR inhibitor. In some embodiments, the EGFR inhibitor is cetuximab. In certain embodiments, the EGFR inhibitor is erlotinib. In certain embodiments, the EGFR inhibitor is gefitinib. In certain embodiments, the EGFR inhibitor is panitumumab. In some embodiments, the EGFR inhibitor is panitumumab. In certain embodiments, said tipifarnib is administered in combination with chemotherapy. In certain embodiments, said chemotherapy comprises a platinum-based therapy, a taxane, or a combination thereof.

Provided herein are methods of treating EGFR inhibitor-refractory lung squamous cell carcinoma (lung SCC), wherein the lung SCC has an HRAS mutation, comprising administering to the subject a farnesyltransferase inhibitor (FTI). In certain embodiments, said HRAS mutation comprises an amino acid substitution at a codon selected from a group consisting of G12, G13, Q61, Q22, K117, A146 and any combination thereof. In certain embodiments, said lung SCC does not have K-Ras mutation or N-Ras mutation. In certain embodiments, said lung SCC has wild type K-Ras and wild type N-Ras. In certain embodiments, said lung SCC is HPV negative. In certain embodiments, said lung SCC is HPV positive. In certain embodiments, said lung SCC is at an advanced stage or metastatic. In certain embodiments, said lung SCC is relapsed lung SCC. In certain embodiments, the EGFR inhibitor is cetuximab. In certain embodiments, the EGFR inhibitor is erlotinib. In certain embodiments, the EGFR inhibitor is gefitinib. In certain embodiments, the EGFR inhibitor is panitumumab. In certain embodiments, the FTI is tipifarnib. In certain embodiments, said FTI is administered in combination with chemotherapy. In certain embodiments, said chemotherapy comprises a platinum-based therapy, a taxane, or a combination thereof.

Provided herein are methods to treat lung SCC in a subject with an FTI or selecting lung SCC patients for an FTI treatment based on the presence of a HRAS mutation, wherein the lung SCC is refractory to treatment with an EGFR inhibitor. In some embodiments, the lung SCC is HPV negative. In some embodiments, said lung SCC is HPV positive. In some embodiments, the methods include (a) determining the lung SCC to be refractory to treatment with an EGFR inhibitor, (b) determining the lung SCC patient to have a HRAS mutation, and subsequently (c) administering a therapeutically effective amount of tipifarnib to the patient. In some embodiments, provided herein are methods of treating an EGFR-inhibitor-resistant lung squamous cell carcinoma in a subject with an FTI. In some embodiments, the EGFR inhibitor is cetuximab. In certain embodiments, the EGFR inhibitor is erlotinib. In certain embodiments, the EGFR inhibitor is gefitinib. In certain embodiments, the EGFR inhibitor is panitumumab. In some embodiments, the EGFR inhibitor is panitumumab. In certain embodiments, said tipifarnib is administered in combination with chemotherapy. In certain embodiments, said chemotherapy comprises a platinum-based therapy, a taxane, or a combination thereof.

In some embodiments, provided herein are methods to treat lung SCC in a subject with an FTI or selecting lung SCC patients for an FTI treatment based on the presence of a HRAS mutation, wherein the patient has never been treated with an EGFR inhibitor. In some embodiments, the lung SCC is HPV negative. In some embodiments, said lung SCC is HPV positive. In some embodiments, the methods include (a) determining that the patient has never been treated with an EGFR inhibitor, (b) determining the lung SCC patient to have a HRAS mutation, and subsequently (c) administering a therapeutically effective amount of tipifarnib to the patient and not administering an EGFR inhibitor. In some embodiments, the EGFR inhibitor is cetuximab. In certain embodiments, the EGFR inhibitor is erlotinib. In certain embodiments, the EGFR inhibitor is gefitinib. In certain embodiments, the EGFR inhibitor is panitumumab. In some embodiments, the EGFR inhibitor is panitumumab. In certain embodiments, said tipifarnib is administered in combination with chemotherapy. In certain embodiments, said chemotherapy comprises a platinum-based therapy, a taxane, or a combination thereof.

In some embodiments, the HRAS mutation is a mutation at a codon selected from the group consisting of G12, G13, Q61, Q22, K117, and A146. In some embodiments, the HRAS mutation can be a mutation selected from the group consisting of the amino acid substitutions of G12R, G12V, G13C, G13R, Q61L, Q61R, Q22K, K117N, and A146P. In some embodiments, the mutation can be a mutation at another codon that results in activation of HRAS protein.

In some embodiments, the methods provided herein further include (a) determining the presence or absence of a K-Ras mutation and a N-Ras mutation in a sample from the subject, and subsequently (b) administering a therapeutically effective amount of an FTI to the subject if the sample does not have the K-Ras mutation or the N-Ras mutation. In some embodiments, the method includes administering a therapeutically effective amount of an FTI to the subject if the sample has wild type K-Ras and wild type N-Ras. In certain embodiments, said FTI is administered in combination with chemotherapy. In certain embodiments, said chemotherapy comprises a platinum-based therapy, a taxane, or a combination thereof.

In some embodiments, the K-Ras mutation is $K_A$-Ras mutation. In some embodiments, the K-Ras mutation is $K_B$-Ras mutation. In some embodiments, the K-Ras mutation is a combination of $K_A$-Ras mutation and a $K_B$-Ras mutation. The K-Ras mutation can include a mutation at a codon selected from the group consisting of G12, G13, and Q61 of $K_A$-Ras, $K_B$-Ras, or both. In some embodiments, the $K_A$-Ras mutation can include a mutation selected from the group consisting of the amino acid substitutions G12C, G12D, G12A, G12V, G12S, G12F, G12R, G12N, G13C, G13D, G13R, G13S, G13N, Q61 K, Q61 H, Q61 L, Q61 P, Q61 R and A146V. In some embodiments, the $K_B$-Ras mutation can include a mutation selected from the group consisting of the amino acid substitutions G12C, G12D, G12A, G12V, G12S, G12F, G12R, G12N, G13C, G13D, G13R, G13S, G13N, Q61 K, Q61 H, Q61 L, Q61 P, Q61 R and A146V.

In some embodiments, the N-Ras mutation can include at least one mutation at a codon selected from the group consisting of G12, G13, G15, G60 and Q61. In some embodiments, the N-Ras mutation can include at least one mutation at a codon selected from the group consisting of G12, G13, and Q61. In some embodiments, the N-Ras mutation can include at least one mutation selected from the group consisting of the amino acid substitutions of G12C, G12D, G12F, G12S, G12A, G12V, G12R, G13C, G13R, G13A, G13D, G13V, G15W, G60E, Q61P, Q61L, Q61R, Q61K, Q61H and Q61E.

In some embodiments, the sample is determined to not have amino acid substitution at G12, G13, and Q61 of K-Ras, and also not have amino acid substitution at G12, G13, and Q61 of N-Ras. In some embodiments, the sample is determined to not have any K-Ras mutation or any N-Ras mutation. In some embodiments, the sample is determined to have wild type K-Ras and wild type N-Ras.

In some embodiments, the method provided herein includes (a) determining the presence or absence of a HRAS mutation, a K-Ras mutation, and a N-Ras mutation in a sample from the subject, and subsequently (b) administering a therapeutically effective amount of an FTI to the subject if the sample is determined to have a HRAS mutation, but no K-Ras mutation or N-Ras mutation. The sample can be a tumor sample. In some embodiments, the methods include (a) determining the SCCHN patient to have a HRAS mutation and wild type K-Ras and wild type N-Ras, and subsequently (b) administering a therapeutically effective amount of an FTI to the subject. In some embodiments, the FTI is tipifarnib. In certain embodiments, said FTI is administered in combination with chemotherapy. In certain embodiments, said chemotherapy comprises a platinum-based therapy, a taxane, or a combination thereof.

Provided herein are methods to treat the SCCHN in a subject with an FTI, and methods for selecting cancer patients for an FTI treatment based on the presence of a HRAS mutation. Provided herein are also methods to treat a premalignant head and neck condition in a subject with an FTI, and methods for selecting patients with a premalignant head and neck condition for an FTI treatment based on HRAS mutation status.

In some embodiments, provided herein are methods to treat SCCHN in a subject with an FTI or selecting SCCHN patients for an FTI treatment based on the presence of a HRAS mutation. The cancer can be related to Human papillomavirus (HPV+ or HPV positive), or unrelated to HPV (HPV− or HPV negative).

Provided herein are methods for predicting responsiveness of SCCHN patient to an FTI treatment, methods for SCCHN patient population selection for an FTI treatment, and methods for treating SCCHN in a subject with a therapeutically effective amount of an FTI, based on the presence of a HRAS mutation in a sample from the patient. The mutation status of HRAS can be detected at the nucleic acid or protein level. In some embodiments, the HRAS mutation status is determined by analyzing nucleic acids obtained from the sample. In some embodiments, the HRAS mutation status is determined by analyzing protein obtained from the sample.

In some embodiments, the methods include (a) determining the lung SCC patient to have a HRAS mutation and wild type K-Ras and wild type N-Ras, and subsequently (b) administering a therapeutically effective amount of an FTI to the subject. In some embodiments, the FTI is tipifarnib. In certain embodiments, said FTI is administered in combination with chemotherapy. In certain embodiments, said chemotherapy comprises a platinum-based therapy, a taxane, or a combination thereof.

Provided herein are methods to treat the lung SCC in a subject with an FTI, and methods for selecting cancer patients for an FTI treatment based on the presence of a HRAS mutation. Provided herein are also methods to treat a premalignant lung condition in a subject with an FTI, and methods for selecting patients with a premalignant lung condition for an FTI treatment based on HRAS mutation status.

In some embodiments, provided herein are methods to treat lung SCC in a subject with an FTI or selecting lung SCC patients for an FTI treatment based on the presence of a HRAS mutation. The cancer can be related to Human papillomavirus (HPV+ or HPV positive), or unrelated to HPV (HPV− or HPV negative).

Provided herein are methods for predicting responsiveness of lung SCC patient to an FTI treatment, methods for lung SCC patient population selection for an FTI treatment, and methods for treating lung SCC in a subject with a therapeutically effective amount of an FTI, based on the presence of a HRAS mutation in a sample from the patient. The mutation status of HRAS can be detected at the nucleic acid or protein level. In some embodiments, the HRAS mutation status is determined by analyzing nucleic acids obtained from the sample. In some embodiments, the HRAS mutation status is determined by analyzing protein obtained from the sample.

In some embodiments, the HRAS mutation status is determined by analyzing nucleic acids obtained from the sample. The nucleic acids may be mRNA or genomic DNA molecules from the test subject. Methods for determining Ras mutation status by analyzing nucleic acids are well known in the art. In some embodiments, the methods include sequencing, Polymerase Chain Reaction (PCR), DNA microarray, Mass Spectrometry (MS), Single Nucleotide Polymorphism (SNP) assay, denaturing high-performance liquid chromatography (DHPLC), or Restriction Fragment Length Polymorphism (RFLP) assay. In some embodiments, the Ras mutation status is determined using standard sequencing methods, including, for example, Sanger sequencing, next generation sequencing (NGS). In some embodiments, the Ras mutation status is determined using MS.

In some embodiments, the HRAS mutation status is determined by analyzing protein obtained from the sample.

The mutated Ras H-protein can be detected by a variety of immunohistochemistry (IHC) approaches, Immunoblotting assay, Enzyme-Linked Immunosorbent Assay (ELISA) or other immunoassay methods known in the art.

As a person of ordinary skill in the art would understand, any methods described herein or otherwise known in the art for analyzing Ras mutation can be used to determining the presence or absence of a HRAS mutation.

5.2. Samples

In some embodiments, methods provided herein include obtaining a sample from the subject. In some embodiments, the sample is a tumor sample. In some embodiments, the sample used in the present methods includes a biopsy (e.g., a tumor biopsy). The biopsy can be from any organ or tissue, for example, skin, liver, lung, heart, colon, kidney, bone marrow, teeth, lymph node, hair, spleen, brain, breast, or other organs. Any biopsy technique known by those skilled in the art can be used for isolating a sample from a subject, for instance, open biopsy, close biopsy, core biopsy, incisional biopsy, excisional biopsy, or fine needle aspiration biopsy.

The sample used in the methods provided herein includes body fluids from a subject. Non-limiting examples of body fluids include blood (e.g., peripheral whole blood, peripheral blood), blood plasma, bone marrow, amniotic fluid, aqueous humor, bile, lymph, menses, serum, urine, cerebrospinal fluid surrounding the brain and the spinal cord, synovial fluid surrounding bone joints.

In one embodiment, the sample is a bone marrow sample. Procedures to obtain a bone marrow sample are well known in the art, including but not limited to bone marrow biopsy and bone marrow aspiration. Bone marrow has a fluid portion and a more solid portion. In bone marrow biopsy, a sample of the solid portion is taken. In bone marrow aspiration, a sample of the fluid portion is taken. Bone marrow biopsy and bone marrow aspiration can be done at the same time and referred to as a bone marrow exam.

In some embodiments, the sample is a blood sample. The blood sample can be obtained using conventional techniques as described in, e.g. Innis et al, editors, PCR Protocols (Academic Press, 1990). White blood cells can be separated from blood samples using convention techniques or commercially available kits, e.g. RosetteSep kit (Stein Cell Technologies, Vancouver, Canada). Sub-populations of white blood cells, e.g. mononuclear cells, NK cells, B cells, T cells, monocytes, granulocytes or lymphocytes, can be further isolated using conventional techniques, e.g. magnetically activated cell sorting (MACS) (Miltenyi Biotec, Auburn, Calif.) or fluorescently activated cell sorting (FACS) (Becton Dickinson, San Jose, Calif.).

In certain embodiments, the sample used in the methods provided herein includes a plurality of cells. Such cells can include any type of cells, e.g., stem cells, blood cells (e.g., PBMCs), lymphocytes, NK cells, B cells, T cells, monocytes, granulocytes, immune cells, or tumor or cancer cells. Specific cell populations can be obtained using a combination of commercially available antibodies (e.g., Quest Diagnostic (San Juan Capistrano, Calif.); Dako (Denmark)).

In certain embodiments, the sample used in the methods provided herein is from a diseased tissue, e.g., from an individual having SCCHN. In some embodiments, the cells can be obtained from the tumor or cancer cells or a tumor tissue, such as a tumor biopsy or a tumor explants. In certain embodiments, the number of cells used in the methods provided herein can range from a single cell to about $10^9$ cells. In some embodiments, the number of cells used in the methods provided herein is about $1\times10^4$, $5\times10^4$, $1\times10^5$, $5\times10^5$, $1\times10^6$, $5\times10^6$, $1\times10^7$, $5\times10^7$, $1\times10^8$, or $5\times10^8$.

The number and type of cells collected from a subject can be monitored, for example, by measuring changes in morphology and cell surface markers using standard cell detection techniques such as flow cytometry, cell sorting, immunocytochemistry (e.g., staining with tissue specific or cell-marker specific antibodies) fluorescence activated cell sorting (FACS), magnetic activated cell sorting (MACS), by examination of the morphology of cells using light or confocal microscopy, and/or by measuring changes in gene expression using techniques well known in the art, such as PCR and gene expression profiling. These techniques can be used, too, to identify cells that are positive for one or more particular markers. Fluorescence activated cell sorting (FACS) is a well-known method for separating particles, including cells, based on the fluorescent properties of the particles (Kamarch, 1987, Methods Enzymol, 151:150-165). Laser excitation of fluorescent moieties in the individual particles results in a small electrical charge allowing electromagnetic separation of positive and negative particles from a mixture. In one embodiment, cell surface marker-specific antibodies or ligands are labeled with distinct fluorescent labels. Cells are processed through the cell sorter, allowing separation of cells based on their ability to bind to the antibodies used. FACS sorted particles may be directly deposited into individual wells of 96-well or 384-well plates to facilitate separation and cloning.

In certain embodiments, subsets of cells are used in the methods provided herein. Methods to sort and isolate specific populations of cells are well-known in the art and can be based on cell size, morphology, or intracellular or extracellular markers. Such methods include, but are not limited to, flow cytometry, flow sorting, FACS, bead based separation such as magnetic cell sorting, size-based separation (e.g., a sieve, an array of obstacles, or a filter), sorting in a microfluidics device, antibody-based separation, sedimentation, affinity adsorption, affinity extraction, density gradient centrifugation, laser capture microdissection, etc.

5.3. Cancers

Provided herein are methods of treating EGFR inhibitor-refractory squamous cell carcinoma of the head and neck (SCCHN), wherein the SCCHN has an HRAS mutation, comprising administering to the subject a farnesyltransferase inhibitor (FTI). In certain embodiments, said HRAS mutation comprises an amino acid substitution at a codon selected from a group consisting of G12, G13, Q61, Q22, K117, A146, and any combination thereof. In certain embodiments, said SCCHN does not have K-Ras mutation or N-Ras mutation. In certain embodiments, said SCCHN has wild type K-Ras and wild type N-Ras. In certain embodiments, said SCCHN is HPV negative. In certain embodiments, said SCCHN is HPV positive. In certain embodiments, said SCCHN is at an advanced stage or metastatic. In certain embodiments, said SCCHN is relapsed SCCHN. In specific embodiments, the SCCHN is SCCHN of the trachea. In specific embodiments, the SCCHN is SCCHN of the maxilla. In specific embodiments, the SCCHN is SCCHN of the oral cavity. In certain embodiments, the EGFR inhibitor is cetuximab. In certain embodiments, the EGFR inhibitor is erlotinib. In certain embodiments, the EGFR inhibitor is gefitinib. In certain embodiments, the EGFR inhibitor is panitumumab. In certain embodiments, the FTI is tipifarnib. In certain embodiments, said FTI is administered in combination with chemotherapy. In certain embodiments, said chemotherapy comprises a platinum-based therapy, a taxane, or a combination thereof.

In some embodiments, provided herein are methods of treating EGFR inhibitor-refractory SCCHN in a subject having an HRAS mutation, comprising administering to the subject an FTI. In certain embodiments, said HRAS mutation comprises an amino acid substitution at a codon selected from a group consisting of G12, G13, Q61, Q22, K117, A146, and any combination thereof. In certain embodiments, said SCCHN does not have K-Ras mutation or N-Ras mutation. In certain embodiments, said SCCHN has wild type K-Ras and wild type N-Ras. In certain embodiments, said SCCHN is HPV negative. In certain embodiments, said SCCHN is HPV positive. In certain embodiments, said SCCHN is at an advanced stage or metastatic. In certain embodiments, said SCCHN is relapsed SCCHN. In specific embodiments, the SCCHN is SCCHN of the trachea. In specific embodiments, the SCCHN is SCCHN of the maxilla. In specific embodiments, the SCCHN is SCCHN of the oral cavity. In certain embodiments, the EGFR inhibitor is cetuximab. In certain embodiments, the EGFR inhibitor is erlotinib. In certain embodiments, the EGFR inhibitor is gefitinib. In certain embodiments, the EGFR inhibitor is panitumumab. In certain embodiments, the FTI is tipifarnib. In certain embodiments, said FTI is administered in combination with chemotherapy. In certain embodiments, said chemotherapy comprises a platinum-based therapy, a taxane, or a combination thereof.

In some embodiments, provided herein are methods to treat SCCHN in a subject with an FTI or selecting SCCHN patients for an FTI treatment based on the presence of a HRAS mutation. In some embodiments, the SCCHN is HPV negative. In some embodiments, said SCCHN is HPV positive. In some embodiments, the methods include (a) determining a HPV negative SCCHN patient to have a HRAS mutation, and subsequently (b) administering a therapeutically effective amount of tipifarnib to the patient. In certain embodiments, said tipifarnib is administered in combination with chemotherapy. In certain embodiments, said chemotherapy comprises a platinum-based therapy, a taxane, or a combination thereof.

In some embodiments, provided herein are methods to treat SCCHN in a subject with an FTI or selecting SCCHN patients for an FTI treatment based on the presence of a HRAS mutation and resistance to an EGFR inhibitor. In some embodiments, the SCCHN is HPV negative. In some embodiments, said SCCHN is HPV positive. In some embodiments, the methods include (a) determining a HPV negative SCCHN patient to have a HRAS mutation and be resistant to an EGFR inhibitor, and subsequently (b) administering a therapeutically effective amount of tipifarnib to the patient. In certain embodiments, said tipifarnib is administered in combination with chemotherapy. In certain embodiments, said chemotherapy comprises a platinum-based therapy, a taxane, or a combination thereof.

Head and neck squamous cell carcinoma (SCCHN) is the $6^{th}$ most common cancer worldwide, with about 650,000 cases and 200,000 deaths per year worldwide, and about 54,000 new cases per year in the US. It is also the most common cancer in central Asia.

SCCHN has 2 different etiologies and corresponding tumor types. The first subtype is associated with tobacco smoking and alcohol consumption, and unrelated to Human papillomavirus (HPV− or HPV negative). The second subtype is associated with infection with high-risk HPV (HPV+ or HPV positive). The second subtype is largely limited to oropharyngeal cancers. HPV+ tumors are distinct entity with better prognosis and may require differential treatments.

A significant proportion of SCCHN, particularly oropharyngeal cancers, are caused by HPV infection. High-risk HPV subtype 16 accounts for 85% of all HPV+ tumors in SCCHN. P16 can be used as surrogate marker of HPV infection in SCCHN, particularly in the oropharynx. More accurate HPV testing is available and based on E6/E7 detection (Liang C, et al. Cancer Res. 2012; 72:5004-5013).

HPV+ SCCHN show significantly lower EGFR expression levels than HPV− SCCHN. EGFR amplification only occurs in HPV− SCCHN. High EGFR gene copy number and protein expression are associated with poor clinical outcome in advanced SCCHN.

Currently, first-line therapy for recurrent/metastatic SCCHN include platinum-based doublet (e.g., cisplatin/5-FU or carboplatin/paclitaxel), optionally in combination with anti-EGFR antibody therapy (e.g. Cetuximab, Panitumumab, Afatinib). Second-line therapy includes taxanes, methotrexate, and/or cetuximab. Anti-EGFR antibody therapy, such as Cetuximab (a chimeric IgG1) or Panitumumab can be used as a single agent, with chemotherapy (e.g. Platinum/5-FU, Cisplatin), or with radiation therapy. Despite high EGFR expression levels in SCCHN, single-agent response rate for Cetuximab is only 13% with SD rate of 33%, and there is currently no predictive biomarker available.

Drugs in development for SCCHN include those targeting PI3K pathway: BKM120 (buparlisib)+cetuximab, BYL719+cetuximab, Temsirolimus+cetuximab, Rigosertib+cetuximab; those targeting MET pathway: Tivantinib+cetuximab, Ficlatuzumab+cetuximab; those targeting EGFR/HER3 pathway Afatinib+cetuximab±paclitaxel, Patritumab; those targeting FGFR pathway: BGJ398; those targeting CDK4/6-cell cycle pathway: Palbociclib, LEEO11; RTK inhibitor: Anlotinib and chemotherapy: Oral Azacitidine. More recent therapeutic options for SCCHN include immunotherapy, such as anti-PD1 or anti-PDL1 antibodies.

While high cure rates have been achieved for localized and loco-regional disease using surgery, radiation, chemo-radiation, and induction chemotherapy, survival rates for recurrent/metastatic diseases remain very poor, and better treatment options are necessary.

In some embodiments, provided herein are methods to treat SCCHN in a subject with an FTI or selecting SCCHN patients for an FTI treatment based on the presence of a HRAS mutation, wherein the SCCHN is refractory to treatment with an EGFR inhibitor. In some embodiments, the SCCHN is HPV negative. In some embodiments, said SCCHN is HPV positive. In some embodiments, the methods include (a) determining SCCHN to be refractory to treatment with an EGFR inhibitor, (b) determining the SCCHN patient to have a HRAS mutation, and subsequently (c) administering a therapeutically effective amount of tipifarnib to the patient. In some embodiments, provided herein are methods of treating an EGFR-inhibitor-resistant squamous cell carcinoma in a subject with an FTI. In some embodiments, the EGFR inhibitor is cetuximab. In some embodiments, the EGFR inhibitor is erlotinib. In some embodiments, the EGFR inhibitor is gefitinib. In some embodiments, the EGFR inhibitor is panitumumab. In some embodiments, the EGFR inhibitor is panitumumab. In some embodiments, the patient has been treated with an EGFR inhibitor, which resulted in progressive disease. In certain embodiments, said tipifarnib is administered in combination with chemotherapy. In certain embodiments, said chemotherapy comprises a platinum-based therapy, a taxane, or a combination thereof.

In some embodiments, provided herein are methods to treat SCCHN in a subject with an FTI or selecting SCCHN patients for an FTI treatment based on the presence of a HRAS mutation, wherein the patient has never been treated with an EGFR inhibitor. In some embodiments, the SCCHN is HPV negative. In some embodiments, said SCCHN is HPV positive. In some embodiments, the methods include (a) determining that the patient has never been treated with an EGFR inhibitor, (b) determining the SCCHN patient to have a HRAS mutation, and subsequently (c) administering a therapeutically effective amount of tipifarnib to the patient and not administering an EGFR inhibitor. In some embodiments, the EGFR inhibitor is cetuximab. In some embodiments, the EGFR inhibitor is erlotinib. In some embodiments, the EGFR inhibitor is gefitinib. In some embodiments, the EGFR inhibitor is panitumumab. In some embodiments, the EGFR inhibitor is panitumumab. In certain embodiments, said tipifarnib is administered in combination with chemotherapy. In certain embodiments, said chemotherapy comprises a platinum-based therapy, a taxane, or a combination thereof.

The EGFR inhibitor to which the SCCHN is refractory may be any EGFR inhibitor known in the art. The EGFR inhibitor may be an anti-EGFR antibody or antigen-binding fragment thereof, for example, cetuximab (ERBITUX®; Bristol-Myers Squibb/Lilly), panitumumab (VECTIBIX®; Amgen), or zalutumumab (Genmab). The EGFR inhibitor may also be a small molecule inhibitor. Examples of EGFR inhibitors include, but are not limited to, reversible and irreversible inhibitors, such as erlotinib (TARCEVA®; Genentech/Astellas Oncology), AZD9291 (AstraZeneca), gefitinib (IRESSA®; AstraZeneca), icotinib (BPI-2009H; Beta Pharma), rociletinib (CO-1686, AVL-301; Clovis Oncology), poziotinib (NOV120101, HM781-36B; Hanmi Pharmaceutical s/Spectrum Pharmaceuticals), afatinib (BIBW2292; Boehringer Ingelheim), pelitinib (EKB-569; Wyeth Pharmaceuticals), ASP8273 (Astellas), Luminespib (AUY922; Vernalis/Novartis), and XL647 (Exelixis).

In some embodiments, provided herein is a method of treating SCCHN in a subject based on the presence of a HRAS mutation and resistance to an EGFR inhibitor. In some embodiments, the SCCHN can be HPV negative SCCHN. In some embodiments, the SCCHN can be HPV positive SCCHN. In some embodiments, the SCCHN can be relapsed/recurrent SCCHN. In some embodiments, the SCCHN can be metastatic SCCHN. The method provided herein includes (a) determining the presence or absence of a HRAS mutation in a sample from the subject, and subsequently (b) administering a therapeutically effective amount of an FTI to the subject if the sample is determined to have a HRAS mutation. The method provided herein includes (a) determining the presence or absence of a HRAS mutation in a sample from the subject, (b) determining resistance to an EGFR inhibitor, and subsequently (c) administering a therapeutically effective amount of an FTI to the subject if the sample is determined to have a HRAS mutation and be resistant to an EGFR inhibitor. The sample can be a tumor sample. In some embodiments, the methods include (a) determining a SCCHN patient to have a HRAS mutation, and subsequently (b) administering a therapeutically effective amount of an FTI to the subject. In some embodiments, the methods include (a) determining a SCCHN patient to have a HRAS mutation, and (b) determining resistance to an EGFR inhibitor, and, subsequently (c) administering a therapeutically effective amount of an FTI to the subject. In some embodiments, the FTI is tipifarnib. In certain embodiments, said FTI is administered in combination with chemotherapy. In certain embodiments, said chemotherapy comprises a platinum-based therapy, a taxane, or a combination thereof.

Provided herein are methods of treating EGFR inhibitor-refractory lung squamous cell carcinoma (lung SCC), wherein the lung SCC has an HRAS mutation, comprising administering to the subject a farnesyltransferase inhibitor (FTI). In certain embodiments, said HRAS mutation comprises an amino acid substitution at a codon selected from a group consisting of G12, G13, Q61, Q22, K117, A146, and any combination thereof. In certain embodiments, said lung SCC does not have K-Ras mutation or N-Ras mutation. In certain embodiments, said lung SCC has wild type K-Ras and wild type N-Ras. In certain embodiments, said lung SCC is HPV negative. In certain embodiments, said lung SCC is HPV positive. In certain embodiments, said lung SCC is at an advanced stage or metastatic. In certain embodiments, said lung SCC is relapsed lung SCC. In certain embodiments, the EGFR inhibitor is cetuximab. In certain embodiments, the EGFR inhibitor is erlotinib. In certain embodiments, the EGFR inhibitor is gefitinib. In certain embodiments, the EGFR inhibitor is panitumumab. In certain embodiments, the FTI is tipifarnib. In certain embodiments, said FTI is administered in combination with chemotherapy. In certain embodiments, said chemotherapy comprises a platinum-based therapy, a taxane, or a combination thereof.

In some embodiments, provided herein are methods of treating EGFR inhibitor-refractory lung SCC in a subject having an HRAS mutation, comprising administering to the subject an FTI. In certain embodiments, said HRAS mutation comprises an amino acid substitution at a codon selected from a group consisting of G12, G13, Q61, Q22, K117, A146, and any combination thereof. In certain embodiments, said lung SCC does not have K-Ras mutation or N-Ras mutation. In certain embodiments, said lung SCC has wild type K-Ras and wild type N-Ras. In certain embodiments, said lung SCC is HPV negative. In certain embodiments, said lung SCC is HPV positive. In certain embodiments, said lung SCC is at an advanced stage or metastatic. In certain embodiments, said lung SCC is relapsed lung SCC. In certain embodiments, the EGFR inhibitor is cetuximab. In certain embodiments, the EGFR inhibitor is erlotinib. In certain embodiments, the EGFR inhibitor is gefitinib. In certain embodiments, the EGFR inhibitor is panitumumab. In certain embodiments, the FTI is tipifarnib. In certain embodiments, said FTI is administered in combination with chemotherapy. In certain embodiments, said chemotherapy comprises a platinum-based therapy, a taxane, or a combination thereof.

In some embodiments, provided herein are methods to treat lung SCC in a subject with an FTI or selecting lung SCC patients for an FTI treatment based on the presence of a HRAS mutation. In some embodiments, the lung SCC is HPV negative. In some embodiments, said lung SCC is HPV positive. In some embodiments, the methods include (a) determining a HPV negative lung SCC patient to have a HRAS mutation, and subsequently (b) administering a therapeutically effective amount of tipifarnib to the patient. In certain embodiments, said tipifarnib is administered in combination with chemotherapy. In certain embodiments, said chemotherapy comprises a platinum-based therapy, a taxane, or a combination thereof.

In some embodiments, provided herein are methods to treat lung SCC in a subject with an FTI or selecting lung SCC patients for an FTI treatment based on the presence of a HRAS mutation and resistance to an EGFR inhibitor. In some embodiments, the lung SCC is HPV negative. In some embodiments, said lung SCC is HPV positive. In some embodiments, the methods include (a) determining a HPV negative lung SCC patient to have a HRAS mutation and be resistant to an EGFR inhibitor, and subsequently (b) administering a therapeutically effective amount of tipifarnib to the patient. In certain embodiments, said tipifarnib is administered in combination with chemotherapy. In certain embodiments, said chemotherapy comprises a platinum-based therapy, a taxane, or a combination thereof.

In some embodiments, provided herein are methods to treat lung SCC in a subject with an FTI or selecting lung SCC patients for an FTI treatment based on the presence of a HRAS mutation, wherein the lung SCC is refractory to treatment with an EGFR inhibitor. In some embodiments, the lung SCC is HPV negative. In some embodiments, said lung SCC is HPV positive. In some embodiments, the methods include (a) determining lung SCC to be refractory to treatment with an EGFR inhibitor, (b) determining the lung SCC patient to have a HRAS mutation, and subsequently (c) administering a therapeutically effective amount of tipifarnib to the patient. In some embodiments, provided herein are methods of treating an EGFR-inhibitor-resistant squamous cell carcinoma in a subject with an FTI. In some embodiments, the EGFR inhibitor is cetuximab. In some embodiments, the EGFR inhibitor is erlotinib. In some embodiments, the EGFR inhibitor is gefitinib. In some embodiments, the EGFR inhibitor is panitumumab. In some embodiments, the patient has been treated with an EGFR inhibitor, which resulted in progressive disease. In certain embodiments, said tipifarnib is administered in combination with chemotherapy. In certain embodiments, said chemotherapy comprises a platinum-based therapy, a taxane, or a combination thereof.

In some embodiments, provided herein are methods to treat lung SCC in a subject with an FTI or selecting lung SCC patients for an FTI treatment based on the presence of a HRAS mutation, wherein the patient has never been treated with an EGFR inhibitor. In some embodiments, the lung SCC is HPV negative. In some embodiments, said lung SCC is HPV positive. In some embodiments, the methods include (a) determining that the patient has never been treated with an EGFR inhibitor, (b) determining the lung SCC patient to have a HRAS mutation, and subsequently (c) administering a therapeutically effective amount of tipifarnib to the patient and not administering an EGFR inhibitor. In some embodiments, the EGFR inhibitor is cetuximab. In some embodiments, the EGFR inhibitor is erlotinib. In some embodiments, the EGFR inhibitor is gefitinib. In some embodiments, the EGFR inhibitor is panitumumab. In certain embodiments, said tipifarnib is administered in combination with chemotherapy. In certain embodiments, said chemotherapy comprises a platinum-based therapy, a taxane, or a combination thereof.

The EGFR inhibitor to which the lung SCC is refractory may be any EGFR inhibitor known in the art. The EGFR inhibitor may be an anti-EGFR antibody or antigen-binding fragment thereof, for example, cetuximab (ERBITUX®; Bristol-Myers Squibb/Lilly), panitumumab (VECTIBIX®; Amgen), or zalutumumab (Genmab). The EGFR inhibitor may also be a small molecule inhibitor. Examples of EGFR inhibitors include, but are not limited to, reversible and irreversible inhibitors, such as erlotinib (TARCEVA®; Genentech/Astellas Oncology), AZD9291 (AstraZeneca), gefitinib (IRESSA®; AstraZeneca), icotinib (BPI-2009H;

Beta Pharma), rociletinib (CO-1686, AVL-301; Clovis Oncology), poziotinib (NOV120101, HM781-36B; Hanmi Pharmaceutical s/Spectrum Pharmaceuticals), afatinib (BIBW2292; Boehringer Ingelheim), pelitinib (EKB-569; Wyeth Pharmaceuticals), ASP8273 (Astellas), Luminespib (AUY922; Vernalis/Novartis), and XL647 (Exelixis).

In some embodiments, provided herein is a method of treating lung SCC in a subject based on the presence of a HRAS mutation and resistance to an EGFR inhibitor. In some embodiments, the lung SCC can be HPV negative lung SCC. In some embodiments, the lung SCC can be HPV positive lung SCC. In some embodiments, the lung SCC can be relapsed/recurrent lung SCC. In some embodiments, the lung SCC can be metastatic lung SCC. The method provided herein includes (a) determining the presence or absence of a HRAS mutation in a sample from the subject, and subsequently (b) administering a therapeutically effective amount of an FTI to the subject if the sample is determined to have a HRAS mutation. The method provided herein includes (a) determining the presence or absence of a HRAS mutation in a sample from the subject, (b) determining resistance to an EGFR inhibitor, and subsequently (c) administering a therapeutically effective amount of an FTI to the subject if the sample is determined to have a HRAS mutation and be resistant to an EGFR inhibitor. The sample can be a tumor sample. In some embodiments, the methods include (a) determining a lung SCC patient to have a HRAS mutation, and subsequently (b) administering a therapeutically effective amount of an FTI to the subject. In some embodiments, the methods include (a) determining a lung SCC patient to have a HRAS mutation, and (b) determining resistance to an EGFR inhibitor, and, subsequently (c) administering a therapeutically effective amount of an FTI to the subject. In some embodiments, the FTI is tipifarnib. In certain embodiments, said FTI is administered in combination with chemotherapy. In certain embodiments, said chemotherapy comprises a platinum-based therapy, a taxane, or a combination thereof.

5.4. Exemplary FTIs and Dosages

In some embodiments, provided herein are methods to treat SCCHN in a subject with tipifarnib or selecting SCCHN patients for tipifarnib treatment based on the presence of a HRAS mutation. In some embodiments, the methods include treating the subject with another FTI described herein or otherwise known in the art. In some embodiments, the FTI is selected from the group consisting of tipifarnib, arglabin, perrilyl alcohol, lonafarnib (SCH-66336), L778123, L739749, FTI-277, L744832, CP-609, 754, R208176, AZD3409, and BMS-214662.

In some embodiments, the FTI is administered orally, parenterally, rectally, or topically. In some embodiments, the FTI is administered orally. In some embodiments, tipifarnib is administered orally, parenterally, rectally, or topically. In some embodiments, tipifarnib is administered orally.

In some embodiments, the FTI is administered at a dose of 1-1000 mg/kg body weight. In some embodiments, the FTI is administered twice a day. In some embodiments, the FTI is administered at a dose of 200-1200 mg twice a day. In some embodiments, the FTI is administered at a dose of 600 mg twice a day. In some embodiments, the FTI is administered at a dose of 900 mg twice a day. In some embodiments, tipifarnib is administered at a dose of 1-1000 mg/kg body weight. In some embodiments, tipifarnib is administered twice a day. In some embodiments, tipifarnib is administered at a dose of 200-1200 mg twice a day. In some embodiments, tipifarnib is administered at a dose of 600 mg twice a day. In some embodiments, tipifarnib is administered at a dose of 900 mg twice a day.

In some embodiments, the FTI is administered in treatment cycles. In some embodiments, the FTI is administered in alternative weeks. In some embodiments, the FTI is administered on days 1-7 and 15-21 of a 28-day treatment cycle. In some embodiments, the FTI is administered orally at a dose of 900 mg twice a day on days 1-7 and 15-21 of a 28-day treatment cycle. In some embodiments, tipifarnib is administered in treatment cycles. In some embodiments, tipifarnib is administered in alternative weeks. In some embodiments, tipifarnib is administered on days 1-7 and 15-21 of a 28-day treatment cycle. In some embodiments, tipifarnib is administered orally at a dose of 900 mg twice a day on days 1-7 and 15-21 of a 28-day treatment cycle.

In some embodiments, the FTI is administered for at least 3 cycles. In some embodiments, the FTI is administered for at least 6 cycles. In some embodiments, the FTI is administered for up to 12 cycles. In some embodiments, the FTI is administered orally at a dose of 900 mg twice a day on days 1-7 and 15-21 of a 28-day treatment cycle for at least three cycles. In some embodiments, tipifarnib is administered for at least 3 cycles. In some embodiments, tipifarnib is administered for at least 6 cycles. In some embodiments, tipifarnib is administered for up to 12 cycles. In some embodiments, tipifarnib is administered orally at a dose of 900 mg twice a day on days 1-7 and 15-21 of a 28-day treatment cycle for at least three cycles.

In some embodiments, provided herein is a method of treating a SCCHN in a subject with tipifarnib based on the presence of a HRAS mutation. In some embodiments, the SCCHN can be HPV negative SCCHN. In some embodiments, the SCCHN can be HPV positive SCCHN. In some embodiments, the SCCHN can be relapsed/recurrent SCCHN. In some embodiments, the SCCHN can be metastatic SCCHN. The method provided herein includes (a) determining the presence or absence of a HRAS mutation in a sample from the subject, and subsequently (b) administering a therapeutically effective amount of a tipifarnib to the subject if the sample is determined to have a HRAS mutation. The sample can be a tumor sample. In some embodiments, the methods include (a) determining a SCCHN patient to have a HRAS mutation, and subsequently (b) administering a therapeutically effective amount of a tipifarnib to the subject. In some embodiments, the methods include administering the subject with another FTI described herein or otherwise known in the art. In some embodiments, the FTI is selected from the group consisting of tipifarnib, arglabin, perrilyl alcohol, lonafarnib(SCH-66336), L778123, L739749, FTI-277, L744832, CP-609,754, R208176, AZD3409, and BMS-214662.

In some embodiments, the methods include (a) determining a SCCHN patient to be resistant to an EGFR inhibitor and to have a HRAS mutation, and subsequently (b) administering tipifarnib to the subject, wherein the tipifarnib is administered orally at a dose of 900 mg twice a day on days 1-7 and 15-21 of a 28-day treatment cycle. In some embodiments, the SCCHN patient has relapsed/refractory SCCHN. In some embodiments, the SCCHN patient has HPV negative SCCHN. In some embodiments, the SCCHN patient has HPV positive SCCHN.

In some embodiments, the methods further comprise administering a second therapy to the patient having SCCHN with a HRAS mutation. In some embodiments, the second therapy is a chemotherapy, such as cisplatin, 5-FU, carboplatin, paclitaxel, or platinum-based doublet (e.g., cisplatin/5-FU or carboplatin/paclitaxel). In some embodiments, the second therapy is taxanes and/or methotrexate. In some embodiments, the second therapy is a radiation therapy. In some embodiments, the second therapy include those targeting PI3K pathway: BKM120 (buparlisib), BYL719, Temsirolimus, Rigosertib; those targeting MET pathway: Tivantinib, Ficlatuzumab; those targeting the HER3 pathway, Patritumab; those targeting FGFR pathway: BGJ398; those targeting CDK4/6-cell cycle pathway: Palbociclib, LEEO11; RTK inhibitor: Anlotinib and chemotherapy: Oral Azacitidine. In some embodiments, the second therapy is an immunotherapy, such as anti-PD1 or anti-PDL1 antibodies. In some embodiments, the second therapy is a taxane.

In some embodiments, provided herein is a method of treating a lung SCC in a subject with tipifarnib based on the presence of a HRAS mutation. In some embodiments, the lung SCC can be HPV negative lung SCC. In some embodiments, the lung SCC can be HPV positive lung SCC. In some embodiments, the lung SCC can be relapsed/recurrent lung SCC. In some embodiments, the lung SCC can be metastatic lung SCC. The method provided herein includes (a) determining the presence or absence of a HRAS mutation in a sample from the subject, and subsequently (b) administering a therapeutically effective amount of a tipifarnib to the subject if the sample is determined to have a HRAS mutation. The sample can be a tumor sample. In some embodiments, the methods include (a) determining a lung SCC patient to have a HRAS mutation, and subsequently (b) administering a therapeutically effective amount of a tipifarnib to the subject. In some embodiments, the methods include administering the subject with another FTI described herein or otherwise known in the art. In some embodiments, the FTI is selected from the group consisting of tipifarnib, arglabin, perrilyl alcohol, lonafarnib (SCH-66336), L778123, L739749, FTI-277, L744832, CP-609,754, R208176, AZD3409, and BMS-214662.

In some embodiments, the methods include (a) determining a lung SCC patient to be resistant to an EGFR inhibitor and to have a HRAS mutation, and subsequently (b) administering tipifarnib to the subject, wherein the tipifarnib is administered orally at a dose of 900 mg twice a day on days 1-7 and 15-21 of a 28-day treatment cycle. In some embodiments, the lung SCC patient has relapsed/refractory lung SCC. In some embodiments, the lung SCC patient has HPV negative lung SCC. In some embodiments, the lung SCC patient has HPV positive lung SCC.

In some embodiments, the methods further comprise administering a second therapy to the patient having lung SCC with a HRAS mutation. In some embodiments, the second therapy is a chemotherapy, such as cisplatin, 5-FU, carboplatin, paclitaxel, or platinum-based doublet (e.g., cisplatin/5-FU or carboplatin/paclitaxel). In some embodiments, the second therapy is taxanes and/or methotrexate. In some embodiments, the second therapy is a radiation therapy. In some embodiments, the second therapy include those targeting PI3K pathway: BKM120 (buparlisib), BYL719, Temsirolimus, Rigosertib; those targeting MET pathway: Tivantinib, Ficlatuzumab; those targeting the HER3 pathway, Patritumab; those targeting FGFR pathway: BGJ398; those targeting CDK4/6-cell cycle pathway: Palbociclib, LEEO11; RTK inhibitor: Anlotinib and chemotherapy: Oral Azacitidine. In some embodiments, the second therapy is an immunotherapy, such as anti-PD1 or anti-PDL1 antibodies. In some embodiments, the second therapy is a taxane.

6. Examples

It is understood that modifications which do not substantially affect the activity of the various embodiments of this invention are also provided within the definition of the invention provided herein. Accordingly, the following examples are intended to illustrate but not limit the present invention. All of the references cited to herein are incorporated by reference in their entireties.

Example I

Tipifarnib Clinical Trial in Solid Tumor Patients Stratified Based on HRAS Mutation A Phase 2 clinical trial was initiated to use tipifarnib in the treatment of locally advanced unresectable or metastatic, relapsed and/or refractory, non-hematological malignancies with a known HRAS mutation. Second objectives include safety and tolerability of said malignancies. The first exploratory objective is to explore the antitumor activity in terms of progression free survival (PFS) and duration of response (DOR) of tipifarnib in said malignancies. The second exploratory objective is to explore the feasibility of collecting archival biopsies and analyzing these biopsies for the detection of tissue biomarkers potentially related to tipifarnib activity.

The clinical trial design includes enrolling 2 cohorts of 18 patients each. Cohort 1 enrolls subjects with malignant thyroid tumors with HRAS mutations, independent of thyroid histology. Cohort 2 enrolls, in stage 1, any subject with a non-hematological HRAS mutant tumor other than thyroid cancer who meets eligibility criteria, and in stage 2, head and neck squamous cell carcinomas (SCCHN/HNSCC). Based on the anti-tumor activity observed during stage 1 of cohort 2, the protocol was amended to restrict enrollment in stage 2 of Cohort 2 to subjects with SCCHN with HRAS mutations only.

This clinical trial was designed to include two stages, with the first stage including 11 evaluable patients, and the second stage including 7 additional evaluable patients, and a cohort would not proceed to the second stage if one or no objective response is observed in a cohort in the first stage. The clinical trial is considered positive if at least 4 responses are observed in a cohort out of 18 subjects. The primary endpoint is objective response rate, and tumor response assessments are conducted according to the Response Evaluation Criteria in Solid Tumors version 1.1 criteria (confirmation of response is required).

According to the protocol, tipifarnib is administered to enrolled patients at a starting dose of 900 mg, orally with food, twice a day (b.i.d.) for 7 days in alternating weeks (Days 1-7 and 15-21) in 28 day cycles. In the absence of unmanageable toxicities, subjects may continue to receive tipifarnib treatment for up to 12 months in the absence of disease progression and unmanageable toxicity. Treatment may continue beyond 12 months upon agreement of the Investigator and Sponsor. At the discretion of the investigator, the dose of tipifarnib can be increased to 1200 mg b.i.d. if the subject has not experienced dose limiting toxicities at the 900 mg dose level.

Tumor assessments are performed at screening and approximately every 8 weeks for the first 6 months (cycles 2, 4, 6) and then every 12 weeks (cycles 9, 12, 15, etc.) until disease progression, starting at the end of cycle 2.

Subjects who develop serious adverse events (SAE) or ≥grade 2 treatment-emergent adverse events (TEAE) that are deemed related to tipifarnib and lasting ≥14 days will not undergo dose escalation. Stepwise 300 mg dose reductions to control treatment-related, treatment-emergent toxicities are also allowed.

Subjects who develop serious adverse events (SAE) or ≥grade 2 treatment-emergent adverse events (TEAE) that are deemed related to tipifarnib and lasting ≥14 days will not undergo dose escalation. Stepwise 300 mg dose reductions to control treatment-related, treatment-emergent toxicities are also allowed.

Study Assessments:

Screening. As part of the screening procedures, all study subjects undergo the following: Informed Consent Form (ICF) completion, evaluation of inclusion/exclusion criteria, collection of tumor HRAS status information, medical history including the outcome and duration of response to the prior last anticancer therapy, complete physical examination, including weight and vital signs, use of concomitant medications, adverse event assessment, 12-lead ECG, ECOG performance status, standard laboratory panels including hematology, chemistry, coagulation, and urinalysis, pregnancy test in women with childbearing potential, and baseline tumor imaging. Serum tumor burden markers may also be collected at this point if deemed of interest by the Investigator. Collection of thyroglobulin and anti-thyroglobulin antibodies for differentiated thyroid cancer and calcitonin and CEA for medullary thyroid cancer is recommended.

Treatment Phase. The evaluations to be performed on Day 1 (+/−2 days) at each treatment cycle include: Symptom based physical examination, 12-lead ECG (Cycle 1 only), ECOG performance status, standard laboratory panels, pregnancy test in women with childbearing potential, and assessment of concomitant medications and adverse events. Tumor imaging will be repeated approximately every 8 weeks for the first 6 months (cycles 2, 4, 6) and then every 12 weeks (cycles 9, 12, 15, etc.) until evidence of disease progression, starting at end of cycle 2 (Day 22+/−5 days) or more frequently if deemed necessary by the Investigator. Blood samples for the assessment of serum tumor burden markers will also be collected at the same time points as tumor imaging assessments if samples were previously collected during screening procedures.

End of Treatment Visit. An End of Treatment Visit takes place within approximately 30 days from the last dose of trial treatment or immediately before the initiation of any other anticancer therapy, whichever occurs first. Subjects have a complete physical examination, ECOG performance status, a 12-lead ECG, standard laboratory panels, pregnancy test for women of childbearing potential, and an assessment of concomitant medications and adverse events. Further safety follow up is scheduled in the absence of recovery from treatment-related adverse events.

Additional Follow Up. Tumor imaging and samples for serum tumor burden marker assessment continue to be repeated in intervals of approximately 8 weeks for the first 6 months (cycles 2, 4, 6) and then every 12 weeks (cycles 9, 12, 15, etc.) until evidence of disease progression. Upon disease progression, subjects are contacted for survival and use of other anticancer treatments every 12 weeks until either death or 12 months after accrual in the subject's study cohort has been completed.

Example II

Objective Responses with Tipifarnib in Squamous Head and Neck Carcinoma with HRAS Mutations after Failure of Cetuximab Treatment Three subjects with a diagnosis of squamous cell carcinoma of the head and neck carcinoma (SCCHN) were enrolled in the exploratory open label phase 2 study of Example I. Subject 1 is a 77 year old white male with a diagnosis of nasal cavity cylindrical cell carcinoma/transitional cell carcinoma and SCCHN of the trachea as second primary who joined the tipifarnib study upon local relapse after prior paclitaxel, carboplatin and cetuximab therapy. The best response to cetuximab therapy with chemotherapy for this subject was disease stabilization. Subject 2 is a 21 year old white male with a maxilla SCC diagnosis and oral cavity SCCHN as second primary and lung metastasis. Subject 3 is a 59 year old white male with an oral cavity SCCHN. Subject 2 and 3 received cetuximab therapy alone or in combination with chemotherapy, respectively, subject 2 with a short-lived progression (2 cycles), followed by progressive disease, and subject 3 with a best response of progressive disease. Next generation tumor sequencing revealed the presence the Q22K HRAS mutation in the tumor of subject 1 and the Q61K HRAS mutation in subjects 2 and 3. No CASP8, TP53, or PIK3CA mutations were found. The tumor of subject 2 carries also a MAPK1 E322K mutation as well as point mutations in ABL1, NOTCH3, RET and ROS1. HPV status for these subjects is pending.

As part of the phase 2 tipifarnib trial, subjects received treatment with tipifarnib at a starting dose of 900 mg, po, bid daily on days 1-7 and 15-21 of 28-day treatment cycles. Subject 1 received treatment with 900 mg bid for 11 cycles at which point his dose of tipifarnib was reduced to 600 mg bid due to the onset of NCI CTCAE 4.03 grade 2 peripheral neuropathy. He continues on treatment and has been currently over one year on study. Subject 2 was dose reduced to 600 mg bid and then 300 mg bid during cycle 1 due to grade 2 peripheral neuropathy and continued on treatment for 6 additional cycles until symptomatic deterioration/ subject withdrawal at cycle 7. Subject 3 received 8 cycles of treatment with the 900 mg bid dose and continues on study. Other toxicities observed in these subjects were consistent with the overall safety profile previously reported for tipifarnib (Mesa. Expert Rev Anticancer Ther. 2006; 6:313-90).

Tumor assessments were performed at subject screening and approximately every 8 weeks for the first 6 months (cycles 2, 4, 6) and then every 12 weeks (cycles 9, 12, 15, etc.) until disease progression, starting at the end of Cycle 2. Additional tumor assessments could be conducted if deemed necessary by the Investigator or for a confirmation of an objective response. Both subject 1 and 3 experienced confirmed objective partial responses according to RECIST 1.1 criteria. Responses met criteria after 6 and 2 cycles of treatment, respectively. Subject 2 experienced disease stabilization with a minor 8% regression. His last tumor scan on study did not meet imaging criteria for disease progression, but he left the study after seven months of disease stabilization due to symptomatic deterioration. CT scans of the tumor response in patient 1 at baseline and at cycle 4, day 22, are shown in FIG. 1A-B.

In summary, reported herein are the outcomes of three subjects with advanced HRAS mutant SCCHN who received meaningful clinical benefit from tipifarnib therapy. HRAS has been known to play a more prominent role than other RAS species in SCCHN, particularly in oral cavity tumors and those that are HPV negative (Saranath et al. Br J Cancer. 1991; 63:573-578; Anderson et al. J Otolaryngol. 1992; 21:321-326; Anderson et al. Arch Otolaryngol Head Neck Surg. 1994; 120:755-760). Overall, approximately 5% of SCCHN carcinomas but up to 16% have been reported in HPV negative oral carcinoma (Nat Commun. 2013; 4:2873). A recent comprehensive genomic characterization of SCCHN by the Cancer Genome Atlas Network (Nature 517, 576-582, 2015) revealed the existence of a subgroup of oral cavity tumors with infrequent copy number alterations in conjunction with activating mutations of HRAS or PIK3CA, coupled with inactivating mutations of CASP8, NOTCH1 and TP53. According to this group, the three-gene constellation of wild-type TP53 with mutant HRAS and/or CASP8 may constitute an alternative pathway to tumorigenesis.

Cetuximab is currently approved for use as front line treatment of SCCHN in combination with chemotherapy or radiation or in the second line setting as single agent treatment after failure of platinum based therapy. No restriction or recommendations for use in SCCHN exist according to RAS gene status. In our study, subject 1 had a best response of stable disease to his last prior anti-cancer regimen (combination of chemotherapy and cetuximab) whereas subjects 2 and 3 were refractory to prior cetuximab monotherapy or in combination with chemotherapy, respectively. Of interest, subjects 2 and 3 had oral cavity tumors that carry the Q61K hotspot mutation whereas subject 1 had the uncommon Q22K mutation. It is unclear whether the differential outcome to cetuximab treatment could be in part related to histology or HRAS mutation type.

Tipifarnib is a potent and selective FTI. Phase II and III trials of this agent as monotherapy for solid tumors have been disappointing while some promising activity was observed in patients with myelodysplastic syndrome and acute myeloid leukemia (Mesa. Expert Rev Anticancer Ther. 2006; 6:313-90). Likewise, a prior study of another FTI, lonafarnib, in patients recurrent SCCHN after platinum-based therapy was closed at interim analysis due to the absence of objective responses (Hanrahan et al. Am J Clin Oncol. 2009; 32:274-9). Our results strongly support the hypothesis that tumor HRAS mutation may contribute to the identification of SCCHN patients who could benefit from tipifarnib therapy. HRAS mutations may also drive primary or acquired resistance to treatment with standard of care cetuximab based therapy. Further investigation of these hypotheses is warranted.

Example III

Efficacy Experiments Performed with Tipifarnib in Patient-Derived Xenograft Model of HRAS-Mutant Human Head and Neck Squamous Cell Carcinoma Experimental Methods and Procedures.

Tumor fragments from stock mice inoculated with selected primary human head and neck cancer tissues were harvested and used for inoculation into BALB/c nude mice. Each mouse was inoculated subcutaneously at the right flank with primary human head and neck cancer model HN1420 fragment (R4P5, 2-4 mm in diameter) for tumor development on day −26. HN1420 has the A146P HRAS mutation and wildtype TP53 and is resistant to cetuximab. The mice were grouped when the average tumor size reached about 224 mm$^3$ on day 0. Mice were allocated randomly into 2 experimental groups according to their tumor sizes. Each group consisted of 3 mice, 3 mice per cage. The day was denoted as day 0. The test articles were administered to the tumor-bearing mice from day 1 through day 21 with the schedule of twice-daily (BID)×21 according to predetermined regimen shown in Table 1.

TABLE 1

Study design

| Group | N | Treatment | Dose Level (mg/kg) | Dose Route | Dosing Frequency |
|---|---|---|---|---|---|
| 1 | 3 | Vehicle | — | p.o. | BID × 21 |
| 2 | 3 | Tipifarnib (R115777) | 80 | p.o. | BID × 21 |

Note:
N: animal number per group.
BID dosing interval was 6-8 h apart.

Tumor size was measured twice weekly in two dimensions using a caliper, and the volume is expressed in mm$^3$ using the formula: TV=0.5 a×b$^2$, where a and b are the long and short diameters of the tumor, respectively. The tumor size is then used for calculations of tumor growth inhibition (TGI) and T/C, as described below:

Tumor growth inhibition, % TGI=$(1-(T_i-T_0)/(V_i-V_0))$ *100; $T_i$ as the mean tumor volume of the treatment group on the measurement day; To as the mean tumor volume of the treatment group at day 1; $V_i$ as the mean tumor volume of control group at the measurement day; $V_0$ as the tumor volume of the control group at day 1.

The T/C value (%) is an indicator of tumor response to treatment, and one of commonly used anti-tumor activity endpoint; T and C are the mean tumor volume of the treated and control groups, respectively, on a given day.

Summary statistics, including mean and the standard error of the mean (SEM), are provided for the tumor volume of each group at each time point. Statistical analysis of difference in tumor volume among the groups at study termination was conducted using an independent sample t-test. All data were analyzed using SPSS 16.0. P<0.05 was considered to be statistically significant.

Results Summary and Discussion.

The efficacy of Tipifarnib (R115777) was evaluated in the treatment of HUPRIME® head and neck cancer xenograft model HN1420 in female BALB/c nude mice.

In group 1 (vehicle, p.o., BID×21) and group 2 (Tipifarnib, 80 mg/kg, p.o., BID×21), the body weight change at study termination, 1 week after the last dose, was 6.95% and 1.12%, respectively (not shown). There were no animal deaths, significant body weight loss, or dosing holidays during the study. Thus, the test compound Tipifarnib was well tolerated in the HN1420 tumor-bearing mice.

As shown in Table 2, tumor sizes rapidly increased in the vehicle-treated animals, reaching an average of around 650 mm$^3$ after one week, over 1000 mm$^3$ within two weeks and over 1700 mm$^3$ by the end of the study. By contrast, tumors in animals receiving tipifarnib remained essentially unchanged for the first two weeks and only increased in size by an average of 150 mm$^3$ during the four week course of the experiment.

TABLE 2

HN1420 Tumor Sizes in the Different Treatment Groups

| | Tumor Volume (mm$^3$) | |
|---|---|---|
| Days | Vehicle | Tipifarnib (80 mg/kg, BID × 21 |
| 0 | 221.47 ± 22.44 | 226.25 ± 8.07 |
| 3 | 398.19 ± 27.34 | 264.11 ± 3.31 |
| 7 | 647.63 ± 81.08 | 242.79 ± 26.04 |
| 10 | 851.50 ± 73.06 | 245.81 ± 12.09 |
| 14 | 1025.49 ± 64.10 | 240.97 ± 45.13 |

TABLE 2-continued

HN1420 Tumor Sizes in the Different Treatment Groups

| | Tumor Volume (mm³) | |
|---|---|---|
| Days | Vehicle | Tipifarnib (80 mg/kg, BID × 21) |
| 17 | 1207.08 ± 53.97 | 227.39 ± 25.57 |
| 21 | 1494.10 ± 88.38 | 239.26 ± 44.42 |
| 24 | 1660.68 ± 116.57 | 306.90 ± 45.74 |
| 28 | 1720.98 ± 115.39 | 376.10 ± 54.92 |

Note:
data expressed as Mean ± SEM.

As shown in FIG. 2, the mean tumor size of the vehicle treated mice reached 1494.1 mm3 on day 21. Tumor volume stabilization was achieved in Tipifarnib treated mice with TGI of 99% and T/C of 16% (P<0.001). The results of tumor sizes in different groups at different time points after treatments are shown in Table 3.

TABLE 3

Antitumor Activity of Tipifarnib in the Treatment of HUPRIME ® Head and Neck Cancer Xenograft Model HN1420

| Treatment | Tumor size (mm³)[a] on day 0 of treatment | Tumor size (mm³)[a] on day 21 of treatment | TGI (%) | T/C (%) | P value[b] |
|---|---|---|---|---|---|
| G1 Vehicle | 221.47 ± 22.44 | 1494.10 ± 88.38 | — | — | — |
| G2 Tipifarnib | 226.25 ± 8.07 | 239.26 ± 44.42 | 99 | 16 | <0.001 |

Note:
[a]Mean ± SEM;
[b]Compared with the vehicle by independent sample t-test.

In summary, Tipifarnib (R115777) produced significant anti-tumor activity against the primary HUPRIME® head and neck cancer xenograft model HN1420 in this study.

Example IV

Efficacy Experiments Performed with Tipifarnib in Patient-Derived Xenograft Model of HRAS-Mutant Lung Squamous Cell Carcinoma Experimental Methods and Procedures.

Tumor fragments from stock mice inoculated with selected primary human NSCLC tissues were harvested and used for inoculation into BALB/c nude mice. Each mouse was inoculated subcutaneously at the right flank with primary human NSCLC model LU1513 fragment (R4P6, 2-4 mm in diameter) for tumor development. LU1513 has the Q61K HRAS mutation and the V216M TP53 mutation and is resistant to cetuximab. The mice were grouped when the average tumor size reached about 212 mm³ after 55 days. Mice were allocated randomly into 2 experimental groups according to their tumor sizes. Each group consisted of 3 mice, 3 mice per cage. The day was denoted as day 0. The test articles were administered to the tumor-bearing mice from day 1 through day 21 with the schedule of twice-daily (BID)×21 according to predetermined regimen also used for the HN1420 model and shown in Table 1 above. Tumor size was measured twice weekly in two dimensions using a caliper, and the volume is expressed in mm³ using the formula: TV=0.5 a×b², where a and b are the long and short diameters of the tumor, respectively. The tumor size is then used for calculations of TGI, T/C, as described above in Example III. Statistical analyses were performed and interpreted as for the HN1420 model.

Results Summary and Discussion.

The efficacy of Tipifarnib (R115777) was evaluated in the treatment of HUPRIME® NSCLC xenograft model LU1513 in female BALB/c nude mice.

Figure 3:
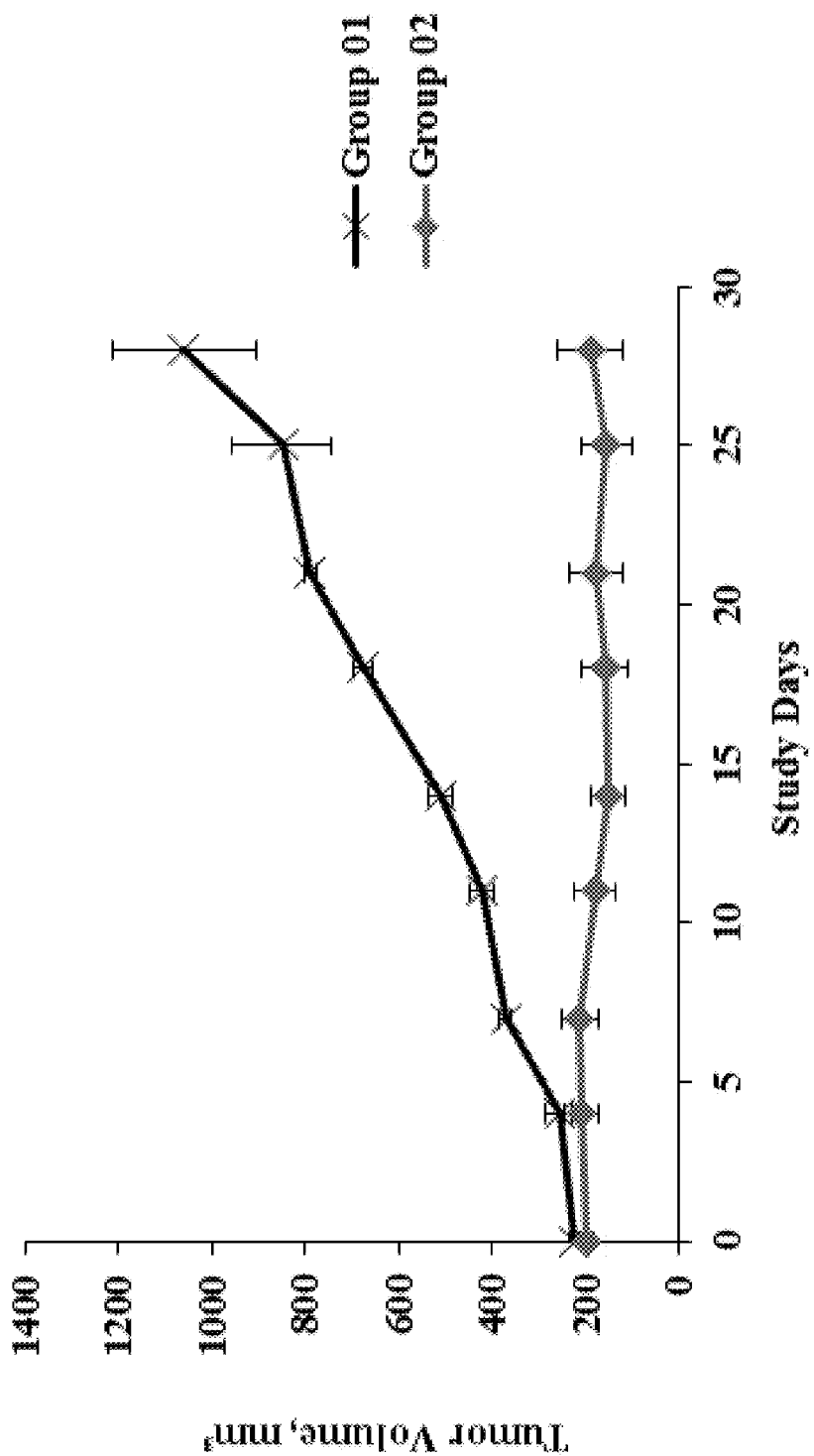
FIG. 3. Tumor Volumes of mice in different groups during tipifarnib treatment in HUPRIME® NSCLC xenograft model LU1513, wherein group 01 is the vehicle group and group 02 is the tipifarnib group.

In group 1 (vehicle, p.o., BID×21) and group 2 (Tipifarnib, 80 mg/kg, p.o., Bid×21), the body weight change at study termination was −5.13% and −0.54%, respectively (FIG. 3). There has been no animal death, significant body weight loss, or dosing holiday during the study. Thus, the test compound Tipifarnib was well tolerated in the LU1513 tumor-bearing mice.

As shown in Table 4, tumor sizes increased quite rapidly in the vehicle-treated animals, reaching an average of around 375 mm³ after one week, over 500 mm³ within two weeks and over 1000 mm³ by the end of the study. By contrast, tumors in animals receiving tipifarnib barely grew at any time during the course of the experiment; indeed, after 28 days average tumor size was slightly smaller than on day 1. Among the individual tumor-bearing animals, one tumor had modestly increased in size, one remained static and a third regressed by approximately 75%.

TABLE 4

LU1513 Tumor Sizes in the Different Treatment Groups

| | Tumor Volume (mm³) | |
|---|---|---|
| Days | Vehicle | Tipifarnib (R115777), 80 mg/kg, BID × 21 |
| 0 | 224.40 ± 15.45 | 198.64 ± 28.54 |
| 4 | 257.86 ± 29.70 | 209.42 ± 36.66 |
| 7 | 372.40 ± 11.63 | 212.62 ± 38.76 |
| 11 | 420.36 ± 26.88 | 179.72 ± 43.67 |
| 14 | 509.08 ± 26.34 | 150.11 ± 36.87 |
| 18 | 677.45 ± 19.63 | 158.82 ± 49.17 |
| 21 | 788.69 ± 14.38 | 175.78 ± 56.99 |
| 25 | 850.24 ± 104.73 | 154.50 ± 53.59 |
| 28 | 1058.26 ± 152.35 | 189.94 ± 70.66 |

Note:
data expressed as Mean ± SEM.

As shown in FIG. 2, the mean tumor size of the vehicle treated mice reached 1058.26 mm³ at study termination. Tumor volume stabilization was achieved in Tipifarnib treated mice with TGI of 101% and T/C of 18% (P=0.007). The results of tumor sizes in different groups at different time points after treatments are shown in the Table 5.

TABLE 5

Antitumor Activity of Tipifarnib in the Treatment of HUPRIME ® NSCLC Xenograft Model LU1513

| Treatment | Tumor size (mm³)[a] on day 0 of treatment | Tumor size (mm³)[a] on day 28 of treatment | TGI (%) | T/C (%) | P value[b] |
|---|---|---|---|---|---|
| G1 Vehicle | 224.40 ± 15.45 | 1058.26 ± 152.35 | — | — | — |
| G2 Tipifarnib | 198.64 ± 28.54 | 189.94 ± 70.66 | 101 | 18 | 0.007 |

Note:
[a]Mean ± SEM;
[b]Compared with the vehicle by independent sample t-test.

In summary, the test compound Tipifarnib (R115777) produced significant anti-tumor activity against the primary HUPRIME® NSCLC xenograft model LU1513 in this study.

---

We claim:

1. A method of treating EGFR inhibitor-refractory squamous cell carcinoma of the head and neck (SCCHN) in a subject, wherein the SCCHN has an HRAS mutation, comprising administering to the subject tipifarnib.

2. The method of claim 1, wherein said HRAS mutation comprises an amino acid substitution at a codon selected from a group consisting of G12, G13, Q61, Q22, K117, A146, and any combination thereof.

3. The method of claim 1, wherein said SCCHN does not have K-Ras mutation or N-Ras mutation.

4. The method of claim 3, wherein said SCCHN has wild type K-Ras and wild type N-Ras.

5. The method of claim 1, wherein said SCCHN is HPV negative.

6. The method of claim 1, wherein said SCCHN is recurrent or metastatic.

7. The method of claim 1, wherein said SCCHN is relapsed SCCHN.

8. The method of claim 1, wherein the SCCHN is SCCHN of the trachea.

9. The method of claim 1, wherein the SCCHN is SCCHN of the maxilla.

10. The method of claim 1, wherein the SCCHN is SCCHN of the oral cavity.

11. The method of claim 1, wherein the EGFR inhibitor is cetuximab.

12. The method of claim 1, wherein the EGFR inhibitor is cetuximab, panitumumab, zalutumumab, erlotinib, AZD9291, gefitinib, icotinib, rociletinib, poziotinib, afatinib, pelitinib, ASP8273, Luminespib, or XL647.

13. The method of claim 12, wherein the EGFR inhibitor is cetuximab, panitumumab, or zalutumumab.

14. The method of claim 12, wherein the EGFR inhibitor is erlotinib.

15. The method of claim 12, wherein the EGFR inhibitor is AZD9291.

16. The method of claim 12, wherein the EGFR inhibitor is gefitinib.

17. A method of treating an SCCHN in a subject, wherein a sample from the subject has an HRAS mutation, and wherein the subject has never been treated with an EGFR inhibitor, comprising administering a therapeutically effective amount of tipifarnib to said subject and not administering an EGFR inhibitor.

18. The method of claim 17, wherein said HRAS mutation comprises an amino acid substitution at a codon selected from a group consisting of G12, G13, Q61, Q22, K117, A146, and any combination thereof.

19. The method of claim 17, further comprising determining the presence or absence of a K-Ras mutation or a N-Ras mutation, wherein said sample does not have K-Ras mutation or N-Ras mutation.

20. The method of claim 19, wherein said sample has wild type K-Ras and wild type N-Ras.

21. The method of claim 17, wherein said sample is a tissue biopsy or a tumor biopsy.

22. The method of claim 17, wherein determining the presence or absence of a HRAS mutation comprises: (i) analyzing nucleic acids obtained from said sample, wherein said HRAS mutation is determined by sequencing, Polymerase Chain Reaction (PCR), DNA microarray, Mass Spectrometry (MS), Single Nucleotide Polymorphism (SNP) assay, denaturing high-performance liquid chromatography (DHPLC), or Restriction Fragment Length Polymorphism (RFLP) assay; or (ii) analyzing proteins obtained from said sample.

23. The method of claim 17, wherein said SCCHN is HPV negative.

24. The method of claim 17, wherein said SCCHN is at an advanced stage or metastatic.

25. The method of claim 17, wherein said SCCHN is relapsed SCCHN.

26. The method of claim 17, wherein the SCCHN is SCCHN of the trachea.

27. The method of claim 17, wherein the SCCHN is SCCHN of the maxilla.

28. The method of claim 17, wherein the SCCHN is SCCHN of the oral cavity.

29. The method of claim 17, wherein the EGFR inhibitor is cetuximab.

30. The method of claim 17, wherein the EGFR inhibitor is cetuximab, panitumumab, zalutumumab, erlotinib, AZD9291, gefitinib, icotinib, rociletinib, poziotinib, afatinib, pelitinib, ASP8273, Luminespib, or XL647.

31. The method of claim 30, wherein the EGFR inhibitor is cetuximab, panitumumab, or zalutumumab.

32. The method of claim 30, wherein the EGFR inhibitor is erlotinib.

33. The method of claim 30, wherein the EGFR inhibitor is AZD9291.

34. The method of claim 30, wherein the EGFR inhibitor is gefitinib.

\* \* \* \* \*